United States Patent
Rao

(10) Patent No.: US 10,789,034 B2
(45) Date of Patent: Sep. 29, 2020

(54) SYSTEM FOR INFORMATION DISPLAY

(71) Applicant: Abhijit Rao, Irvine, CA (US)

(72) Inventor: Abhijit Rao, Irvine, CA (US)

( * ) Notice: Subject to any disclaimer, the term of this patent is extended or adjusted under 35 U.S.C. 154(b) by 116 days.

(21) Appl. No.: 15/531,418

(22) PCT Filed: Nov. 27, 2015

(86) PCT No.: PCT/US2015/062831
§ 371 (c)(1),
(2) Date: May 26, 2017

(87) PCT Pub. No.: WO2016/086221
PCT Pub. Date: Jun. 2, 2016

(65) Prior Publication Data
US 2017/0315767 A1   Nov. 2, 2017

Related U.S. Application Data

(60) Provisional application No. 62/123,804, filed on Nov. 28, 2014, provisional application No. 62/176,798, (Continued)

(51) Int. Cl.
*G06F 3/147* (2006.01)
*G06F 3/14* (2006.01)
*G09G 5/00* (2006.01)
*H04L 29/08* (2006.01)
*G06Q 30/02* (2012.01)
(Continued)

(52) U.S. Cl.
CPC ............ *G06F 3/147* (2013.01); *G06F 3/1446* (2013.01); *G06Q 30/02* (2013.01); *G06Q 30/06* (2013.01); *G09G 5/006* (2013.01); *H04L 29/08* (2013.01); *H04L 69/324* (2013.01); *G06Q 30/0241* (2013.01); *G09G 3/344* (2013.01); *G09G 2330/02* (2013.01); *G09G 2370/022* (2013.01);
(Continued)

(58) Field of Classification Search
CPC combination set(s) only.
See application file for complete search history.

(56) References Cited

U.S. PATENT DOCUMENTS

2009/0168088 A1 * 7/2009 Rosenblatt ............... H04B 7/26
  358/1.12
2014/0313178 A1 * 10/2014 Noorbakhsh ........ G09G 3/2096
  345/211

* cited by examiner

*Primary Examiner* — Vinh T Lam
(74) *Attorney, Agent, or Firm* — Mason A. Gross; The Law Office of Mason A. Gross, PLLC

(57) ABSTRACT

Apparatus and methods for generating, displaying, and updating information, such as aggregated information or content, provide engagement techniques, delivering new experiences to an audience, viewer, visitor, customer, etc. Applications prepare information, such as pricing, to present or display on display devices, signage, etc. A platform manages the display devices and the content on the display devices to engage the audience. The display devices are low-powered, may be ePaper-based, and have minimum circuitry and reduced resource requirements. Information and control signals may be transferred to, and power and ground established with, the display devices via transient electrical and frictional mechanisms. Changes made in information presented may depend on the needs or relevancy to the audience or the needs or desires of a content provider, business or, organization, presenter, etc. Updates or format/layout changes for presenting the content may be based on the efficacy of content previously presented.

2 Claims, 32 Drawing Sheets

Related U.S. Application Data filed on Feb. 27, 2015, provisional application No. 62/178,958, filed on Apr. 23, 2015.

(51) Int. Cl.
*G06Q 30/06* (2012.01)
*G09G 3/34* (2006.01)
*G16H 10/60* (2018.01)

(52) U.S. Cl.
CPC ......... *G09G 2380/06* (2013.01); *G16H 10/60* (2018.01)

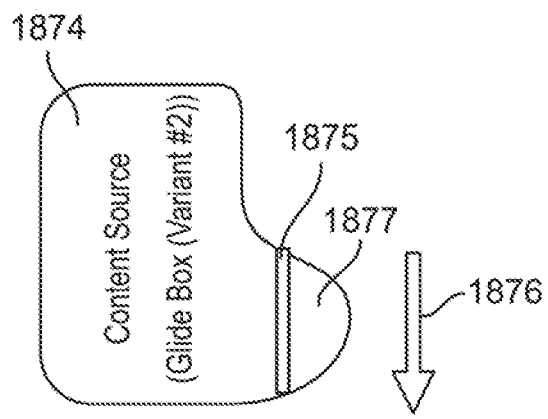
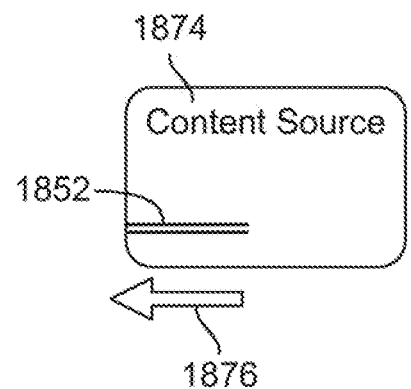
FIG. 19          FIG. 20
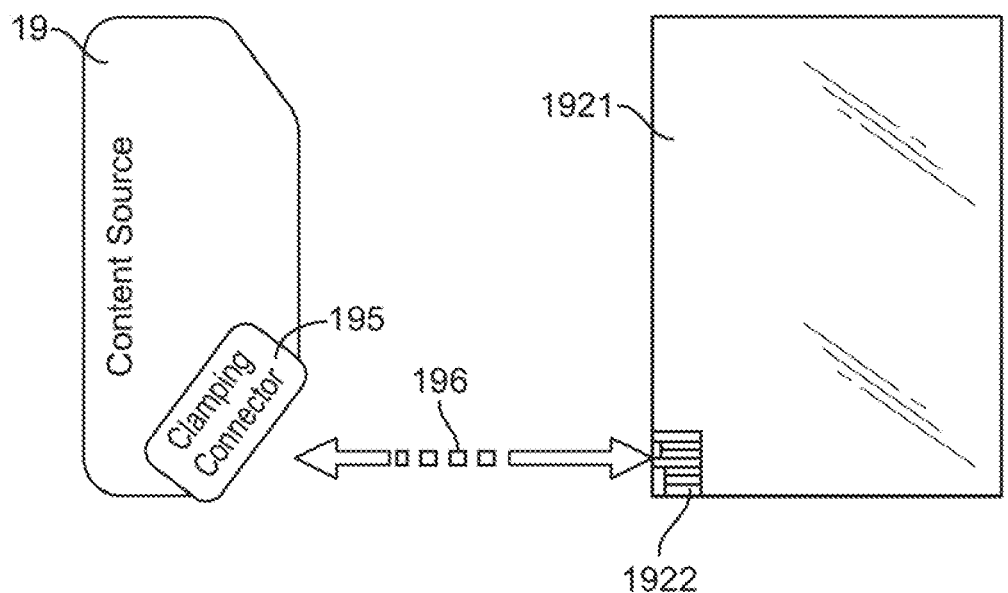
FIG. 21

XML data: field_list.xml

...

```
<row_one>
   <fieldname> Name </fieldname>
   <fieldtype> String </fieldtype>
    ...
</row_one>
```

...

XML schema definition: field.xsd

...

```
<row>
   <element name="field name"
    ...
</row>
```

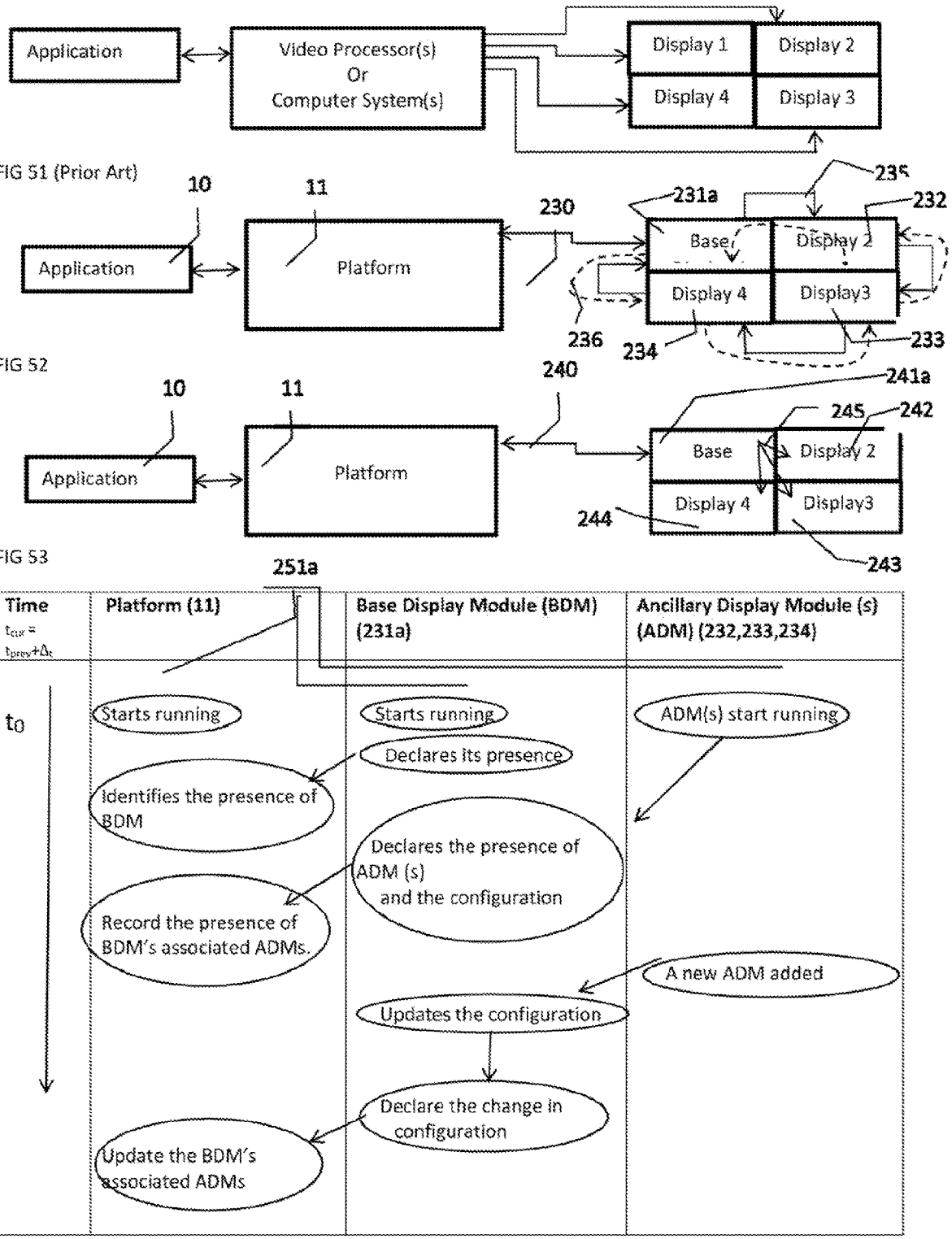

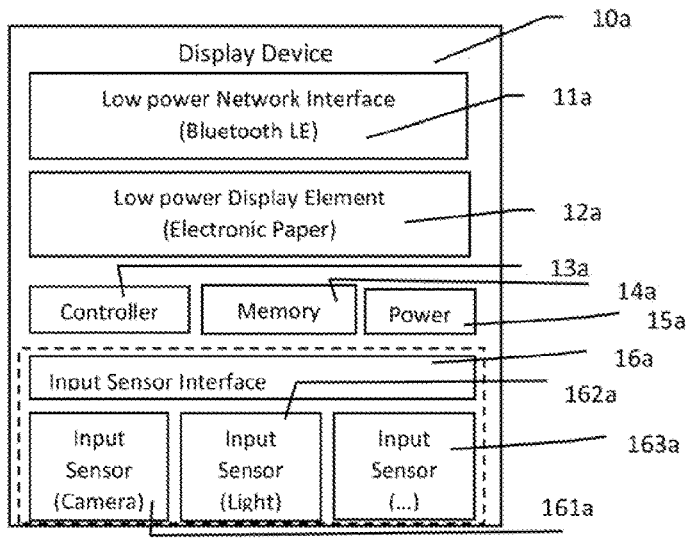
FIG 59.
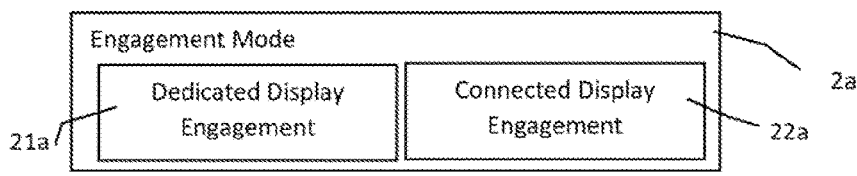
FIG 60.
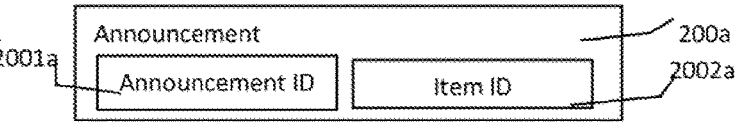
FIG 61.
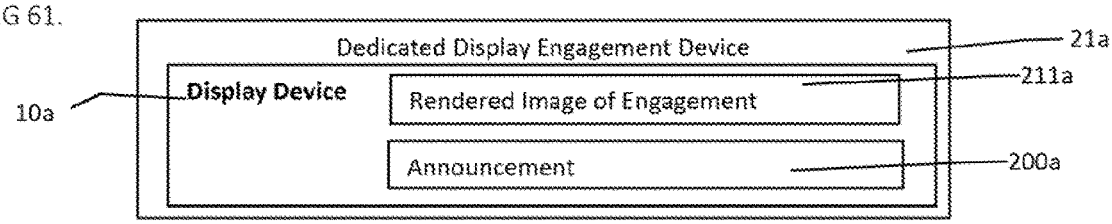
FIG 62.
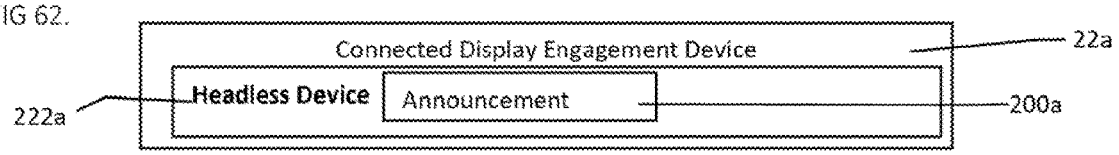
FIG 63.
FIG 64.
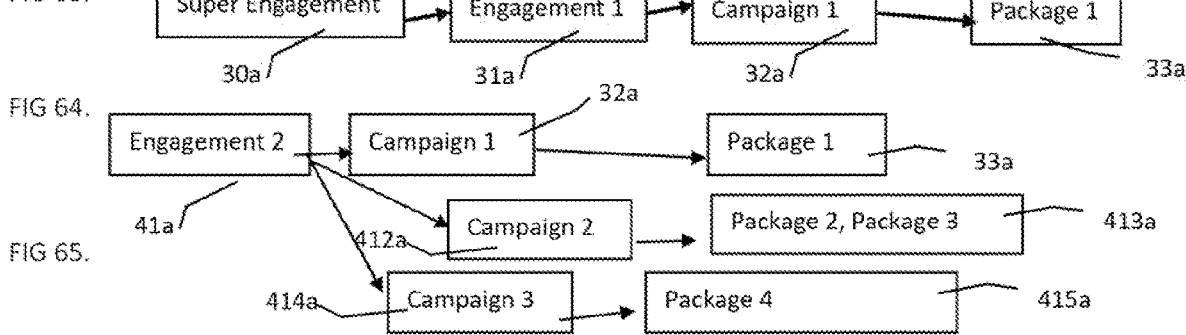
FIG 65.

SYSTEM FOR INFORMATION DISPLAY

CROSS-REFERENCE TO RELATED APPLICATIONS

This application claims the benefit of U.S. Provisional Application No. 62/123,804, filed Nov. 28, 2014, U.S. Provisional Application 62/176,798, filed Feb. 27, 2015, and U.S. Provisional Application 62/178,958, filed Apr. 23, 2015.

TECHNICAL FIELD

The present invention generally is related to presenting or displaying information, such as aggregated information (e.g., content), that engages an audience, the information prepared by applications and presented on devices, such as display devices or display modules, and wherein the aggregated information and control signals may be transferred to the devices either via transient coupling mechanisms or other coupling mechanisms known in the art. More particularly the present invention is related to one or more low-powered display devices or signage that presents aggregated information to an audience, such as pricing and announcements, and uses a platform to manage the presenting or displaying of the information.

BACKGROUND

The ubiquitous media for presenting aggregated information in a predefined format is paper. The aggregated information is printed on the paper, then viewed or used and typically later discarded, recycled, or archived for subsequent viewing or use.

The presentation of aggregated information is a key requirement in various vertical markets. A vertical market is a market in which vendors offer goods and services specific to an industry, trade, profession, or other group of customers with specialized needs. Table 1 lists a sample of such aggregated information, which is referred to as an Aggregated Information Sink (AIS), prepared by one or more applications. The application may be software code running on a computer, server, or computing device or similar system, or it may be software code running on a specialized hardware implementation, such as used in a weather station or other embedded systems. The AIS is a type of "sink" because the aggregated information resides there for viewing and use. The AIS typically is printed on paper due to various necessities.

TABLE 1

Vertical Market and various AIS used in those markets

| Vertical Market | Exemplary Aggregated Information Sink |
|---|---|
| Healthcare & Public Policy | Bedside Shift Report, Child Health Record, and/or Vaccination Record |
| Retail Industry | Bills, Receipts, Brochure, Price tags, Announcements |
| Real Estate | Neighborhood Home Sales Flyer |
| Financial Services | Cash Reconciliation |
| NGO | Community Progress Report, Monthly Activity Report |
| Consumer Electronics | Print at home (Tickets, Recipes, Anything temporary - Email, Documents, Itineraries), Weather Report |
| Museums | Exhibit Pamphlet, Family Guide |
| Government | Registration/License Document |
| (Across all Industries) | Financial Reports, Status Reports, Compliance Reports, Shareholder Reports, Draft Printouts |
| Business Owner | Advertisement, Promotional Flyer, Menu Card, Price list |
| Transportation | Advertisements on Vehicles |

Using such AIS is subject to various limitations that may be illustrated by considering a Child Health Record (CHR) AIS. These limitations are observable with various other types of AIS. With a CHR, typically the layout for the aggregated information is preprinted, as it is for other AIS. The predefined and preprinted formats have been used and reused for many years, but they are limited in providing contemporary and relevant information from being conveyed. For example, they have not kept up with changes in social messaging for providing messages that may be desirable to convey to a particular recipient or recipients. The layout is static and adding anything beyond the existing layout is impossible or nearly so. Today, for example, there is the need to create awareness about juvenile obesity and diabetes in the community, but pre-printed pamphlets like those distributed in a physician's office are static and often ignored. Parents have to deal with two sources, the CHR and the pamphlet, to get the information. Such AIS are generic and the format and style are for a general reader. They are not customized to meet the needs of the specific reader, viz. the layout of the CHR generally does not meet the unique needs of a particular child and parent, such as specific economic factors or particular literacy level of the parents, or whether juvenile diabetes issues should be relevant to their child.

Often, depending on the specific jurisdiction/locale/region, the same data is presented in a different but nevertheless static layout/format. One example is when moving the CHR from one region (e.g., country) to another, it may require manual translation services but no other changes.

The CHR also may get damaged, tattered, etc., which often requires that it be placed in a protective sleeve, pouch, or lamination, and it may be difficult to replace if missing. If the CHR or another type of AIS is lost, such as a tax document, all the confidential information may be gone unless it can be retrieved.

Another way to illustrate the limitations that exist across various AIS is to consider price signs/price lists, for example, as used by commercial retailers to sell products. Paper and similar materials are used for traditional signs and banners to display information to a consumer or buyer of products. These traditional signs and banners go stale soon because their content is static. For example, a sale may be over or a product price may have changed. Moreover, printed paper and paper signage used for pricing signs and announcements for sales and promotions in retail spaces such as stores, hotels, and malls, for exhibit-related information and to announce events in museums, and used for similar purposes in other verticals, for instance, enterprise offices, hospitals, theme parks, etc., is expensive, may have high implementation and operational costs, and taxes the environment. Changing the information on such wholly passive paper signage may also be a very involved task. Further, monitor-based signage, such as the typical multi-monitor or multi-display video-wall, is expensive as well, hard to use, have tremendous cost overhead, and their management is usually out-sourced. Specialized video processors often are required to manage and drive these video walls. Other options, including standard computers with special multiple-output specialized graphic cards to drive the video-wall and TV-based signage, although content may be replaced with relative ease, are expensive, and also passive. The term "passive" indicates that these signage do not actively or interactively engage the target audience, i.e., unless the target audience visually looks and sees them or looks for them, the audience might not even know that these signage exist.

These types of signage are not interactive and do not engage a user or sponsor of the signage with any feedback or inputs from viewers or the audience. The information displayed on the signage is not driven in real-time by audience behavior. There may be a significant lag between an analysis of audience behavior or reaction relative to the paper or signage, for predicting behavior, and then updating the information being displayed based on such analysis and behavior.

Today, customers are accustomed to an online experience that involves learning more about a product being sold or a service being offered by viewing, for example, relevant reviews, tweets, likes, pins, and so on a computer. Such information may not be provided to an on-site shopper or visitor at the premises a retail brick-and-mortar store, museum, theme park, hotel, hospital, office space, etc. In many respects, the online user has much more information available to them when compared to the on-site customer, visitor or shopper. Similarly, a visitor to a medical center may be unable to get access to personalized or hyper-relevant information easily. These customers and visitors should be offered those experiences.

Although the discussion so far has been about paper, monitors, and TVs as display devices, other types of devices may be used for displays, such as bi-stable display devices, for example, electronic paper (ePaper) or electronic or electrophoretic ink, which is a type of electronic paper display (e.g., E Ink®). These are typically thin and lightweight devices, which are based on technologies that display a rendered image and text for long periods of time even after power is no longer supplied to them. Circuitry to drive displays, as well as electrophoretic displays are described in U.S. Pat. No. 5,617,111 to Saitoh, U.S. Pat. No. 6,531,997 to Gates, et al., U.S. Pat. No. 7,126,577 to Zhou, U.S. Pat. No. 7,012,600 to Zehner, U.S. Pat. No. 6,906,851 to Yuasa, U.S. Pat. No. 6,445,489 to Jacobson, and U.S. Pat. No. 7,307,779 to Cernasov, which are incorporated by reference herein in there entireties. Adding connectors to ePaper or electrophoretic displays to enable wired connections, such as DVI and HDMI, however, only weighs them down. Also, updating such devices involves transferring data and control signals only upon fully and physically positioning, mating, or connecting a plug or connector to a corresponding socket or receptacle in another device to establish a firm electrical coupling for receipt of content. These and other display devices, when instead using a wireless connection, require pairing with another device. Such wireless connections, for example, for Wi-Fi and Bluetooth, also require adding hardware circuitry and an extended power source for the display device.

SUMMARY

Display devices (also referred to as display modules herein) receive aggregated information (e.g., content) to display to a viewer, visitor, or customer. Typically, a display module is connected with an electrical coupling mechanism that is a wired or a wireless connection, as discussed above, to a content-providing system, i.e., the source of the content (referred to herein as "content source"). In accordance with certain embodiments of the invention, the display module is connected to the content source instead using a transient coupling mechanism for transferring content. The content source may be a computer(s), server(s), or the like that may or may not be distributed on a network. An application controls the content received by the display module transferred from the content source. The content source may host the application or the application may be hosted externally to the content source, e.g., on a distributed network. The content source may connect to the display device over a public network such as the Internet or a private network such as a virtual private network (VPN).

Embodiments of the invention provide a platform(s) that allows an application(s) and a service(s) to use display devices and other engagement devices to present the aggregated information, pricing signage, and/or announcement signage. The application(s) was disclosed in the previously filed provisional patent application titled "System for an information display device that engages an audience" (Ser. No. 62/178,958, filed Apr. 23, 2015) by the same inventor. With the advent of numerous display types, techniques are disclosed to use and manage one or more of such display devices to function as a sink (AIS) for presenting the aggregated information and signage. The platform(s) provides a new class of audience, visitor, or viewer engagement techniques, delivering new experiences to an onsite visitor or shopper at the premises of brick-and-mortar stores, museums, retail spaces, hotels, malls, enterprise offices, hospitals, theme parks, etc., or for viewing in or on vehicles, such as internal and external signage on a bus. The word "visitor" as used herein may mean a shopper in a retail environment, person in a museum, "walk-in" customer, or employee in a brick-and-mortar organization, or the like, depending on the context. The audience towards whom the engagement techniques are targeted is referred to as a visitor as well, who may also be referred to interchangeably as a "shopper" or a "customer."

The provisional application Ser. No. 62/176,798 by the same inventor discloses a display device and a platform, which may be an embodiment for delivering the visitor engagement techniques disclosed herein. These visitor engagement techniques are enabled by a combination of a hardware platform and a software platform. This combination forms a basis for a preferred embodiment of the present invention. Although, in other embodiments, they may be enabled by a hardware platform only or a software platform only. The hardware platform typically uses wireless connectivity that requires very low power to operate and also requires no network infrastructure. A Wi-Fi network is a typical example of a wireless network that requires network infrastructure. Network infrastructure refers to the hardware and software resources of an entire network that enable network connectivity, communication, operations, and management of the network. An access point in a Wi-Fi network is a hardware resource and is part of a network infrastructure. The hardware platform may also include one or more ultra-low power display devices. Average power consumed in typical prior systems with a display is dominated by the display components and communication components. In accordance with an embodiment of the invention, the benefits of ultra-low power display devices are maintained in the systems disclosed and described. In a preferred embodiment, examples for ultra-low power display devices are the bi-stable display devices such as the electrophoretic displays (e.g., ePaper by eInk®.

The platform includes logic that may include software code, hardware, or a combination of both, such as a collection of software modules and services that may reside on a server system. Certain building blocks of the platform may be in external hardware systems, such as computing systems external to the hardware system that hosts other portions or building blocks of the platform. The platform may also be hosted in a distributed format on different servers. Such external hardware systems may reside in the Cloud and may be accessible through a private network or through a public network, such as the Internet, or through a combination of public and private networks. Embodiments of the invention provide a platform that connects the application(s) such as those used for pricing management, digital engagement, etc., and a content source together. As used herein, the word "platform," when referring to the disclosed invention, may indicate a hardware platform or a software platform, or a combination of both.

The software platform may have interfaces to various social media and other interfaces, such as content management systems and point of sale systems. The software platform has the ability to perform analytics on data collected to provide insights that may be used to influence the behavior of the visitor by modifying the engagement parameters, as will be described below.

The embodiments that provide the transient coupling mechanisms for transferring data or content from a content source to a display device or module do not require a plug or connector to be completely positioned, latched, mated, or connected fully to its corresponding socket or receptacle to transfer such data or content. That is, it does not have to be completely "plugged in," for example, like when a USB connector is fully plugged into its corresponding USB receptacle. The display modules may be electronic paper (ePaper)-based displays, which are thin, light, and may be bendable and/or foldable. The display device or module also may be based on other types of devices to present aggregated information to the viewer(s).

The platform connects an application(s) and a content source(s) together. Certain embodiments of the invention provide one or more instances of the platform that connect one or more applications, such as those used for pricing management, digital engagement, etc., and a content source together. In some of these embodiments the platform predominantly is a collection of software modules.

In certain embodiments of the invention, the application and the platform will be hosted on the content source. In other embodiments, the application(s) is hosted external to the content source, e.g., on a network client and connects to the content source through the platform. In embodiments in which the application is hosted external to the content source, the application is connected to the content source through the platform. In certain embodiments, a content source device hosts the application and the platform in memory on the content source device, such as described in the previously filed provisional patent application, "Platform for Transferring Content to Display Devices" (Ser. No. 62/176,798, filed Feb. 27, 2015) by the same inventor, which discloses a display device, a content source device, and a platform. In other embodiments, the application and the platform may be hosted on different machines, computing devices, servers, etc., or other devices on a network. In yet other embodiments the application, the platform, and the content source device may be hosted external to each other.

When the application(s) is required to or decides to send information to the display module, it communicates with and informs the platform, and then the platform prepares the content and sends it to display module. The platform prepares the content by rendering the content as per the display module's characteristics, such as the screen size of the display module, its resolution, color density, etc., and any details of a multi-display module setup (assuming it is a multi-display module setup). The content source then transfers the content to the display module the content source is electrically coupled to for presentation or display when the latter electrically couples (which may be a transient electrical coupling) with the content source. Certain exemplary methods for transient electrical coupling were described in the previously filed provisional patent application entitled "System and Method to Transfer Content to a Display Module" (Ser. No. 62/123,804, filed Nov. 28, 2014) by the same inventor, although other methods are contemplated as would occur to a person of ordinary skill in the art. In certain embodiments of the invention, the content source may use wired (such as USB) or wireless (such as Bluetooth or Wi-Fi) technologies to transfer the content to the display module.

Embodiments of the invention that include a transient coupling mechanism allow transient electrical contact to be made to the display module or display device, e.g., to a display module based on ePaper, through a coupling contact to receive content and then display the content on the display module. The content itself may originally or previously have been meant to be printed on paper. Other embodiments of the invention that employ traditional coupling mechanisms, such as USB, may also allow content to be displayed on display modules based on ePaper. Thus, embodiments of the invention reduce or eliminate the need to print on paper, and include new systems and methods to increase the adoption of ePaper with minimum circuitry. Moreover, certain embodiments of the invention provide a new class of display device, which may include various regions for different functions, such as for display of the content, authentication, power source, user feedback, I/O, and communication.

In accordance with embodiments of the invention, the platform may summarize aggregated information of interest to a viewer or use and make it available when required. The platform does so by providing methods to organize and obtain access to information sources. The platform may bring in local neighborhood or social information or experience, so that it may be used for an AIS that needs it. The platform has the ability to present the aggregated information in different languages of choice. The platform is aware of the characteristics of the display device(s), so the platform is capable of preparing the aggregated information for one or multiple devices, each with distinct characteristics. Security and accessibility of the aggregated information also is managed by the platform. Accessibility refers to assistive technology as well as direct access to the information (e.g., as through Web Services).

As discussed above, embodiments of the invention allow adaptation of the ePaper, electrophoretic ink (e.g., E Ink®) displays, or other typically thin and lightweight display technologies, which display a rendered image and text for long periods of time even if no power is supplied, to be used as display elements to build display device-based digital signage that replace traditional signs and banners. Such digital signage may be managed from a host that includes the application and possibly the platform as well (as was discussed previously). The digital signage is easy to use and may be updated easily and quickly in real-time or nearly real-time. Embodiments of the invention also provide a system to implement a multi-display or multi-screen setup when using ePaper or other display technologies, such as a multi-screen setup with less resource requirements. The multi-screen setup may be made up of the display devices or display elements discussed herein.

Thus, embodiments of the invention provide advantages and efficiencies in many ways over traditional paper and digital signage. While the predefined formats of traditional paper and digital signage that display predefined messages restrict contemporary and relevant information from being conveyed, embodiments of the invention provide apparatus and methods that may generate updated/new messages for a viewer or visitor that include relevant and contemporary information, where the information presented is changeable from what was previously presented. What changes are made to the information presented may depend on the needs or what may be relevant to the viewer or visitor or the needs or desires of the business owner, business type, presenter, etc. Embodiments of the invention further provide methods that generate updates/new format and layout of messages to be conveyed based on the efficacy of the previously displayed messages. Also, while traditional paper and signage systems have limited ways to engage the viewer or visitor, embodiments of the invention provide a platform for a new class of engagement techniques, delivering new experiences to an onsite viewer or visitor that may integrate social media data to provide personalized messages as part of engaging the viewer or visitor. Moreover, embodiments of the invention that include a transient electrical coupling mechanism do not necessarily require active power sources to be located on the display device itself, allowing, for example, ePaper to be used efficiently as a paper replacement with minimum circuitry and vastly reduced resource requirements.

The inventive concepts herein are unified in their purpose, disclosing systems, methods and apparatus for efficient presentation of aggregated information. The inventive concepts may be construed as elements in a stack and thus can be grouped into three categories. First, at the lowest level, the invention relates to a transient electrical and frictional (i.e., touching while moving) coupling mechanism in which a display device's electrical connector as it moves is making electrical and frictional contact with a content source's electrical receptacle (or while the content source's receptacle is moving and making electrical and frictional contact with the display device's connector), as an alternate to known coupling mechanisms which can be classified as wired or wireless. The transient electrical and frictional coupling mechanism and the use of an ultra-low power display device in certain embodiments without requiring a power source on the display device provide benefits that make the transfer of the aggregated information to the ultra-low power display device possible in a very efficient way. Second, at the next level or mid-level, the invention relates to a platform that overcomes the limitations of displaying predefined messages while presenting aggregated information. Third, at the top of the stack is the category of inventive concepts as they relate to an application to manage messages and their presentation on a device such as digital signage. This set of inventive concepts discloses effective ways to engage an audience with the aggregated information. It is to be understood that any of the three categories of inventive concepts may be put into practice independent of the other.

Embodiments of the invention may be implemented in numerous ways, including as methods, systems, devices, or apparatus. Several nonlimiting embodiments of the invention have been discussed above and are discussed below. Other aspects, features, and advantages of the invention will become apparent from the following detailed description taken in conjunction with the accompanying drawings, which illustrate, by way of example, the principles of the invention.

BRIEF DESCRIPTION OF THE DRAWINGS

FIG. 19 is a top view of a content source in a gliding box configuration according to an embodiment of the invention.

FIG. 20 is a front view of the gliding box configuration along an AA' direction in FIG. 19.

FIG. 21 shows a top view of a clamping connector and a display module according to an embodiment of the invention.

FIG. 43 shows XML data and schema to import fields according to an exemplary embodiment of the invention.

FIG. 51 shows a typical prior art multi-display setup, having independent links from video processor(s) or computer system(s) to each display in a multi-display setup.

FIG. 52 shows a platform that drives a multi-display module setup, which has a base display module connected to the platform according to an exemplary embodiment of the invention, with the base display modules and other ancillary display modules connected to each other serially, according to an exemplary embodiment of the invention.

FIG. 53 shows another platform that drives a multi-display module setup, which has a base display module connected directly to each ancillary display module according to exemplary embodiment of the invention.

FIG. 54 shows steps as to how and when a platform gets updated when new ancillary display modules are added according to an exemplary embodiment of the invention.

FIG. 59 shows an overview of components in a hardware platform used in accordance with an embodiment of the invention.

FIG. 60 shows engagement modes in accordance with an embodiment of the invention.

FIG. 61 shows the structure of an announcement in accordance with an embodiment of the invention.

FIG. 62 shows components of a display Signage engagement in accordance with an embodiment of the invention.

FIG. 63 shows components of a connected display engagement in accordance with an embodiment of the invention.

FIG. 64 shows a hierarchy within an engagement in accordance with an embodiment of the invention.

FIG. 65 shows a hierarchy within in another engagement in accordance with an embodiment of the invention.

FIG. 72 shows a 2×2 Pane Panel being used as announcement signage in accordance with an embodiment of the invention.

FIG. 73 shows a 2×2 Pane Panel being used as pricing signage and announcement signage in accordance with an embodiment of the invention.

DETAILED DESCRIPTION OF THE INVENTION

Figure 1:
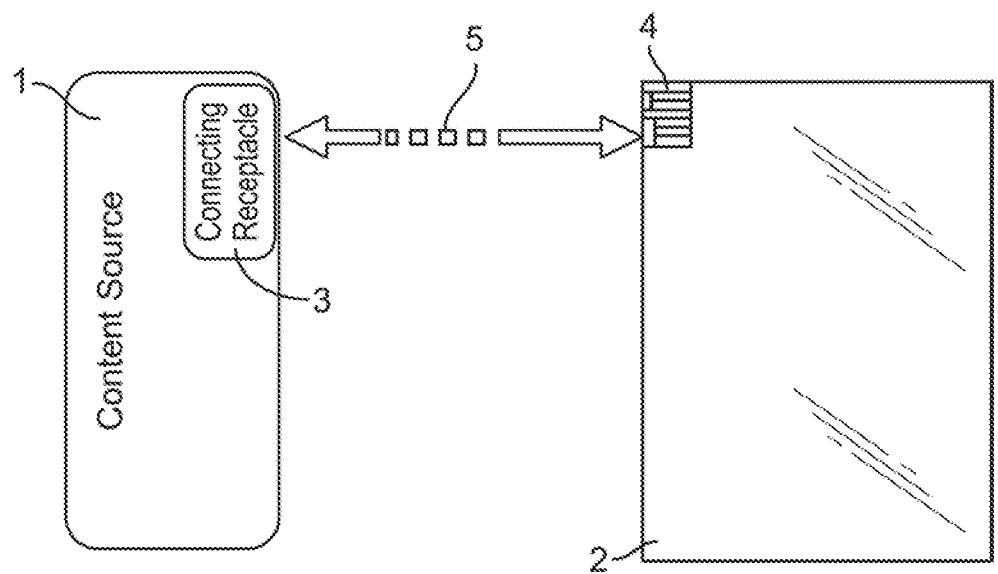
FIG. 1 shows components of a content source and a display module according to an embodiment of the invention

This application claims the benefit of U.S. Provisional Application No. 62/123,804, filed Nov. 28, 2014, U.S. Provisional Application 62/176,798, filed Feb. 27, 2015, and U.S. Provisional Application 62/178,958, filed Apr. 23, 2015, which are all hereby incorporated by reference in their entireties.

Transferring Content to a Display Module

In accordance with an embodiment of the invention, a programmed method is disclosed for the detection of one or more display modules or devices by a content source or system having access to a content source, and the efficient control and communication of the orientation, location, organization, and rendering of content for efficient transmission to display elements on the one or more display devices. As considered herein, the content source is a source device and the display module is a sink device. The term "programmed method," as used herein, is defined to mean one or more process steps that are presently performed; or, alternatively, one or more process steps that are enabled to be performed at a future point in time. The term programmed method contemplates three alternative forms. First, a programmed method comprises presently performed process steps. Second, a programmed method comprises a computer-readable medium embodying computer instructions, which when executed by a computer performs one or more process steps. Finally, a programmed method comprises a computer system that has been programmed by software, hardware, firmware, or any combination thereof, to perform one or more process steps. It is to be understood that the term programmed method is not to be construed as simultaneously having more than one alternative form, but rather is to be construed in the truest sense of an alternative form wherein, at any point in time, only one of a plurality of alternative forms is present.

As embodied and broadly described herein, the present invention provides a transient electrical coupling mechanism that enables the transfer of content, for example, media content, including but not limited to images, report(s), document(s), health information or card(s), ticket(s), maps, bar code(s), itinerary(ies), home and other sales listings, advertisements, "sticky notes," announcements, bedside shift report(s), etc., or any other information capable of being transferred from a content source to a display module or device for display thereon. The display module includes a coupling contact that is received for the transient electrical coupling by a connecting receptacle in the content source. The content is transferred to the display module via the transient electrical coupling of the coupling contact and the connecting receptacle.

Electronic paper (ePaper), electronic or electrophoretic ink (e.g., E Ink®), and the like are exemplary types of technology that may be used as a display element in the display module in accordance with embodiments of the invention. The ePaper and matrix-type electrophoretic display technologies, such as for E-Ink®, are very similar to the technologies of a matrix display, and like matrix displays, include a large array of pixels. The content transferred via the transient electrical and frictional coupling mechanisms described herein includes bitmaps or images, or it could be indexes to bitmaps or images stored on the display module itself. The firmware on the display module (described below), in conjunction with the circuitry native to the display element, prepares the data for display from the bitmaps or images. This data is then moved to the corresponding pixel locations addressed in the display element. In accordance with an embodiment of the invention, the processing element ((210—to be described later), will communicate with a display driver IC (such as ON Semiconductor's LC79451KB IC) on the display element. The display driver IC will accept commands and data from the processing element over a standard general purpose interface, such as SPI, or I$^2$C. The display driver IC will then generate signals with suitable voltage, current, timing, and demultiplexing to display the image received as data from the processing element that originated from the content source. Electrophoretic displays typically, have two sets of electrodes, column electrodes and pixel electrodes. To drive a particular pixel in a given row, the corresponding pixel electrode is activated by a row driver that supplies a row driving signal, which selects the given row of pixels, and the column driver supplies a column driving signal or data signals to the selected pixel in the row of pixels via the column electrodes. If a selection signal is active, the data signals corresponding to the data to be displayed and the selection signals together, provide a driving signal for driving the pixel selected. The display element may also be based on other display technologies, such as OLED, LCD, STN LCD, plasma display, LED, AMOLED, OTFT, TFT-driven OLED, and so on. Papers such as Braille Paper, Swell Touch paper and other specialty paper may also be considered for use as the display element.

FIG. 1 shows an exemplary embodiment of a content source (1) including a connecting receptacle (3) to receive a display module (2) including a coupling contact (4) according to an embodiment of the invention. A transient coupling mechanism (5), shown schematically in FIG. 1, enables the transfer of content from the content source (1) though the connecting receptacle (3) to the coupling contact (4) on the display module (2). Various embodiments of the connecting receptacle (3) allow the transient coupling mechanism to occur, which enables transfer of content to the display module (2). Data and control signals from the content source (1) passing through the connecting receptacle (3) provide the content that is transferred to the display module (2), so that the display module (2) uses it to refresh its display element. Other than content, data and control signals are transferred between the display module (2) and the content source (1) that may also include performance data, configuration data, program code, and monitoring parameter(s). The display module (2) may also provide data to or through the content source (1), such as user inputs and sensor data to the content source (1).

In other embodiments, access to the connecting receptacle (3) and the coupling contact (4) is a secure access. Details of the secure access in embodiments of the invention will be described below. Also, embodiments of the invention may include one or more switches or switching mechanisms, switching elements, detecting elements, or like mechanisms that are used for improving or helping to monitor the transient coupling mechanisms. These switches/mechanisms may be located inside the connecting receptacle (3) and may be implemented in many ways. For example, the switch or switching mechanism may include a miniature contact switch, a microswitch, or a surface-mounted or other type of light sensor-based switch. Other types of switching mechanisms would be contemplated by those skilled in the art. The switches or switching mechanisms will be described further below.

Figure 2:
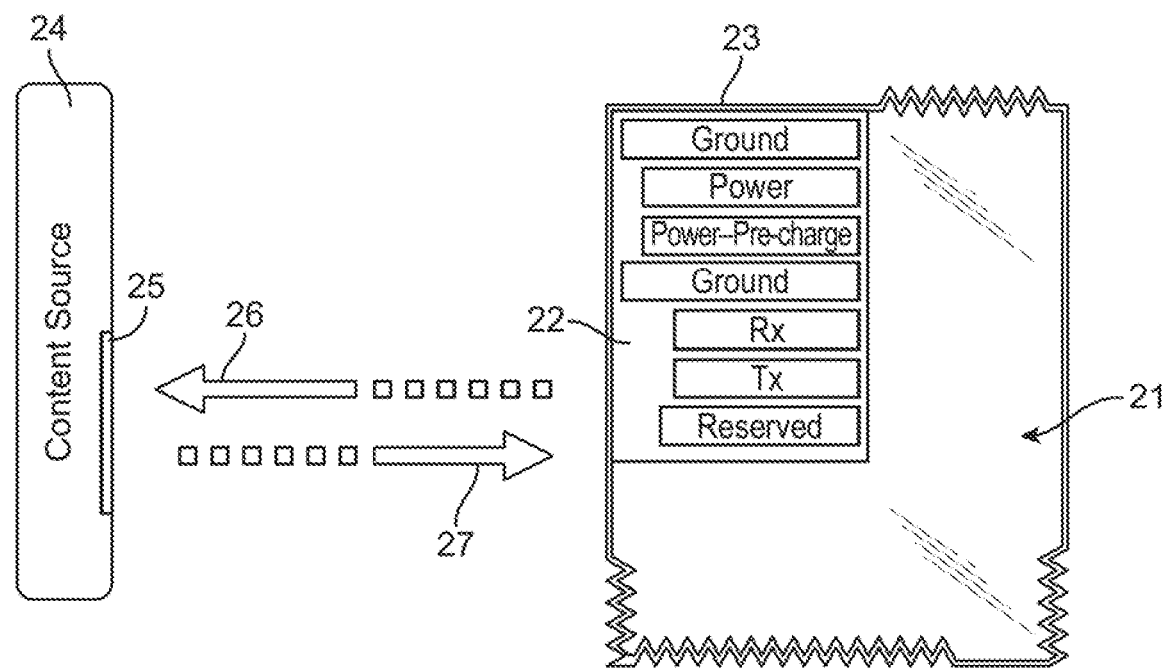
FIG. 2 shows a sliding connector and a display module according to an embodiment of the invention.

FIG. 2 shows a sliding receptacle (25) included in a content source (24) according to an embodiment of the invention. The sliding receptacle or connector (25) is an exemplary embodiment for the connecting receptacle (3) that is used along with a coupling contact or connector (22) in the display module (21) to facilitate a transient electrical coupling mechanism in accordance with an embodiment of the invention. The sliding receptacle (25) is also known as a sliding connector. The content source (24) includes content for display on a display module (21), which may include ePaper or the other types of display devices as the display element, as described above. The display module (21) is an exemplary embodiment of the display module (2). The connecting receptacle (3), in this case the sliding connector (25), is used to transfer content from the content source (24) to the display module (21) via the coupling connector (22) in the display module (21). The sliding connector (25) provides data signal, control signal, power, and ground paths to enable the transfer of content to the display module (21) when coupled to the content source (24). Details of how and when the transfer occurs will be described further below.

As shown in FIG. 2, the display module (21) also includes a module frame (23) near or along an edge or edges of the display module (21). Alternatively, the module frame (23) may be a layer of the display module (21) as described below. The module frame (23) is used to carry or include any special electrically conductive elements, traces (e.g., copper traces), wire or wires, lines, paths, or the like, or electrical or electronic components or similar elements for the display module (21). These elements may run near or along the edge or edges of the display module (21). The module frame (23) may also provide structural support, insulation, and protection for these elements and for a display element (not shown) of the display module (21), and for the display module (21) in general. The inclusion of any of the aforementioned elements or components in the display module (21) will depend on the requirements for the specific implementation. Although the traces may run on one or more sides or edges of the display module (21) in the module frame (23), they may also or instead run outside the module frame (23), as would be required after taking into consideration design optimization and cost reduction purposes. The material characteristics and structure of the module frame (23) will depend upon the particular display technology used in the display module (21). In certain embodiments, the module frame (23) is not included in the display module.

The display module (21) typically is a layered structure, i.e., it constitutes multiple layers of materials. Each layer has a specific purpose or function. For example, various layers may include materials that provide insulation, color filter(s), protection material, and/or optical sheets, as would be understood by one of ordinary skill in the art. The layers may also include host-to-data driver circuitry, integrated sensors, or other components. The number of layers and the layer details depend upon the specific display technology used in the display module (21). The module frame (23) may also be one such layer. In certain embodiments, the module frame (23) may be a structural frame near the edge, and the circuitry or elements typically considered for the module frame (23), as described above, may be placed in one or more added layers. This added one or more layers is used to carry and may provide insulation and protection for any special electrically conductive elements for the display module (21) similar to what was described above.

The content transfer via the transient electrical and frictional coupling mechanisms will now be described in more detail. The content transfer occurs while the coupling contact (22) of the display module (21) is slid into the sliding connector (25) (referred to as "slide in" (26)), or it occurs while sliding the coupling contact (22) out from the sliding connector (25) (referred to as "slide out" (27)) after the coupling contact (22) was already slid into the sliding connector (25). The display module (21) with the coupling contact (22) is slid into and slid out from the content source (24) by a user or by an automatic feeder mechanism or machine. During slide in (26) or slide out (27), the coupling contact (22) transiently electrically couples with the sliding connector (25) as the coupling contact (22) is moving and making sliding electrical and frictional contact between corresponding electrically conducting pads, pins, traces, wires, lines, or the like inside the coupling contact (22) and the sliding receptacle (25). The display module (21)'s display element (not shown) gets updated by the content that is transferred during this slide in (26) or slide out (27) transient electrical coupling or contact, and the content is then ready for viewing on the display module (21) by a user.

In certain embodiments, a switch (2002) (shown in FIG. 23) may be included in the sliding receptacle (25) that is activated during the slide in (26) or slide out (27) process or activated as these processes are about to occur. The switch (2002) functions to improve reliability by, for example, activating a visual (e.g., LED), audible (e.g., buzzer or beep) alert (provided on or by the content source (24) or the display module (21)) to the user indicating that good sliding electrical coupling or contact has been established between the pads, pins, traces, wires, lines, or the like inside the coupling contact (22) and the corresponding ones inside the sliding receptacle (25) during slide in (26) or slide out (27). The switch (2002) may be located elsewhere inside the sliding receptacle (25), and not necessarily between PWR and RX pads shown in FIG. 23. The switch (2002) typically will be activated while ground and power paths are transiently slidingly (and frictionally) established, or as they are about to be established. After the switch (2002) is activated, during the sliding, the data and control sliding electrical conductive paths between the coupling contact (22) and sliding receptacle (25) will be established between the corresponding pads, paths, pins, wires, lines, traces, or the like of the coupling contact (22) and the sliding receptacle (25). During this sliding electrical contact the data signals and control signals, which provide the content, are transferred to the display module (21) from the content source (24). The switch (2002) preferably is included in the content source (24), and will be described further below with respect to FIG. 23.

Figure 5:
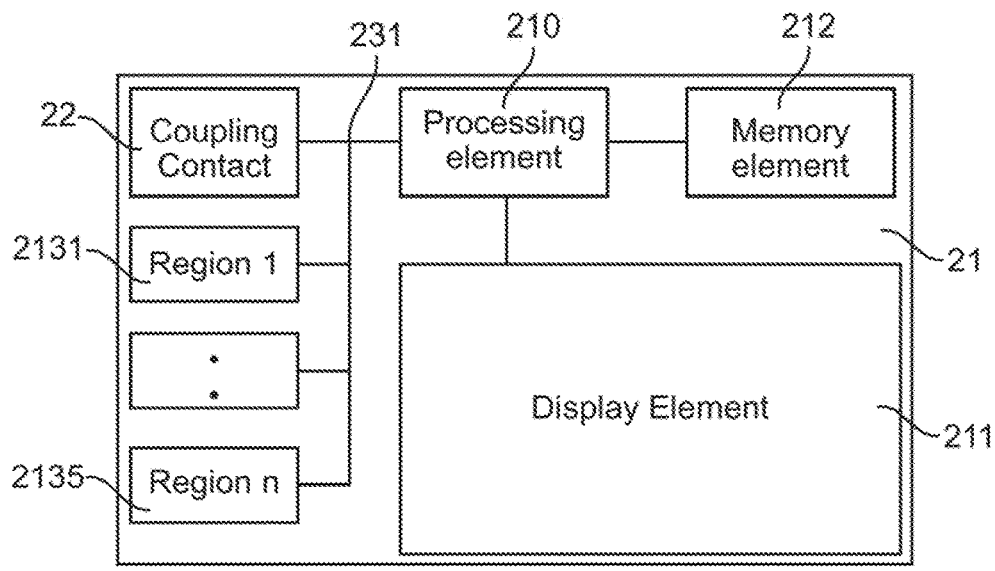
FIG. 5 is a block diagram of a display module including a coupling contact, various specific functional regions, and other components according to an embodiment of the invention.
Figure 7:
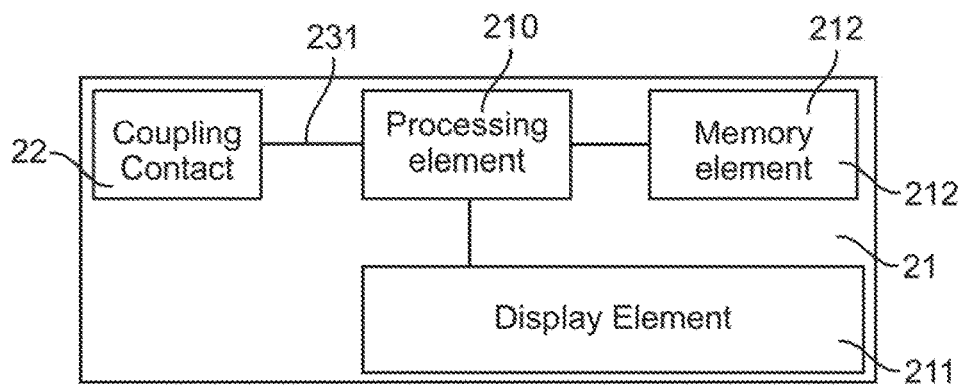
FIG. 7 is a block diagram of a display module including a coupling contact without various specific functional regions according to an embodiment of the invention.
Figure 26:
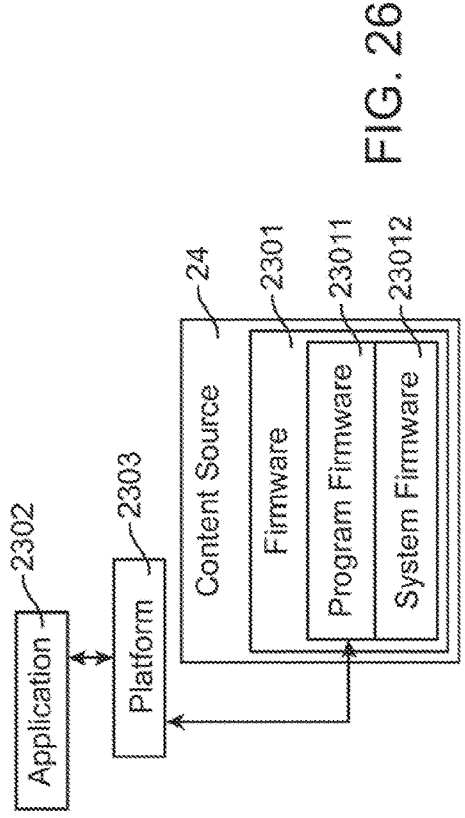
FIG. 26 is a block diagram of a content source's firmware and how it interacts with other components in the system according to an embodiment of the invention.

The switch (2002) is not necessarily required if appropriate firmware (2301) (see FIG. 26) is provided in the content source (24). The firmware (2301) may also detect the insertion of the display module (21) when the coupling contact (22) is inserted into the sliding receptacle (25). This firmware (2301) manages the interaction of the content source (24) with the display module (21). In FIG. 26, the firmware may include (i) system firmware (23012), which is the OS, drivers, and various low level system services, and (ii) program firmware (23011), which manages and controls the various functions of the content source (24), including the transfer of content to the display module (21). The program firmware (23011) also communicates to a platform (2303) like the platform described above. The program firmware (23011) further communicates either indirectly through the platform (2303) or directly with an application (2302) like the application(s) described above. In some embodiments, the application (2302) and the platform (2303) reside outside the content source (24). In other embodiments, the application (2302) and the platform (2303) reside in the content source (24). The display module (21) may also include a processing element (210) (as shown in FIGS. 5 and 7), which also hosts firmware, referred to as program code.

As described above, in certain embodiments, when the coupling contact (22) in the display module (21) is slid into the sliding receptacle (25) (slide in (26)), the transient electrical and frictional coupling paths for ground and power are established. Once this occurs, the program firmware (23011) is notified by the system firmware (23012) that the display module (21) is about to complete its slide in (26) or slide out (23012). The program firmware (23011) scans for details of the display module (21). After the ground and power transient electrical couplings are established, Rx (225) and Tx (226) pins (shown in FIG. 3) (may also be pads, traces, wires, lines, or the like, or other types of electrically conducting paths other than pins) make sliding electrical and frictional contact with corresponding electrically conducting pin receptacles (may also be pads, traces, wires, lines, or the like, or other types of electrically conducting receptacles other than pin receptacles) in the sliding receptacle (25), and then initialization takes place and content transfers by the slide in (26) or slide out (27).

In some embodiments that include the switch (2002), the switch (2002) includes a key (20024) (shown FIG. 23) that may be mechanically pressed or engaged by a portion of the coupling contact (22), for example a bump, tab, extension, edge, or the like, that is part of the coupling contact (22) (not shown), or another portion of the display module (21), as slide in (26) (or slide out (27)) is occurring or is about to occur. After the initialization, the display module (21) identifies itself to the program firmware (23011) in the content source (24). Depending on the type of display module (21), communication may then take place between the content source (24) and the display module (21). During this communication, the content source (24) may also provide visual and/or audio feedback to the user, e.g., assuming a user is sliding the display module in and out of the content source (24). The content source (24) then transfers the content to the display module (21) during this slide in (26) (or slide out (27)). Once the transfer is complete during slide in (26), the visual and/or audio feedback may change to indicate that the user may slide the display module (21) out of and remove it from the sliding receptacle (25), which may be within a slot (111) (shown in FIG. 12) that allows access to the connecting receptacle (3) or (25) within the slot (111). Similarly, if content is transferred during slide out (27), the visual and/or audio feedback may be provided to indicate that the user may continue to slide the display module (21) out and remove it from the sliding receptacle (25).

For the embodiments discussed so far, the connecting receptacle has been referred to as a sliding connector. In other embodiments, the connecting receptacle will be referred to as a gliding connector, a resting connector, or a clamping connector. Moreover, although the previous description mentions slide in (26) and slide out (27), how the firmware operates may be similar for all types of connections that are discussed herein, such as sliding, gliding, resting, and clamping. The gliding, resting, and clamping connections will be described further below.

Figure 3:
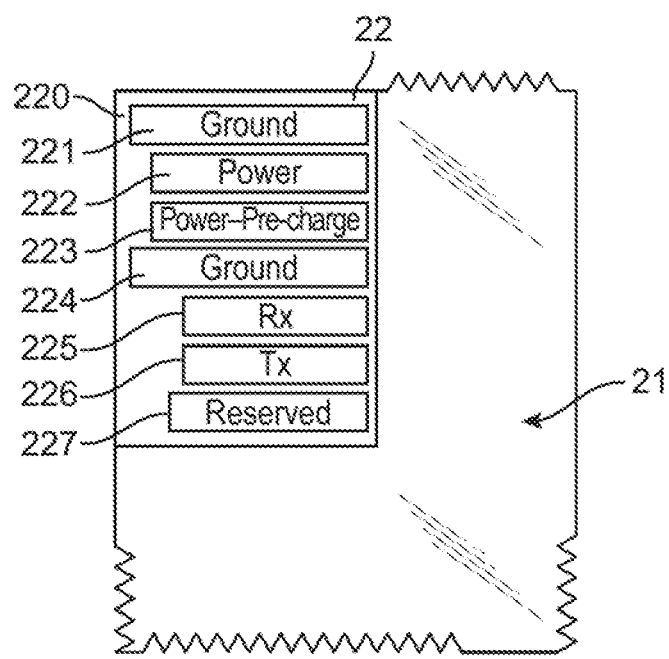
FIG. 3 shows top view of a coupling contact with labeled pins according to an embodiment of the invention.
Figure 18:
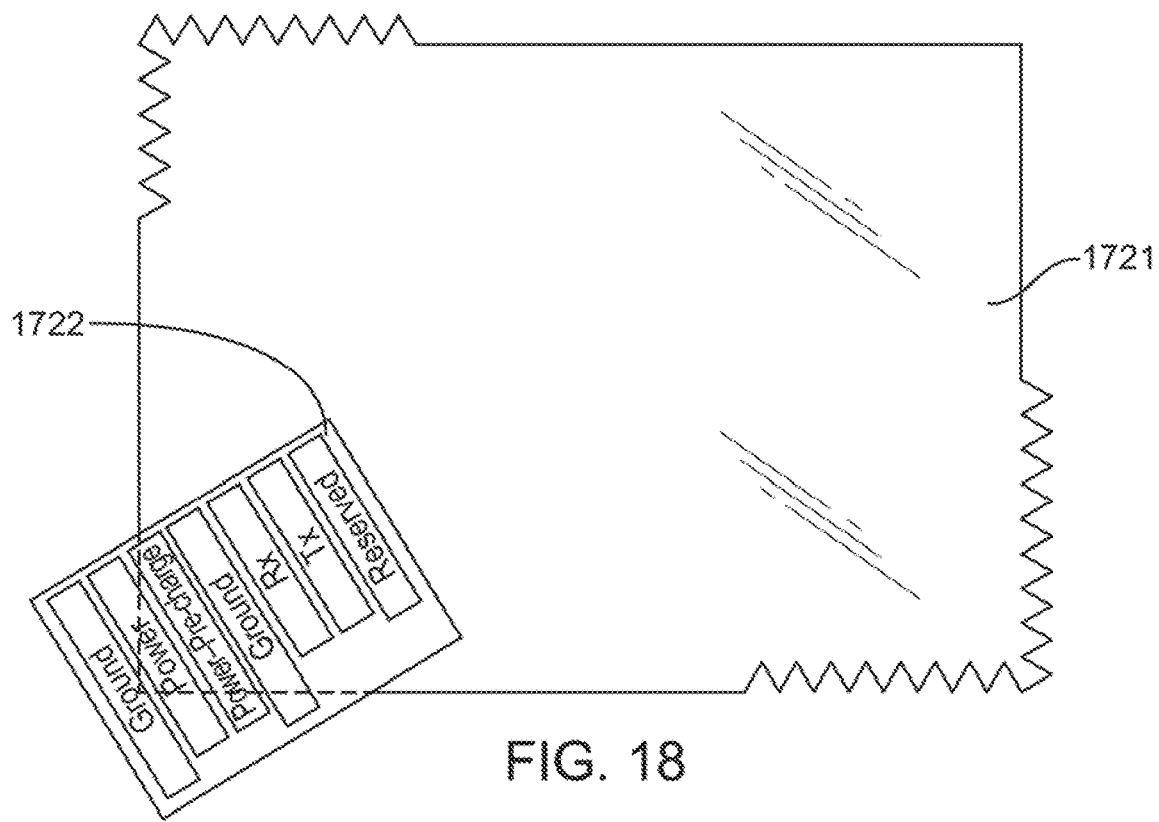
FIG. 18 is a top view of a display module with an obliquely positioned and protruding coupling contact according to an embodiment of the invention.

In FIG. 3, the coupling contact (22) includes a mask (220) and a set of pins (221, 222, 223, 224, 225, 226 and 227) (or pads, traces, wires, lines, etc., or other electrically conductive paths, as previously discussed). The coupling contact (22) may be located along the edge of the display module (21) or it may be located such that it protrudes out of the display module (21), for example as shown in the embodiment of FIG. 18, although other embodiments having the coupling contact (22) protrude from various other possible locations along the edge of the display module (21) are contemplated. The mask (220), a particular embodiment of which is shown in FIG. 3 along with the pins, is on the back side of the display module although it could be on the front side (i.e., the side with a display element such as display element 211 shown in FIGS. 5 and 7). The display element (211) may be, for example, ePaper, or the like, as described above. The mask (220) maybe within or part of the module frame (23). The mask (220) protects the underlying active traces and trace elements, for example, pins or copper traces, from oxidation and prevents bridges from forming between the closely spaced pins. There can be any number of pins corresponding to signals required for the particular embodiment. What is shown in the embodiment of FIG. 3 are exemplary pins. The pins are used to receive the content via data signals and control signals, and for providing transient electrical and frictional coupling power and ground paths for the display module (21) from the content source's (24) sliding connector (25), as previously described. The number of pins required depends on various factors, such as the type of display module (21), the amount of data to be transferred, and various features supported on the display module (21). In the embodiment shown in FIGS. 2 and 3, two grounds pins (221) and (224) are provided. There generally is a ground pin for each supplied voltage. In this embodiment, a single voltage may be supplied for a power pin (222), although other numbers of voltages, power pins, and corresponding ground pins are possible.

In certain embodiments, some of the pins (221-227) may be of uneven length. This ensures that a specific mating order can occur between the pins in the coupling contact (22) and the corresponding transiently electrically conducting pin (or pads, wires, lines, traces, paths, or other types of) receptacles in the connecting receptacle (3) or sliding connector (25) as they make or are about to make sliding and frictional electrical contact during slide in (26) or slide out (27). The ground pins (221) and (224) are the longest of all the pins, and are the first to make contact with their corresponding pins, though they may not be of the same length. Regardless of their relative lengths these ground pins (221, 224) are followed in length by the next longest length power pin(s) (222) and power pre-charge pin(s) (223), if included. The power pin (222) and power pre-charge pin (223) may or may not be the same length. The point is that a transient electrical and frictional ground is first established for the display module (21) before making any transient electrical and frictional power connections for applying power from the content source (24) via the power connection pins, such as power pin (222) and power pre-charge pin (223), to the display module (21). Having the ground pins always transiently and frictionally contact first will establish electrostatic equilibrium across the content source (24) and the display module (21). Another benefit of this multi-step mating process is that it would avoid possible arcing of the power connector contacts.

The display module (21) may use its power pins to charge internal bypass capacitors to dampen any AC or noise present at all or some frequencies. Some embodiments may include additional power pins in the display module (21) and corresponding pin receptacles in the connecting receptacle (3) or sliding connector (25) from which other circuitry in the display module (21) uses or manipulates one or more of the corresponding supplied voltages. Including the power pre-charge pin (223) may also aid in controlling the rise of the system voltage during power up.

Figure 24:
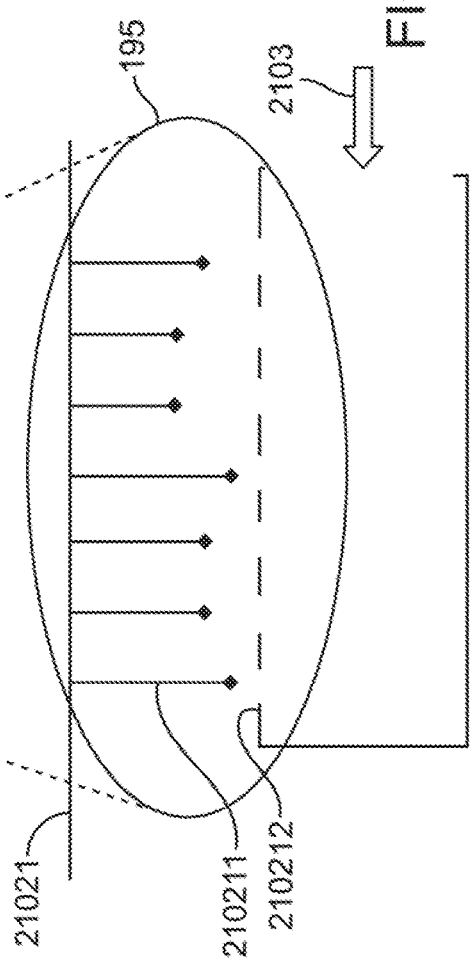
FIG. 24 is a top view of a clamping connector according to an embodiment of the invention.

Based on an encoding scheme, supported by both the content source (24) and the display module (21) in this embodiment, the data signals and control signals will be transiently electrically and frictionally transferred between the content source (24) and the display module (21) over two or more pins, e.g., Rx (225) and Tx (226) on the display module (21) side, as shown in FIG. 3 and FIG. 24. The Rx (225) pin receives data and control signals from the content source (24) and the Tx (226) pin provides any data from the display module (21) to the content source (24), if included. These pins may be of the same length, but shorter in length than the ground, power, or power-recharge pins.

When the application (2302) and/or platform (2303) have data to be sent to the display module (21), the data is sent to the content source (24). The content source (24) processes the data and sends the processed data over its connecting receptacle (25) to the display module (21)'s coupling contact (22). The display module (21)'s coupling contact (22) receives the processed data at its Rx Pin (225). The data processing on the content source (24) and the display module (21) are symmetric and related, e.g. if the data serialized on the content source (24) then an equivalent de-serialization of the data takes place on the display module. Also, the display module (21)'s coupling contact (22) transmits data to the application and/or platform (through the content source (24)'s connecting receptacle (25)) at the coupling contact (22)'s Tx Pin (226). The same type of data handling would occur for all disclosed embodiments of the content source and the display module.

Figure 27:
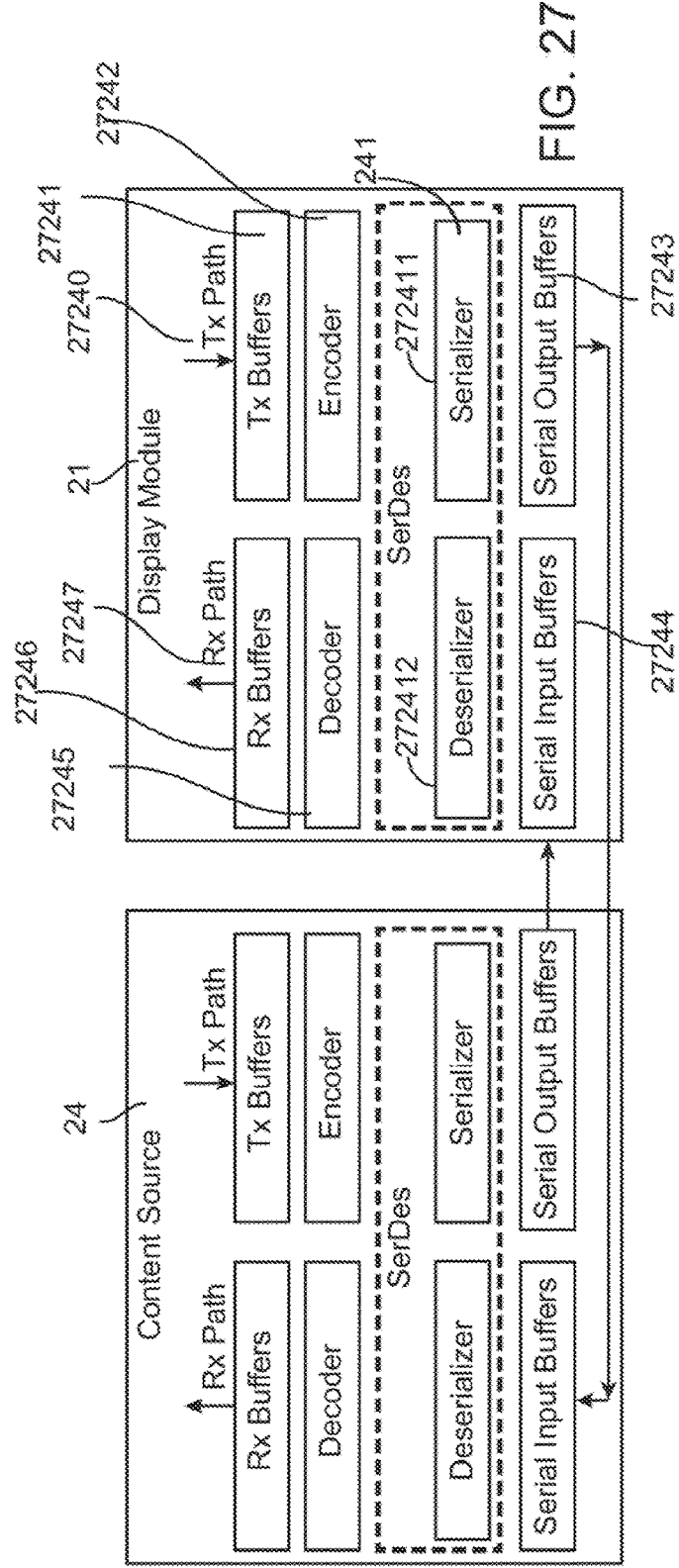
FIG. 27 is a high level block diagram of data/content transfer between a content source and a display module according to an embodiment of the invention.

In a preferred embodiment, the Rx/Tx pins may work in conjunction with a SerDes (serializer/deserializer) or similar function block (241), as shown in FIG. 27. When serialized data, which prior to serialization had been processed by the platform and/or application, is received at the display module (21)'s Rx Pin (225) from the serial output buffers of the content source (24), it is passed to serial input buffer (27244). The received data is then deserialized by the deserializer (272412) and made available to a decoder (27245). The decoder (27245) then unpacks the deserialized data. Then it is temporarily stored in Rx buffers (27246) before moving down the Rx path (27247) for use by the firmware resident in the display module (21). Also, when Tx buffers (27241) receive data from the resident firmware over Tx path (27240), the data received is passed to the encoder (27242). The encoder (27242) then processes the incoming data stream from the Tx buffers (27241) by mapping the data stream to a pre-defined bit pattern that is more suitable for serialization by the serializer (272411). When the serialized data is ready to be sent out to the content source (24), it is temporarily stored in serial output buffers (27243) before being sent out over the Tx pin (226) to serial input buffers of the content source (24). A similar arrangement exists on the content source (24), as shown in FIG. 27, where data received from the display module (21) is processed for use by the platform and/or application on the content source (24).

There may also be multiple Rx/Tx pins, pads, paths, lines, wires, traces, etc. that carry wide bit-width signals. In other embodiments, data signals and control signals may be transferred over pins with different encoding schemes, such as pins that form D+ and D− pairs in the coupling contact (22) (as in typical differential signaling) along with corresponding pin receptacles in the connecting receptacle (3), sliding connector (25), gliding connector (75) (shown in FIG. 9), resting connector (95) (shown in FIG. 10), clamping connector (195) (shown in FIG. 21), or other connectors, as has been or will be described in more detail herein. In yet other embodiments, multiple pairs of such pins and pin receptacles may be provided for transiently electrically and frictionally coupling for transferring data signals and control signals, such as for I/O and clock.

A reserved pin (227) may be included for certain purposes. One exemplary purpose is that only when this pin is held high will the display module (21) refresh with power applied. In embodiments that have multiple display modules, some of which will be described below, this will prevent the display modules from refreshing simultaneously because too much power or current may be otherwise drawn. Also the display elements may have to be selectively refreshed on only one or more particular display modules, but not on all the connected display modules. The reserved pin (227) may also be pulled low by the display module (21) to indicate activity to give feedback to a user through an LED light or signal, such as a beep or alert, on the display module (21) or on the content source (24). In other embodiments, there may be one or more reserved pins (227), each dedicated for one or more tasks, depending on the specific implementation. In other embodiments, there may be no reserved pin(s) (227).

It should be understood that having different length pins, as described above, ensures that when the coupling contact (22) is slid out from the coupling receptacle (3), sliding connector (25), or other connectors described herein, the switch becomes deactivated (e.g., as the key (2002) moves back to its normal or unpressed (i.e., deactivated) position and is no longer engaged by a portion of the coupling contact (22)), and the data signal and control signal transfers terminate. Then the power is removed and finally the ground path is decoupled and all the pins in the coupling contact (22) are no longer in sliding contact with the corresponding pin receptacles, traces or the like in the coupling receptacle (3) or sliding connector (25) or other connectors described herein.

In certain embodiments, the pins may be rectangular-shaped in cross section. In alternative embodiments the pins may be round-edged rectangular-shaped, cylindrically shaped or they may be raised pins, bumps, protrusions, or wires, lines, traces, or any other shape or any other electrically conductive connector as would be understood by a person of ordinary skill in the art. In one such alternative embodiment, the coupling contact (22) may not have a pin or any contact of any kind. In these embodiments the connecting receptacle (3), sliding connector (25), or other connectors described herein may be modified to communicate with the display module (21), or different hardware may be used to function like the connecting receptacle (3), with a corresponding modification of, or change in the hardware that functions like the coupling contact (22) to instead provide for contactless coupling. For example, the coupling mechanism may be made contactless for the transfer of content by using electromagnetic wave coupling, as would be understood by a person of ordinary skill in the art. In this case, the display module (21) has to be in proximity to the modified version of, or different hardware for, the connecting receptacle (3) up to and including, e.g., 50 millimeters, to receive the content and control signals. In such a contactless embodiment, the display module will have a power source, such as a battery in a power source region, as described below, and the associated circuitry, as well as a provide its own ground. The electromagnetic wave coupling would be used to transfer the data and control signals to the display module (21). In accordance with an embodiment of the invention, the display module may have NFC (Near-Field Communications) technology as an example technology to enable the electromagnetic wave coupling.

Further description is now provided for the coupling contact (22). The coupling contact (22) may be inside a sleeve (not shown), which may be an electro-mechanical sleeve, to protect it from damage. Such a sleeve may be similar in form and/or function to the type of sleeves that have been used on floppy disks, as would be appreciated by a person of ordinary skill in the art. The sleeve will be mechanically moved or unlocked by a tab, protrusion, or the like located in the coupling receptacle (3), sliding connector (25), or other connector described herein, or in a corresponding slot to expose the pins in the coupling contact (22) to establish transient electrical coupling for the slide in (26) or slide out (27) operation, as described above. As a form of security, the electro-mechanical sleeve may also only open if adequate security authentication measures are met, such as those that will be described below. In this case, an electrical or electronic signal in the display module (21) will be required to open the electro-mechanical sleeve upon proper authentication or authorization. There may be other reasons to include the sleeve, such as for decoration and style. Alternatively, if security measures are not required, the electro-mechanical sleeve may also open upon activation by an electrical or electronic signal in the display module (21).

Figure 4:
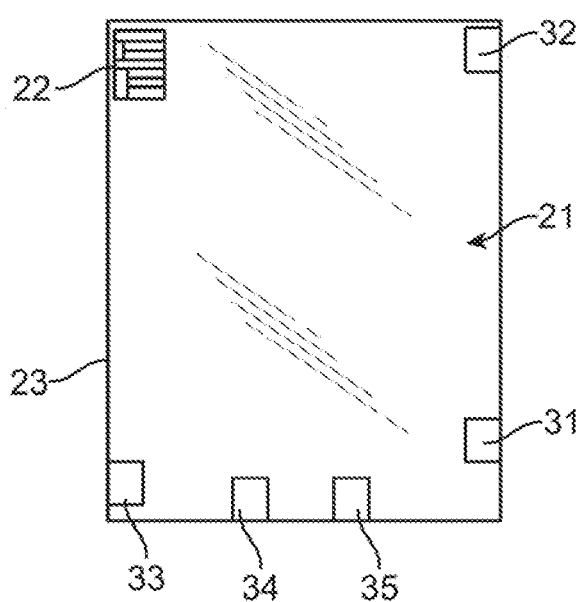
FIG. 4 shows a top view of a display module with a coupling contact and various specific functional regions according to an embodiment of the invention.

FIG. 4 shows the display module (21), the coupling contact (22), the module frame (23), and regions of circuitry, some of which are AuthNZ (authentication/authorization) region (31), UO (user output) region (32), PS (power source) region (33), connectivity region (34), and SI (secure-ID) region (35). The display module (21) may include these and perhaps other regions of circuitry that are dedicated for different tasks. These regions may be integrated to form one or more composite regions. In certain embodiments the display module (21) may have less or more than these five regions, and some may be duplicates of the others or serve other purposes. For example, only the PS region (33) may be included. Although particular locations are shown for the regions (31-35) in FIG. 4, any of these regions or other regions dedicated for different tasks may be located anywhere on the display device, depending on the particular embodiment or needs of the display module (21). Even with these regions of circuitry it is expected that the display module (21) would retain the advantages described above, i.e., remain lightweight, have only the minimum amount of added circuitry needed, and still maintain reduced resource requirements.

The AuthNZ region (31) includes a sensor to accept user input for the purposes of Identification (authentication—AuthN) and/or access control (authorization—AuthZ). If this region has AuthN functionality, then the display module (21) relies on the content source (24) to identify the user to transfer appropriate content. If this region has the AuthZ region, then the display module (21) relies on the content source (1) to verify the rights of the user to access the content to be transferred. The task of analyzing the data captured by the sensor in the AuthNZ region will be performed at the content source (1). Such security could involve passwords, pin codes, or other techniques of identification known to a person of ordinary skill in the art using hardware and/or software. The technique may instead be biometric. An affirmative authentication or verification result, when based on the inputs obtained at the AuthNZ region (31), confirms that the user has authorized access to the content that is about to be transferred to the display module (21). An exemplary biometric sensor for the AuthNZ region (31) may be a finger print reader. In this case, the finger print reader may be located on the back side of the display module (22) (i.e., on the opposite side of the display module (21) from the display element, such as the display element 211 shown in FIGS. 5 and 7). The AuthNZ region (31) may be located anywhere on the display module (21), and it may be implemented using other techniques, such as a skin conductance sensor, touch sensor, or other biometric sensor, or other input devices. The AuthNZ region (31) may be electrically connected directly or indirectly over traces (e.g., copper traces), wires, lines, or other electrically conductive apparatus to the coupling contact (22). These traces may run through the module frame (23). In alternative embodiments, an AuthNZ region, such as a finger print reader, may be located on or in the content source (1). In this case, for example, when the user is sliding the display module (21) into the content source (1), the user's finger (e.g., an index finger) may be placed on the AuthNZ region (31) for authentication/authorization. The AuthNZ region, when part of the content source (1), also may be implemented using the other techniques described above. When the AuthNZ region is part of the content source (1), it is electrically connected, directly or indirectly, to the receptacle pins in the coupling receptacle (3), sliding connector (25), or other connector described herein.

The UO region (32) (user output region) represents a region where a transducer is provided that converts electrical or electronic signals in the display module to output either an audible, visual, haptic (e.g., vibration) alert, or a combination of such indicators. The output may indicate that a read operation of the content transferred is incomplete, or that the display element will be erased, or that slide in (26) or slide out (27) has not occurred properly, or that the battery (described below) charge is low, or provide other information to the user regarding the status of the display module, or that authentication/authorization is unacceptable, for example, a finger print is unacceptable, etc. The UO region (32) may be connected directly or indirectly over traces (e.g., copper traces), wires, lines, or other electrically conductive paths to the coupling contact (22). Those electrically conductive paths may run through the module frame (23).

The PS region (33) (power source region) represents a region where a power source element exists. A thin battery is an exemplary power source, e.g., a rechargeable battery. The power source is meant for tasks that require manipulation/use of the display module (21) when it is not coupled to the content source (1). The PS region (33) may be electrically connected, directly or indirectly, to other circuitry in the display module (21) and to the coupling contact (22) over copper traces, wires, lines, or other electrically conductive paths. Those paths may run through the module frame (23). The PS region (33) may also be used to drive other regions in the display module (21), as will be described below. Power/voltage(s) to these other regions may alternatively be provided by the content source (1) or another source through the coupling contact (22) when coupled to the coupling receptacle (3), sliding connector (25), or any other connector described herein.

The connectivity region (34) represents a region that includes circuitry to establish a network connection with either the content source (24) or another display module (21). An exemplary connectivity may be established using RFID technology, such as near field communication (NFC), for short bursts of data transfer, as would be understood by a person of ordinary skill in the art. Exemplary short bursts of data may include data for identifying (see below) the particular display module (21) to the content source (24) or to other display modules (21), or to a smartphone. In other embodiments the particular display module (21) may also receive data. For such RFID technology to be supported, if configuring data is required, then that data would previously have been made available during the transient electrical coupling. Other types of connectivity will be apparent to a person of ordinary skill in the art.

The SI (secure-ID) region (35) represents a region that includes circuitry to store a secure identification that is associated with the display module (21) to identify the particular display module (21). An exemplary device that may be included in the SI region (35) is a serial number chip, as would be understood by a person of ordinary skill in the art. The serial number chip will enable the display module (21) to be identified by the content source (1) in a secure and tamper-resistant way.

The display module (21) may have other regions based on other sensors for functions not specifically listed herein. Such functions may be understood by a person of ordinary skill in the art. Such sensor regions may include a proximity sensor region, which allows the display module (21) to detect that it is about to be picked up. Another region may include a composite region, which consists of a memory bank region and an UI (user input) region. The memory bank region includes additional memory which allows storing of additional screen-sized images (as in multiple pages). The UI region may have two touch sensors, one touch sensor that allows a user to navigate to the next page and the other touch sensor to go back to the previous page. Such a composite region will allow navigation across the multiple pages stored in the display module (21).

As shown in FIG. 5, the display module (21) may include a processing element (210) directly or indirectly electrically coupled to the coupling contact (22) and to the other components of the display module (21). The processing element (210) may be a microcontroller or in certain embodiments it may be a microprocessor or an application specific integrated chip (ASIC), or similar integrated chip. A typical microcontroller may be Microchip's 8-bit PIC MCU. The purpose of the processing element (210) is to manage the I/O at the coupling contact (22). The processing element (210) also may use the content received from the content source (24) through the coupling contact (22) to display it on the display module (21)'s display element (211). A memory element (212) may be used to store data and/or control signals that facilitate the I/O with the connecting receptacle (3), sliding connector (25), or other connectors described herein, and also program code for the processing element (210). A non-limiting example of a memory element includes non-volatile storage such as FLASH or other non-volatile random access memory, another data storage system, or a combination thereof. The memory element may also include random access memory such as DRAM or SRAM or other volatile storage, to cache the non-volatile storage and also to store data used by the processing element (210). There are various regions (2131-2135), which may be the same as the regions (31-35) described above that are directly or indirectly electrically coupled to the coupling contact (22) and to the processing element (210) over an internal bus (231). The physical traces, wiring, or other electrical conductors to support the internal bus may be included in the module frame (23). The computing power of the processing element (210) and the capacity of the memory element (212) coupled directly or indirectly to the processing element (210) will depend upon the kind of display technology used in the display module (21) and also on the types of regions, for example, the regions (2131-2135 or 31-35), that are available in the display module (21). The internal bus (231) electrically couples, directly or indirectly, the coupling contact (22) and the processing element (210) to each other. The mechanism to couple the display element (211) to the processing element (210) depends upon the display technology, and the details of the display element (211) also depend upon the display technology being used. The display element (211) may be ePaper, electronic or electrophoretic ink, such as E Ink®, or the like, as described above.

Figure 6:
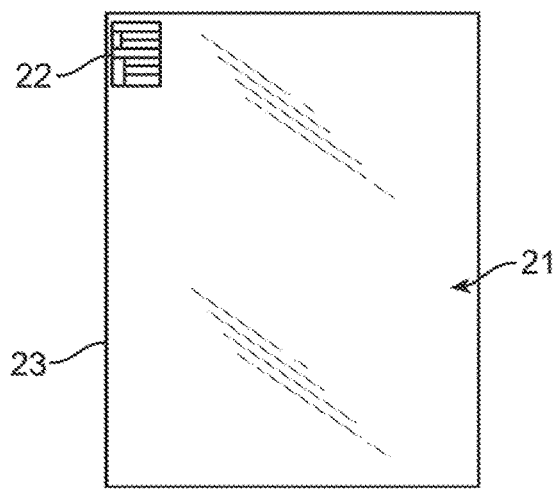
FIG. 6 is a top view of a display module including a coupling contact without various specific functional regions according to an embodiment of the invention.

FIG. 6, shows an embodiment of a simplified version for the display module (21), which includes the coupling contact (22) and the module frame (23). The display element also is included, although not shown in FIG. 6. The display element typically would be located on the same side of the display module (21) as the coupling contact (22) (i.e., the front side, which is the user viewing side of the display element, i.e., the direction facing out from the page of FIG. 6). It could instead be located on the side opposite to that where the coupling contact (22) is located (i.e., on the back side, which is the direction facing out from the back of the page of FIG. 6). FIG. 7, shows an embodiment of a simplified version for the display module (21) otherwise similar to the description of FIG. 5, but without the regions (2121-2135) described above.

Figure 8:
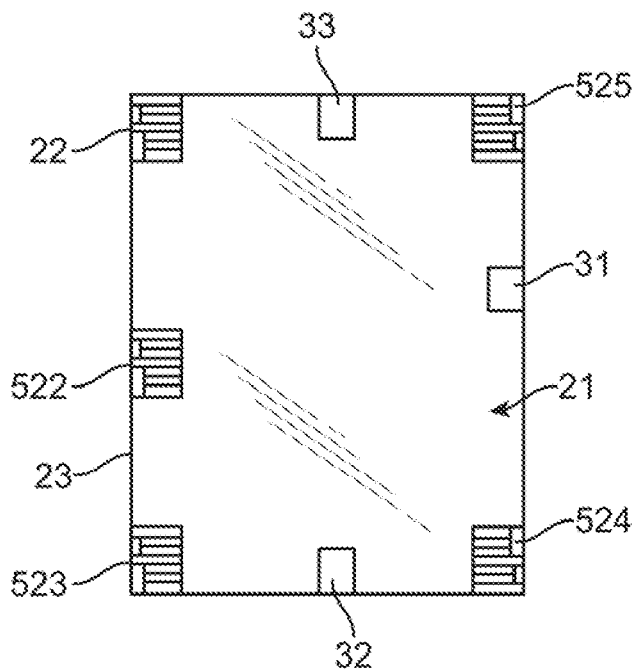
FIG. 8 is a top view of a display module showing exemplary locations where coupling contacts and various other specific functional regions and components may be located in the display module according to an embodiment of the invention.

FIG. 8 shows the coupling contact (22) at or near a corner and along or near the edges of the display module (21). It may be located anywhere on the display module (21) in other embodiments, but preferably at, along, or near an edge(s) or a corner (e.g., at the locations shown for coupling contacts (522, 523, 524, or 525)) of the display module (21). The coupling contact (22) may be either on the front side (i.e., the side having the display element 211 shown in FIGS. 5 and 7) or on the back side (i.e., side on the opposite side from the display element (211)) of the display module (21). Similarly, the regions (31-35 or 2131-2135) may be located anywhere on the display module (21). Each region may be located either on the front side or on the back side of the display module (21). These regions may instead or also be located in interior layers of the display module. In such an embodiments, the one or more interior layers may be packed between other layers of the display module. Various embodiments of the display module (21) may have one or more coupling contacts (22) (e.g., the coupling contacts (22, 522)), no or one AuthNZ region (31), no or one UO region (32), no or one PS region (33), no or one connectivity region (34), no or one SI region (35), or there may be some other combination or numbers of these regions besides none or any one of these regions (e.g., more than one of the same type of region may be included). When it has one or more coupling contacts (22, 522) only one contact can be used at any particular time for transferring the content from one content source (24). Multiple coupling contacts (22) will improve the display module's (21) usability with various numbers and types of content sources (24).

Figure 9:
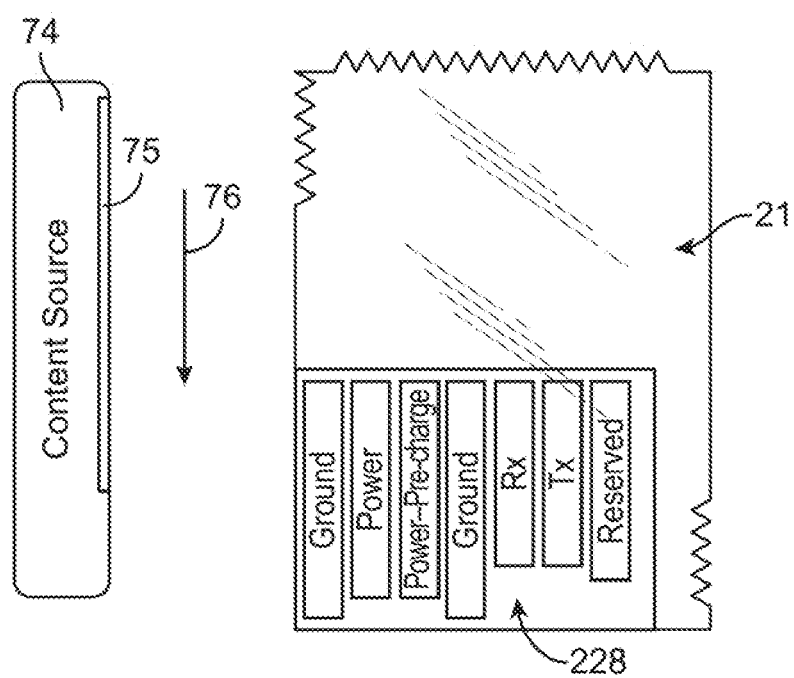
FIG. 9 shows a gliding connector and a display module according to an embodiment of the invention.

FIG. 9 shows more details for a gliding connector (75), briefly mentioned above, which is another exemplary embodiment for the coupling receptacle (3) that may be used to transfer content from a content source (74) to the display module (21). The term gliding connector and gliding receptacle may be used interchangeably. The content source (74) is similar to the content source (24) except for including the gliding receptacle (75) and how it is used to transfer content, as described below. The gliding receptacle (75) similarly carries data signals and control signals, and establishes power and ground to enable the transfer of content to the display module (21). The pin receptacles in the gliding receptacle (75) are similar to the pin receptacles in the sliding coupling receptacle (25). "Gliding" is somewhat analogous to the motion of a credit card being slid through a credit card magnetic stripe reader. This gliding embodiment uses a transient electrical coupling and transfer of content mechanism similar to that described above for the sliding embodiments but with changes in the structure/orientation of the various electrical contacts, pins, traces, etc. compared to the sliding connector (25) to accommodate the gliding motion. The changes specific to the gliding receptacle (75) due to a "gliding" (76) operation or motion performed to transfer content may be, for example, that the pins in the gliding receptacle (75) are rotated (e.g., by 90 degrees) relative to the pins in the sliding connector (25). This will accommodate the gliding motion of a coupling contact (228) whose pin orientation, as shown in FIG. 9, is also rotated (e.g., also by 90 degrees) relative to the orientation of the pins in the sliding coupling contact (22) of FIGS. 2 and 3. The pins in the gliding receptacle (75) may be oriented along the long direction of a gliding slot (152) shown in FIG. 16.

Figure 10:
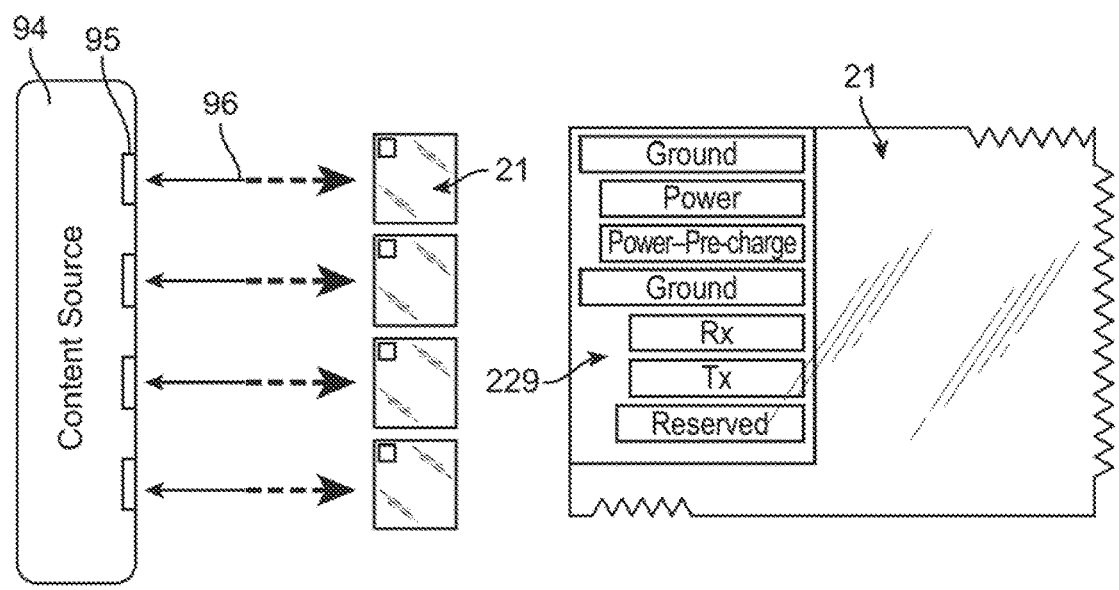
FIG. 10 shows a resting connector(s) and a display module(s) according to an embodiment of the invention.

FIG. 10 shows a resting connector (95), briefly mentioned above, which is another exemplary embodiment for the coupling receptacle (3). The terms resting connector and resting receptacle may be used interchangeably. The one or more resting receptacles (95) are each another exemplary embodiment for the coupling receptacle (3), and may also be used to similarly transfer content from the content source (94) to the display modules (21). Also similarly, the resting connector (95) may be used to charge the display module (21) that includes the power source region (33). The content source (94) is similar to the content sources (24) except for the one or more resting receptacles (95). The resting receptacles (95) similarly carry data signals and control signals, and establish power and ground to enable the transfer of content to the display modules (21). Each resting receptacle (95) will receive one display module (21). The display modules (21) are "rested" in the resting receptacle (95); hence a "pull" (96) or lift motion (schematically shown as arrows in FIG. 10) has to be performed by a user or automated system to transfer content. When content is to be read from the content source (94), the display modules (21) are pulled out of their respective resting receptacles (95). The display modules (21) pulled out will have respective content transferred to them as described above. That is, this resting embodiment uses a transient electrical coupling and transfer of content mechanism similar to that described above for the sliding (slide out (27)) embodiments but with changes in the orientation of the various electrical contacts, pins, traces, and the like to accommodate the motion from the resting (inserted) position of the display module (21) from the resting receptacle (95). For example, though the pins of the resting coupling contact (229) are similar to the pins of the coupling contact (22), there will be changes to the resting connector (95) that are specific due to the pull (96) operation that has to be performed. In an exemplary embodiment, one such change would be the presence of a switch (discussed below) to control when power is available for being supplied to the display module (21) from the resting connector (95). In the embodiment shown in FIG. 10, the display module(s) (21) is (are) pulled in a vertical direction (shown as being to the right in FIG. 10 in the direction of the pull (96), which corresponds to the direction toward the top of the page of FIG. 14 in the plane of that page) relative to the content source (94).

When the display module(s) (21) is (are) in the resting position, it pushes on (they push on) a switch(es) similar to the switches and the like described elsewhere herein for the coupling receptacle (3) or sliding connector (25), except that the switch(es), until activated in this case, also prevents the supply of power to the display module (21). When the display module (21) is lifted or pulled out by a user or an automated assembly, the switch activates or turns on and the power supply allows power to be supplied to the display module (21) according to the specific mating sequence for transient electrical and frictional coupling described above, i.e., ground then power are established to the ground (221) and power (222) pins followed by data and control signal transfer via the Rx (225) and Tx (226) pins during the motion of the display module (21) being pulled from the resting receptacle (95). The switch may be implemented in many ways. For example, preferably the switch may be a miniature contact switch, a microswitch, or a surface-mounted light sensor-based switch, or the like, as described above.

Figure 28:
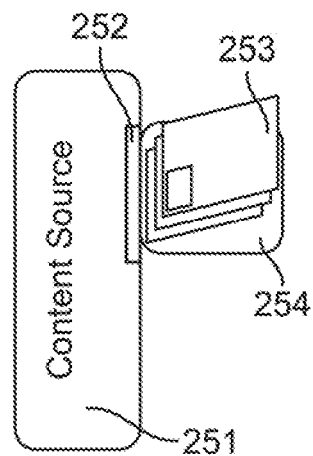
FIG. 28 shows a content source with a stack of display modules that slide into and out of the content source from the bottom of the stack according to an embodiment of the invention

In another embodiment shown schematically in FIG. 28, a horizontal stack (253) of display modules (21) is included with a holding dispenser (254); the display modules are fed out one at a time from the bottom of the stack into a sliding receptacle (25) or a resting receptacle (95) (shown schematically as (252) in FIG. 28 in a content source (251)) in similarity to some paper feeders and the like used in copiers/printers, as would be understood by a person of ordinary skill in the art. Once fed from the dispenser, each display module may transiently electrically and frictionally couple with the content source for content transfer, as described above for slide in (26) or slide out (27). When the resting receptacle (95) is used, the pin receptacles in the resting receptacles (95) that correspond to the pins in the sliding connector (25) will have changes that are specific due to the required pull motion operation similar to what was described above. In another embodiment, the display module, after being fed from the dispenser and after transient electrical and frictional coupling with the content source has occurred, is retracted by a retractor mechanism from the content source. Such a retractor mechanism may be similar to those for retracting paper in copiers/printers, as would be understood by a person of ordinary skill in the art.

Figure 11:
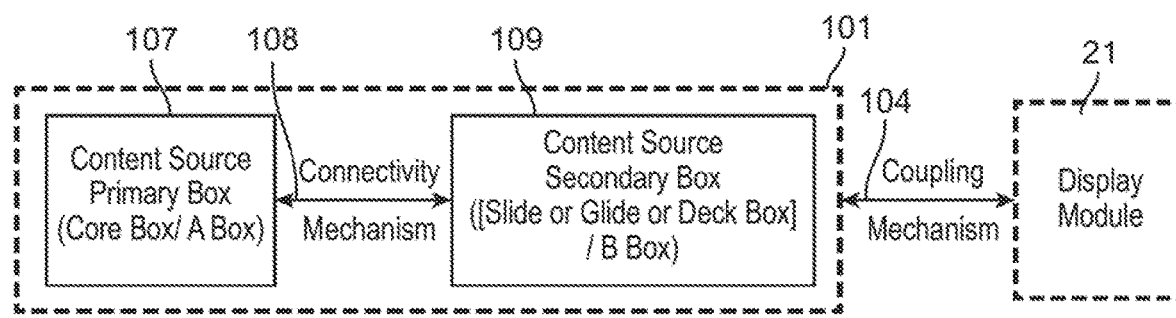
FIG. 11 is block diagram of a content source and its submodules coupling to a display module via a coupling mechanism according to an embodiment of the invention.

FIG. 11 shows a content source (101) and its submodules according to another embodiment of the invention. The content source (101) includes a primary box (107), also known as a core box or an A box, and a secondary box (109). The primary box (107) may be either a slide box or a glide box or a deck box (collectively referred to as a B box), depending on the particular embodiment being used. The primary box (107) and the secondary box (109) are electrically coupled, directly or indirectly, to each other with a connectivity mechanism (108), preferably, USB, although other buses or communication protocols and implementations may be used, as would be understood by a person of ordinary skill in the art. A coupling mechanism (104) (e.g., sliding, gliding, resting, or clamping (which will be described below)) is enabled by the coupling contact (22) in the display module (21) and the coupling receptacle (3, 25, 75, 95), as described above, or (195), as described below. The secondary box (109) is a slide box if it has the sliding coupling receptacle (25) to receive the display module (21) with its coupling contact (22). The secondary box (109) is a glide box if it has the gliding coupler (75) to receive the display module (21) with its gliding coupling contact (228) (FIG. 9). The secondary box (109) is a deck box if it has the resting coupler(s) (95) to receive the display module(s) (21) with its (their) coupling contact(s) (229) (FIG. 10). In other embodiments, the primary box (107) may be a smartphone, tablet or notebook computer, PC, or any generic or special purpose computer, etc. that is runs or executes code for an application to manage the content being sent to the display module. The application may connect either to a remote platform or to a subset of the platform hosted along with the application that will prepare the content to send to the display module. Further details about the platform are disclosed elsewhere herein. In such an embodiment, the secondary box (109) may connect to the primary box (107) using the latter's headphone/earphone/audio jack, Bluetooth, or similar connectivity mechanism. Also in another embodiment, the content source (24) or (101) may support two or more of the connectors, i.e., the sliding connectors (22), and/or the gliding connectors (228), and/or the resting connectors (229) by providing sufficient numbers of coupling receptacles. In another embodiment, the primary box (107) and the secondary box (109) are integrated into one physical unit.

Figure 12:
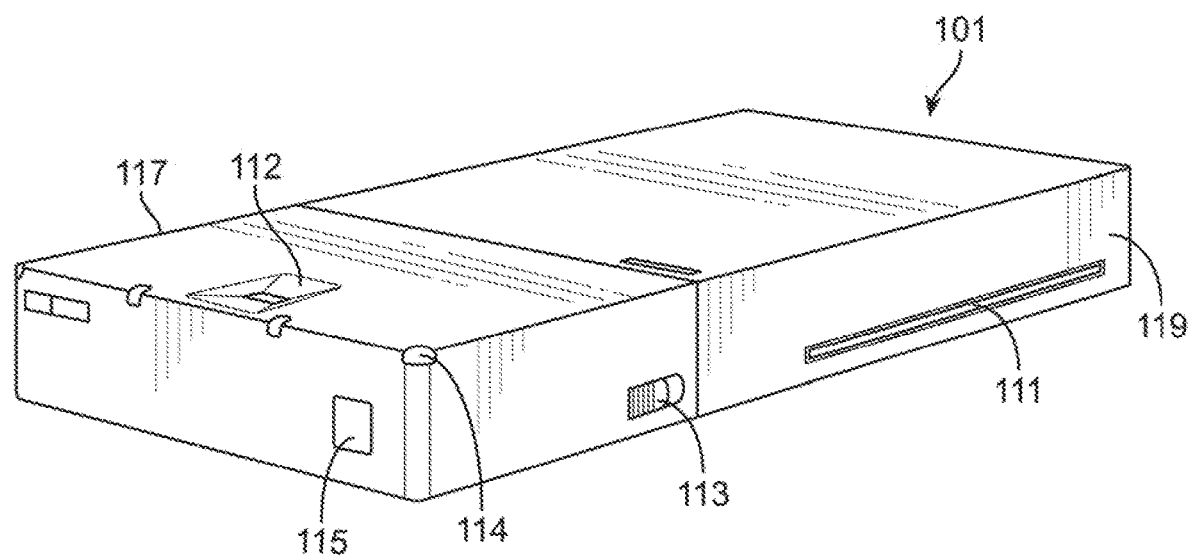
FIG. 12 is a top/front perspective view of a content source in a slide box configuration according to an embodiment of the invention.

In FIG. 12, which shows a top/front perspective view, the details of the content source (101) that supports a single sliding display module (21) embodiment are shown. The content source (101) is the same as content source (24). The content source (101) consists of a primary box (117) and a secondary box (119). The primary box 117 may have networking capability, i.e., it may connect to a local network and/or the Internet. The primary box (117) includes a finger print reader (112) as the AuthNZ component. Such an AuthNZ component is particularly useful when the display module (21) does not have an AuthNZ region (31) and yet the system requires AuthNZ verification before transferring content to the display module (21). In another embodiment, the primary box (117) may not have an AuthNZ component such as the finger print reader (112). In yet another embodiment, instead the secondary box (119) may have the AuthNZ component, such as a finger print reader. The secondary box (119) may include a slot (111) that accepts the display module (21). The user first swipes her finger on the finger print reader (112) and then inserts and removes the display module (21) at the slot (111). The content transfer operation may be the slide in (26) or the slide out (27), as described above. A power switch (115) is used to control power supplied to the primary box (117). The primary box (117) has a mechanism to convey output (e.g., to indicate that power is turned on or to provide other information, such as status of the transient coupling mechanism, to a user. In this embodiment, one or more LEDs (114) are used for this purpose. In other embodiments there may be a display panel, such as a one line LCD display panel, hosted on the primary box (117). This display panel will display messages to convey output to the user. A switch or button (113) helps detach the primary box (117) away from the secondary box (119).

Figure 13:
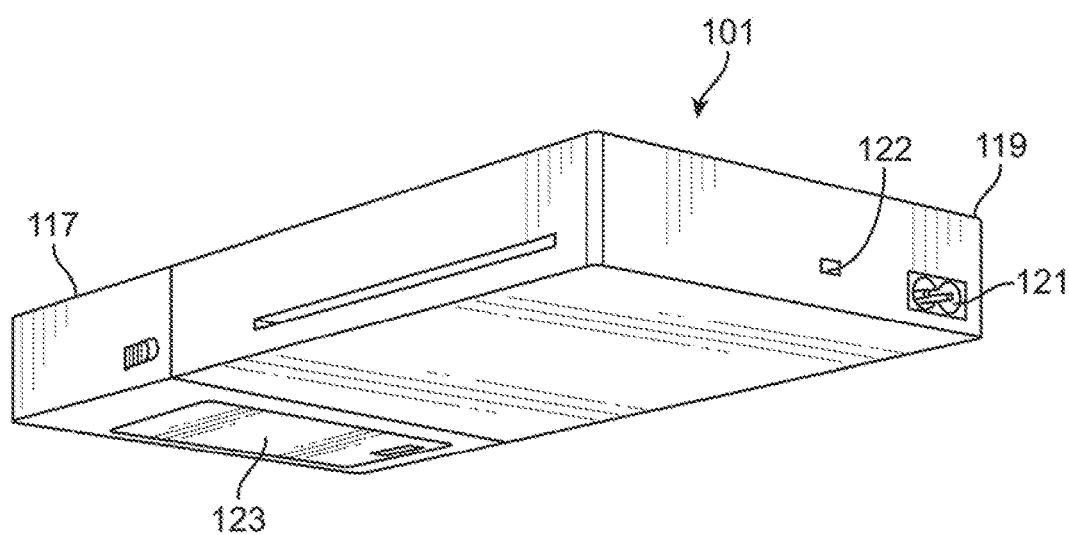
FIG. 13 is a bottom/rear perspective view of the slide box configuration in FIG. 12.

FIG. 13 is a bottom/rear perspective view showing details of the primary box (117) and the secondary box (119) when viewed from the rear and the bottom. In this embodiment, the primary box (117) operates using a battery (123), such as a rechargeable battery, or other power source. The battery (123) may be optional. Without the battery, the primary box (117) will draw power from the secondary box (119). The battery (123) may also get recharged from power supplied by the secondary box (119). The secondary box (119) includes a power plug connector (121) to couple to a wall power socket. The secondary box (119) includes a connectivity port (122). The port (122) may be used for various purposes, such as for firmware upgrades and/or remote monitoring. In other embodiments, the secondary box (119) may also include a mechanism to convey output to the user, such as the one line LCD display or LEDs, and the secondary box (119) may also accept input from a user, such as by including a reset button (not shown). In another embodiment, the secondary box (119) may also include a battery or other wireless charging mechanism along with the power plug connector (121).

Figure 14:
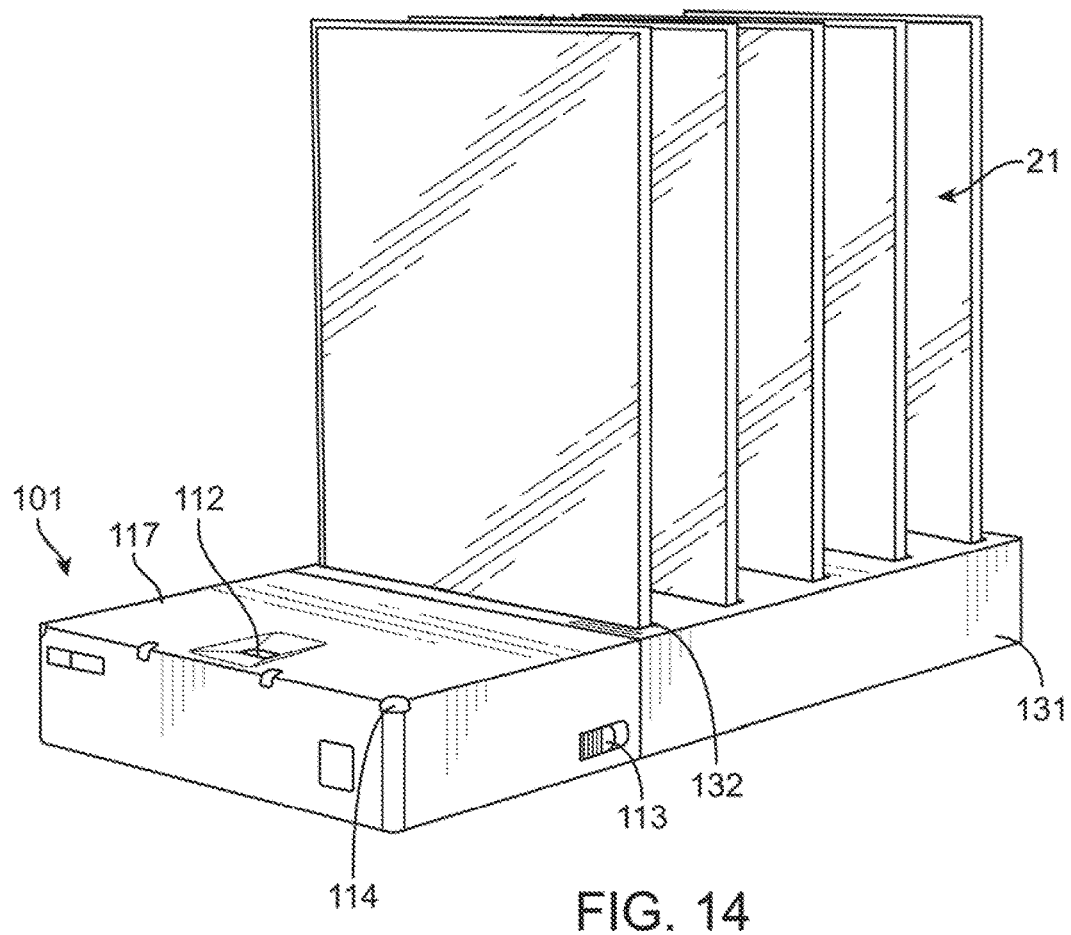
FIG. 14 is a top/front perspective view of a content source in a deck box configuration for multiple rested display modules according to an embodiment of the invention.

In FIG. 14, another embodiment of the content source (101) is shown, wherein the secondary box is a deck box that holds multiple rested sliding display modules (21) like those of FIG. 10. The content source (101) consists of the primary box (117) and a secondary box (131). The primary box (117) is similar to what was described earlier. The secondary box (131) has a deck to support the rested sliding display modules (21). The deck includes of one or more slots (132), each of which may hold a rested sliding display module (21). The secondary box (131) also includes a power plug connector (shown in FIG. 13) and a connectivity port 122 (also shown in FIG. 13), as described previously for the sliding secondary box (119).

Figure 15:
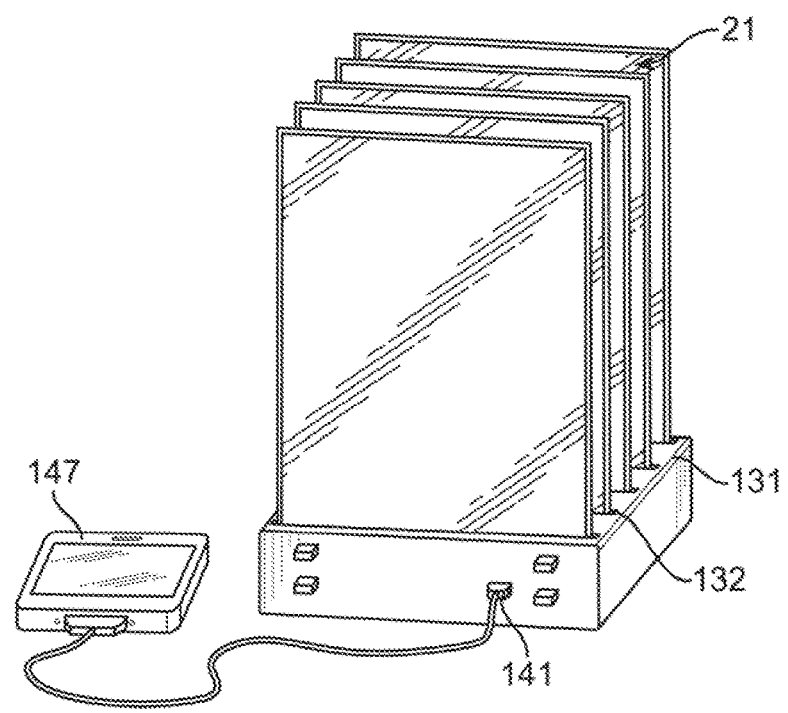
FIG. 15 is a top/front perspective view of a deck box configuration including a smartphone used as a content source instead of a Core box according to an embodiment of the invention.

FIG. 15 shows another embodiment of the content source (101) in which a smartphone (147) is used as the primary box (117) to connect to the secondary box (131) through a connectivity port (141). In this embodiment, USB is an exemplary connectivity mechanism. Other connectivity mechanisms may be wireless technologies, such as Bluetooth, or those described earlier. The smartphone (147) would have similar capabilities to what was described earlier for the primary box (107). The details of the secondary box (131) are similar to what was described earlier for the secondary box (109, 119). Although the smartphone (147) is shown in FIG. 15, the primary box (117) may also be replaced by other classes of devices, such as a tablet or notebook computer, PC, or other computing devices that runs or executes code for an application to manage the content being sent to the display module. The application may connect either to a remote platform or to a subset of the platform hosted along with the application that will prepare the content to send to the display module. Further details about the platform are disclosed elsewhere herein.

Figure 16:
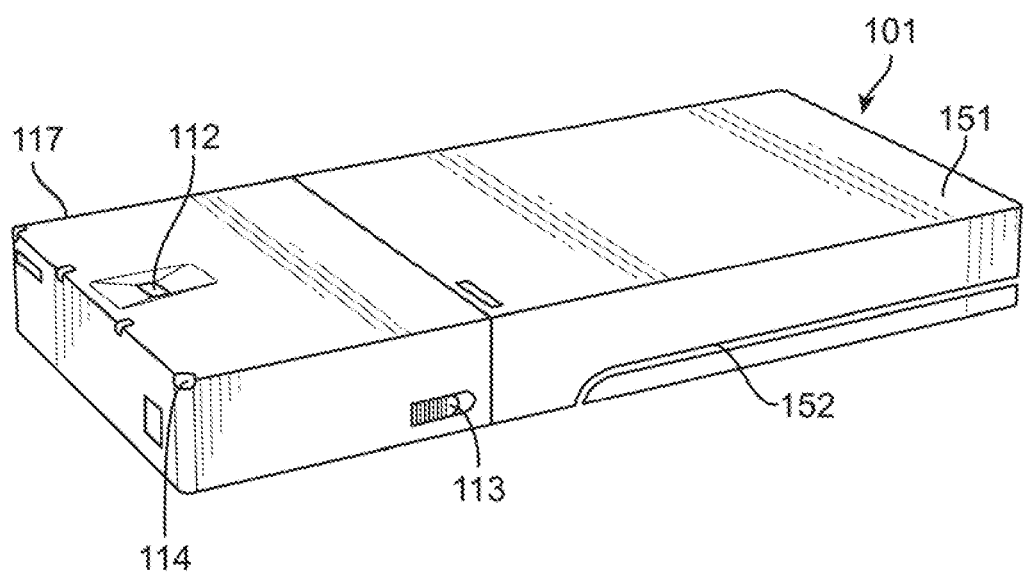
FIG. 16 is a top/front perspective view of a content source in a glide box configuration according to an embodiment of the invention.

FIG. 16 shows an embodiment of the content source (74) as another embodiment of the content source (101). A secondary box (151) is a glide box that accepts the display module (21) of FIG. 9, although a display module similar to that shown in FIG. 8 with one or more coupling contacts (228) like that of FIG. 9 instead may be accepted. The content source (74) consists of the primary box (117) and the secondary box (151). The secondary box (151) supports gliding as the coupling mechanism. The secondary box (151) includes a slot (152) through which the gliding display module (21) may be glided similar to a credit card reader, as described above. The other details of the secondary box (151) are similar to what was described earlier for the secondary box (119). The details of the primary box (117) are similar to what was described earlier for the primary box (107). Although not shown in FIG. 16, the embodiment of FIG. 16 may include the power plug connector (121) and the connectivity port (122) similar to what was described for FIG. 13.

Figure 29:
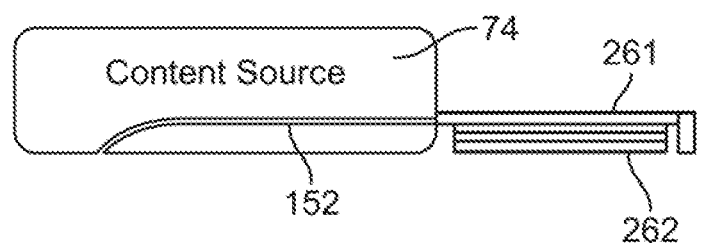
FIG. 29 is a side view of a content source with a stack of display modules that glide from the top of the stack (or alternatively, from the bottom of the stack) through the content source according to an embodiment of the invention.

FIG. 29 shows an embodiment in which the gliding content source (74) may also be used in automated implementations, for example with a stack (262) of display modules (21). One display module (21) at a time may be automatically fed or pushed into the slot 152 by a dispensing machine (261), similar to the type of technology used for feeding paper from the top or the bottom of a stack of paper into a copier/printer, as would be understood by a person of ordinary skill in the art. The dispensing machine (261) feeds a display module from the stack (262), glides it through the slot (152) as the display module engages in the transient electrical and frictional coupling mechanism to transfer content as described above. A user may pull the display module as it comes out of the slot 152 or the display modules may be automatically moved and stacked in an output stack after gliding through the slot 152 one at a time (not shown). For the latter, an automated retractor machine analogous or similar to those used to retract sheets of paper output from a copier/printer may be used to stack the output display modules, as would be understood by a person of ordinary skill in the art. In this case, the display modules are obtained in similarity to the sheets of paper obtained by the copier/printer from a stack of paper via a feeder mechanism and output one at a time or to the output stack by a retracting mechanism or machine pulling the display modules out of the slot (152).

Figure 17:
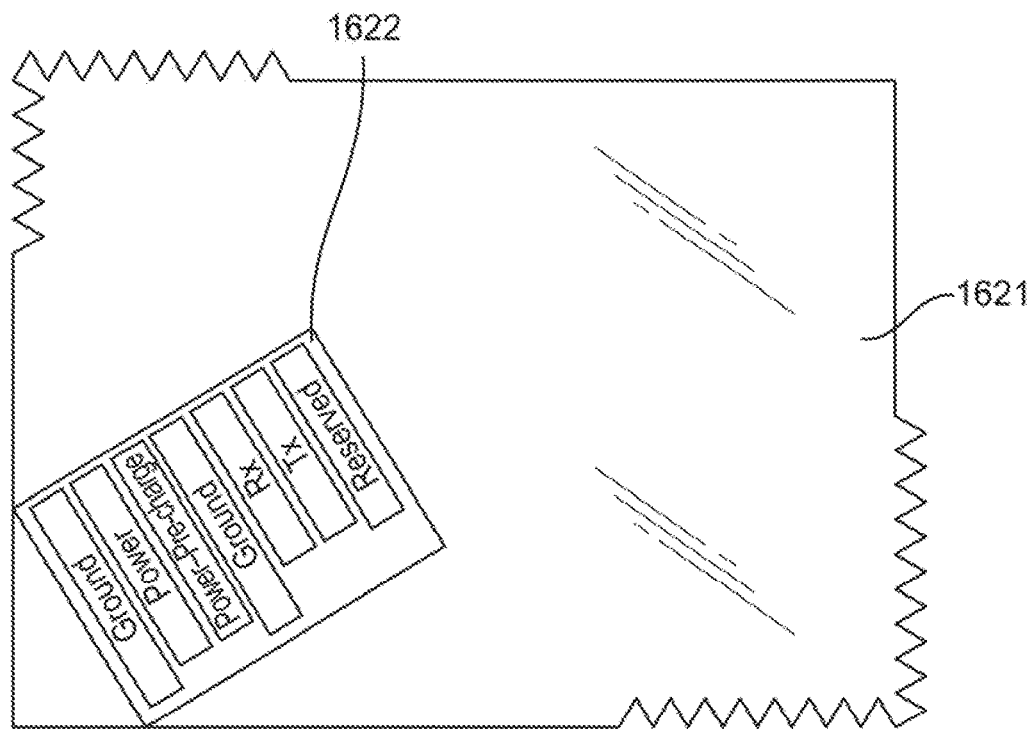
FIG. 17 is a top view of a display module with an obliquely positioned coupling contact according to an embodiment of the invention.

FIG. 17 shows an alternative embodiment of a display module (1621). A coupling contact (1622) including the mask and the pins is shown at an oblique position relative to those described above. The coupling contact (1622) is part of the display module (1621) as before. The display module (1621) may be used, for example, with a content source (1874) of FIGS. 19 and 20, which will be described below. The display module (1621) may provide a faster glide-through time duration than that of other embodiments, as only the corner portion of the display module (1621) that includes the coupling contact (1622) may need to be glided through the gliding receptacle (75)/slot (152).

FIG. 18 shows another alternative embodiment of a display module (1721). A coupling contact (1722) including the mask and the pins is in an oblique position similar to that of FIG. 17, but a portion of the coupling contact (1722) is located outside or protrudes from the display module (1721). For this embodiment, the gliding motion would occur somewhat similarly to that for the embodiment shown in FIG. 17. In this particular embodiment, the coupling contact (1722) is located on one side (or face) of the display module (1721). Hence the underlying edges of the display module (1721) are shown in dashed lines.

FIG. 19 shows a cross-sectional top view of the content source (1874) having a concave-like housing (1877) and FIG. 20 is a front view of the content source (1874) looking along the direction AA' in FIG. 19. A slot (1852) is for a gliding connector (1875), which is like the gliding connector (75) shown in FIG. 8. In this embodiment, the slot (1852) may be shorter in length than the slots shown previously for other embodiments, such as in FIG. 16. With this type of housing, the display modules (21) (in FIG. 9), (1621) or (1721) (in FIGS. 17 and 18) have less "distance to glide" (1876) than through the longer slots described above to receive the transferred content. Certain embodiments of a shorter gliding connector and a shorter slot in a similar concave-like housing to that shown for the embodiment in FIG. 19 may be used to attach to a smartphone, tablet or notebook computers, PC, or other computing devices analogous to the credit card readers that attach to similar devices, as would be understood by a person of ordinary skill in the art.

In some embodiments, one or more or a combination of the sliding, gliding, resting and corner coupling contacts (22, 227, 229, 1622, or 1722) may be present in a single display module (21). Moreover, in certain embodiments, the secondary box (109, 119, 131, or 151) may include one or more of, or a combination of, the sliding receptacle (25), gliding receptacle (75), gliding receptacle (1875), resting receptacle (95), or clamping receptacle 195 (FIGS. 21 and 25).

In another alternative embodiment, shown in FIG. 21, a content source (19) includes a clamping receptacle (195) as an embodiment of the connecting receptacle (3). The clamping receptacle (195) includes individual electrically conductive clamping connectors (210211) that may be of the same or different lengths for ground, power, data, and control, which clamp and connect to the corresponding pins in a coupling contact (1922 or 22) of the display module (1921 or 21) (FIGS. 21, 24, and 25), as similarly described above. The clamping may provide a more secure physical and electrical connection in environments that are inherently shaky or bumpy, or propagate vibrations, such as in vehicles, airplanes, or boats. These individual connectors will make contact to their respective ground, power, data, and control pins or pads in the coupling contact (1922, 22) in a predetermined sequence similar to what was described earlier whether or not the pins or pads in the coupling contact (22) are of different lengths as described above, or of the same length (coupling contact 1922), for example, as in FIG. 9 or 22 (described below), and the slide in (26) or slide out (27) operation will not be affected. One embodiment of this would have the individual connectors inside the clamping connector (195) (FIGS. 24 and 25) each biased by a corresponding spring or mechanical spring-like mechanism, each spring having a different spring constant such that closing the clamping connector (195) only allows electrical contact to be made between the individual connectors in the clamping connector (195) to the corresponding pins or pads of the coupling contact in the predetermined sequence as described above. In this case, the individual clamping connectors (210211) may be of the same length. The clamping connector (195) may be clamped to close on the coupling contact by the user pressing it or pressing a button, or automatically by a mechanism activated via the switch (2002) and the processing element (210) in the content source. With the clamping receptacle (195), the display module (21) is slid into the clamping connector (195), as in slide in (26) or slide out (27), for content transfer. The clamping action of the clamping receptacle is not so tight as to prevent sliding, but is tight enough so make the grip or mechanical force on the pins or pads sufficient to withstand shakes, vibrations, or bumps, so as to provide efficient transient and frictional electrical couplings for the ground, power, data, and control electrical connections, and for content transfer. In other embodiments, a simple clamp (e.g., whose clamping is analogous to a clothes pin) may be provided with the content source located proximate the coupling receptacle (3, 25) for merely adding more pressure between the pin receptacles in the coupling receptacle and the pins in the coupling contact (22) as they are making transient electrical and frictional coupling during the slide in (26) or slide out (27). Such a clamp would not provide so much force or pressure as to interfere with these sliding electrical processes. Similarly, other forms of clamping may also be used in other embodiments for the same reason in conjunction with the other transient electrical and frictional coupling mechanisms mentioned herein.

Figure 25:
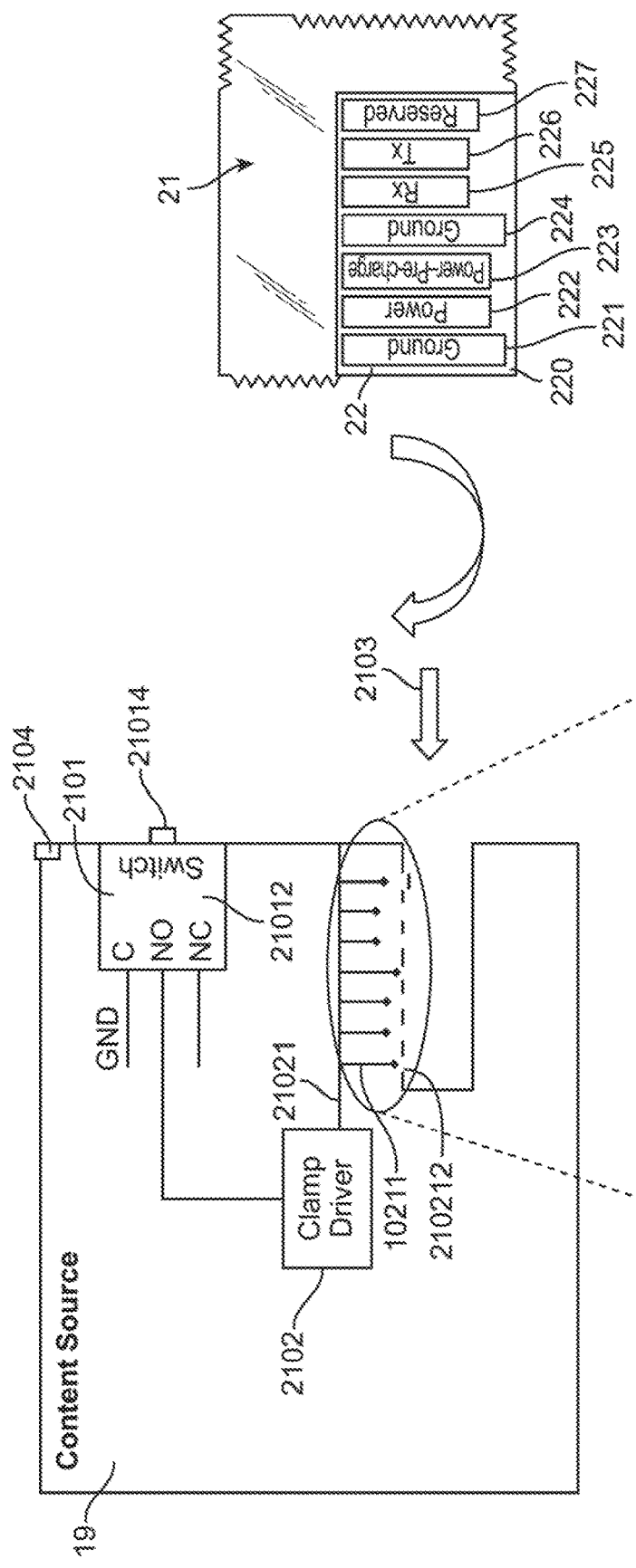
FIG. 25 is an exploded schematic cross sectional view of a clamping contact area according to the embodiment of the invention.

More details about the embodiments shown in FIGS. 24 and 25 are now provided. FIGS. 24 and 25 show a cross-sectional/side-view of the clamping receptacle (195) in the content source (19). FIG. 25 zooms into a portion of the clamping receptacle (195). The display module (21) is pushed into (2103) a slot by a user or automated system. A key (21014) on a switch (2101) is pressed or activated by the user or automated system. When it is pressed a NO (normally open) pin (21012) goes active and informs a clamp driver (2102) via electrical or electronic signal of its state. The clamp driver (2102) then mechanically drops a clamping mechanism (e.g., analogous to a clothes pin) from a pin arm (21021), and individual ground, power, data, control, etc. clamping connectors (e.g., pins) are forced to make electrical contact with their corresponding electrical contacts (220-227) in the coupling connector (22) in a predetermined order similar to what was discussed earlier, for example, because of differing clamping connector lengths. In certain embodiments, even with clamping, the coupling connector (22) may slide, glide, etc. for transient and frictional electrical coupling with the clamping pins (210211) for establishing ground, power, data signal and control signal paths for content transfer as described above. For demonstrative purposes, one such clamping connector pin is illustrated. When the clamp driver (2102) senses that the key (21014) has been pressed, it first drops a ground pin (210211) through a hole (210212), and subsequently it drops the other pins in the predetermined sequence. An LED (2104) is used to convey the status of the clamping operations, such as solid green indicates the clamping is in progress and data is being transferred, whereas blinking green indicates that the display module may be pulled out. In other embodiments, a switch may be present at the end of the slot in FIG. 25 (although not shown in the figure) to detect the display module has been pushed in (2103). This switch then informs the clamp driver that the display module is ready to be clamped.

Figure 22:
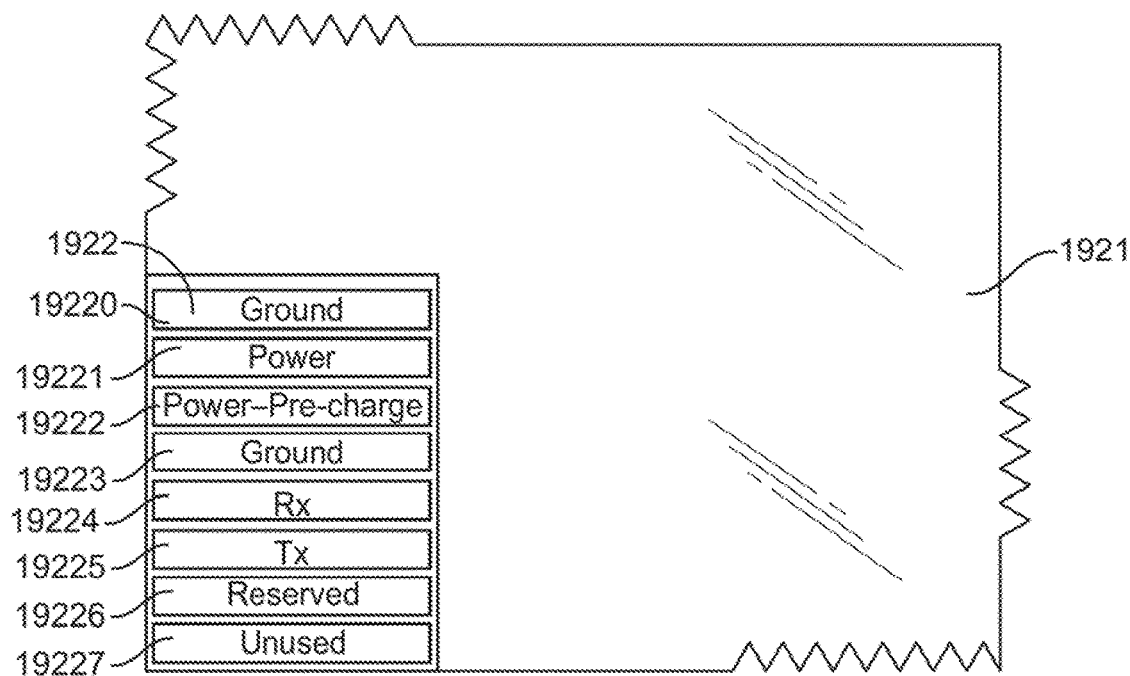
FIG. 22 is a top view of a coupling contact with labeled contact pads according to an embodiment of the invention.

FIG. 22 shows details of another coupling contact (1922) embodiment in a display module (1921), which includes a mask (19220) and a set of contact pins or pads (19221, 19222, 19223, 192224, 19225, 19226 and 19227) similar to that described earlier. The difference is that these contact pins or pads in the coupling contact (1922) may have the same lengths for ease of manufacture or fabrication, whereas they were of different lengths as described above for the coupling contact (22). In this embodiment, it is the individual clamping connectors (210211) within the clamping receptacle (195) that clamp onto their corresponding ground, power, data, and control pins or pads in the predetermined sequence. Here, the order is a predetermined timing control sequence that does not rely on different clamping connector (210211) lengths, but instead relies on mechanically activating one or more of the individual clamping connectors (210211) at a time to clamp down and make contact with their respective pins or pads in the coupling contact (1922 or 22) to ensure that the proper ground and power connections are established in time before the data and control connections are established.

Figure 23:
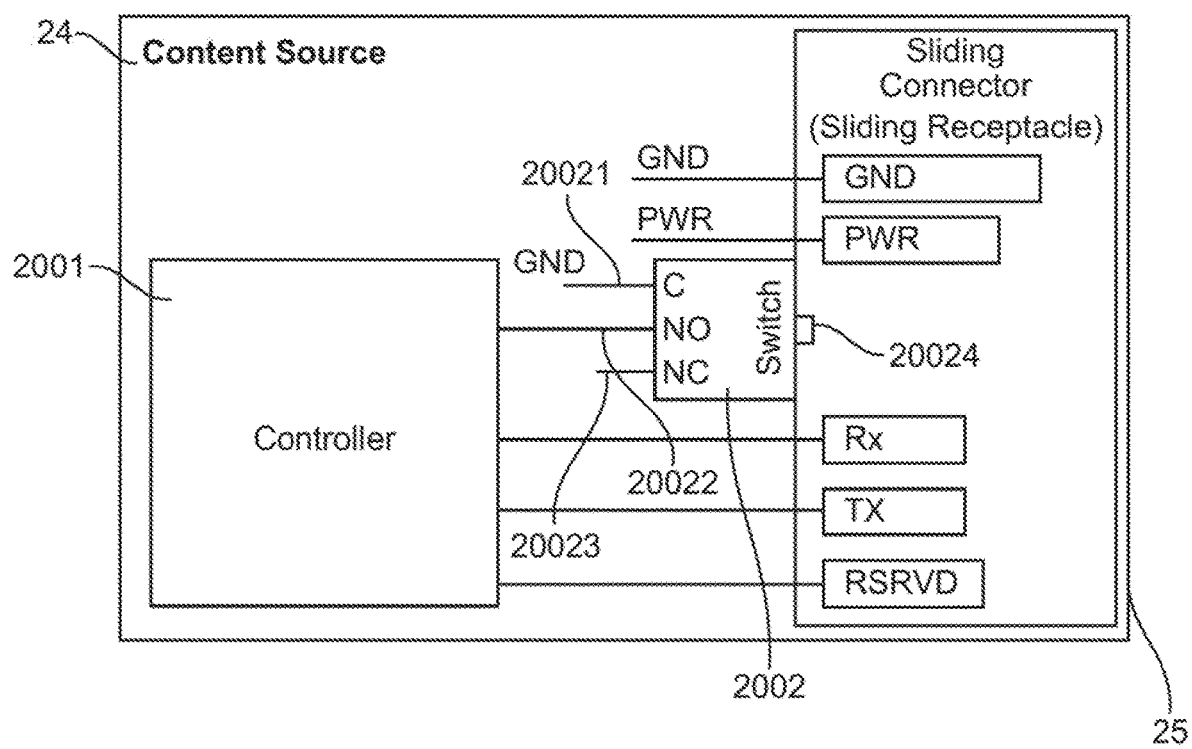
FIG. 23 is a block diagram of a switch or switching mechanism in a sliding connector in a content source according to an embodiment of the invention.

The switch (2002) will now be described further. FIG. 23 shows a push switch (2002) or similar mechanism that may be included in the sliding receptacle (25) in a content source (24). Although the push switch (2002) is shown, any other type of switch is contemplated, as would be understood by a person or ordinary skill in the art, including, but not limited to a miniature switch, a microswitch, LED or other light source and light detector, or other electrical or electronic switch or the like. The switch (2002) includes electrical contacts CG (20021) (common/ground), NC (20023) (normally closed), and NO (20022) (normally open) (i.e., no current flows). The switch improves the reliability that the coupling contact (22) has been slid far enough into the coupling receptacle (3) or (25) such that the sequence for establishing the ground and power contacts before the data and control contacts may properly occur. When a key (20024) in the switch (2002) is pressed by the coupling contact (22) (not shown) as it is being slid into the sliding receptacle (25), the switch (2002) is activated, which means the NO pin (20022) becomes active. When this happens, signals are provided to a controller (2001) in the content source (24) to allow power to be made available for supply to the display module (21) at the right time for transiently coupling during the predetermined sequence before content transfer, as described above. Using such a switch may improve the reliability of the transient coupling mechanisms described above.

Platform for Transferring Content to Display Devices

Although embodiments of the invention have been described with particular reference to AISs, CHRs, digital signage, pricing signage, announcement signage, etc., it is to be understood that embodiments of the invention may be implemented in any information technology (IT) system in which the efficient creation, transmission, and updating of static or dynamic images or content is desirable. A person of ordinary skill in the computing arts will recognize that the disclosed embodiments have relevance to a wide variety of computing environments in addition to those described above and below. In addition, the methods of the disclosed invention may be implemented in software, hardware, or a combination of both. The hardware portion may be implemented using special logic; the software code portion may be stored in a memory and executed by a suitable instruction execution system such as a microprocessor, microcontroller, CPU, personal computer (PC), mainframe, server, smartphone, or other computing device.

A "memory" or "recording medium" as discussed herein may be any means that contains, stores, communicates, propagates, or transports a program (e.g., a program or code for the application or the platform or the analytics infrastructure (described below)) and/or data for use by or in conjunction with an instruction execution system, apparatus, or device. Memory and recording medium may be, but are not limited to, an electronic, magnetic, electromagnetic or semiconductor system, apparatus, or device. Memory and recording medium also includes, but are not limited to, for example, the following: portable computer diskette, random access memory (RAM), read only memory (ROM), erasable programmable read only memory (EPROM or Flash memory), portable compact disk read only memory, or another suitable medium upon which a program and/or data may be stored.

In accordance with embodiments of the invention, a display device registers with a platform. Such display devices and platform(s) were described above and will be further described below. Registration allows the platform to identify the particular display device. The registration process may occur in different ways. Three exemplary ways will be described, although a person of ordinary skill in the art would understand other possible ways. First, registration may be initiated by the platform announcing its availability to the display device and then the display device responds by indicating to the platform its presence. A second way is when the display device is powered up and it enumerates its presence to the platform. A third way is when a user inputs the display device's details into the platform's front-end using a user interface. In accordance with an embodiment of the invention, the registration for a display device that uses the transient electrical and frictional coupling described herein may use a combination of the aforementioned second and third ways.

Upon registration, the platform then lets a user assign a package to the display device or to more than one display device. Packages are disclosed in the provisional patent application (Ser. No. 62/176,798) by the same inventor. Embodiments of the invention include a programmed method for the generation of one or more packages. The package may include information about the data to be displayed on the display device; it also may include information about the origin of the data and design information that indicates where the data is to be placed on the display device.

The platform provides tools to manage the package. The platform itself may also have the capability to manage the display device(s). Users with various roles (such as administrator, layout creator, store manager, etc.) in the system are also identified and managed by the platform, and the platform responds to their directives regarding the system (i.e., the platform also manages any inputs obtained from the user, in performing its tasks), once their login credentials and privilege levels are verified, authenticated, or authorized. The platform maintains a database of these users and any other users, which stores login credentials and their privilege level for access to and/or modification to the platform and display devices. The platform also allows various applications to access the display device. These applications may be associated with various different verticals (or market segments). Thus, the platform acts as a gateway for the applications to access the display devices.

According to an embodiment of the invention, Table 1 (above) may be updated to include digital signage and/or announcement signage as exemplary AISs for a business owner. Embodiments of the invention may also provide three different modes for the digital signage—a standard mode, and/or a "show source" mode, and/or a "follow source" mode. The show source and follow source modes are advanced versions of the standard mode, which will be described further below.

Figure 30:
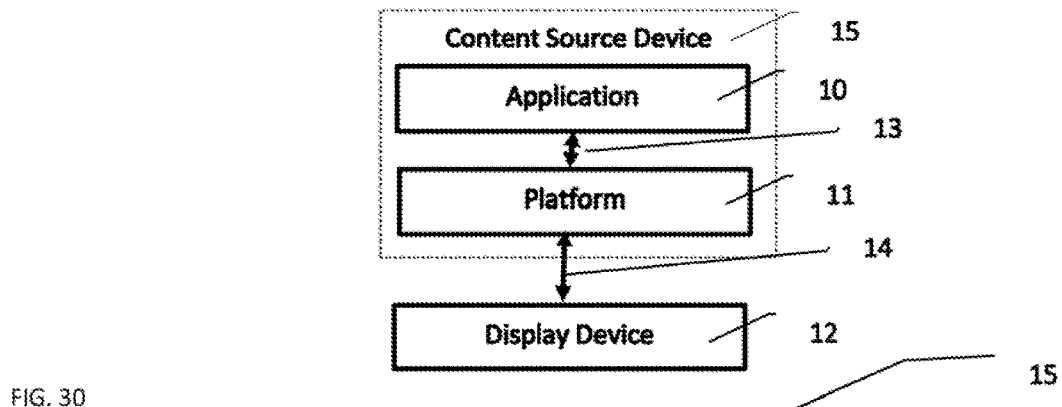
FIG. 30 shows an overview of components according to embodiments of the invention.

FIG. 30 shows an overview of components according to embodiments of the invention. FIG. 30 is similar to FIG. 26, but with an application (10) and platform (11) residing in the content source (24). The application (10) accesses (13) the platform (11) to get access to a display device (12) managed (through I/O) (14) by the platform (11). In certain embodiments, a content source device (15) hosts the application (10) and the platform (11) in memory on the content source device, such as described above and below. In other embodiments, also as described above and below, the application (10) and the platform (11) may be hosted on different machines, computing devices, servers, etc., or other devices on a network.

Figure 57:
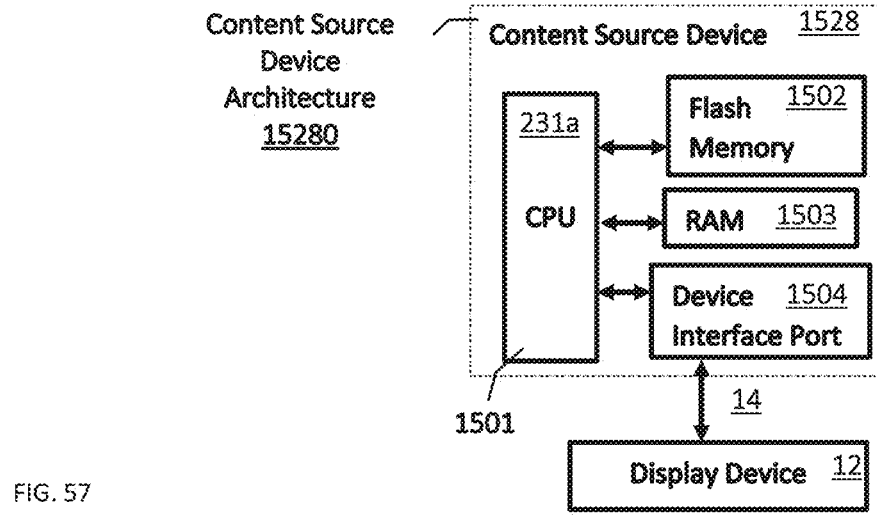
FIG. 57 shows a content source device architecture according to an embodiment of the invention.

FIG. 57 shows a block diagram computing system architecture (15280), including a content source device (1528), in accordance with an embodiment of the invention. It should be noted that there are many possible computing system architecture configurations, of which computing system architecture (15280) is only one simple example. The content source device (1528) includes volatile memory or recording medium and non-volatile memory or recording medium. RAM (1503) may be a typical volatile memory used in the content source device (1528). The RAM (1503) would mostly be used to store data during operation of the content source device (1528), such as when rendering content. The details of the rendering process are discussed later. A non-transitory computer-readable storage medium, such as flash memory (1502), is a typical non-volatile memory that may be used in the content source device (1528). The flash memory (1502) would mostly be used to store boot code, program code, and configuration data. It is contemplated that different types of memory, such as those described above, may be used for the volatile memory and non-volatile memory as the storage medium, as would be understood by one of ordinary skill in the art. A CPU (1501) (which may be chosen, for example, from current processor families, such as Intel Core i7/i5/i3 Processors, Intel Xeon Processor E5 v3, Oracle SPARC T5, Applied Micro's ARM based X-Gene SoC, and others, or instances of VM running on such processor families) is programmed to execute or operate the application (10) (see FIG. 30) and the platform (11) logic, such as software code, hardware, or a combination of both, to provide the functions of the content source (15280) as a specially programmed generic or special purpose computer such as custom ASIC, SoC, FPGA, or others. The application (10) and the platform (11), or portions thereof, may be stored in the flash memory (1502). A device interface port (1504) allows a content source device framework (203) (described below) to connect and transfer I/O (14) with the display device (12). There may be one or more device interface ports (1504) in the content source device (1528). There may be a device interface port (1504) for each "native pass thru" (described further below) and similarly another device interface port (1504) for each device access plugin (also described further below).

Figure 58:
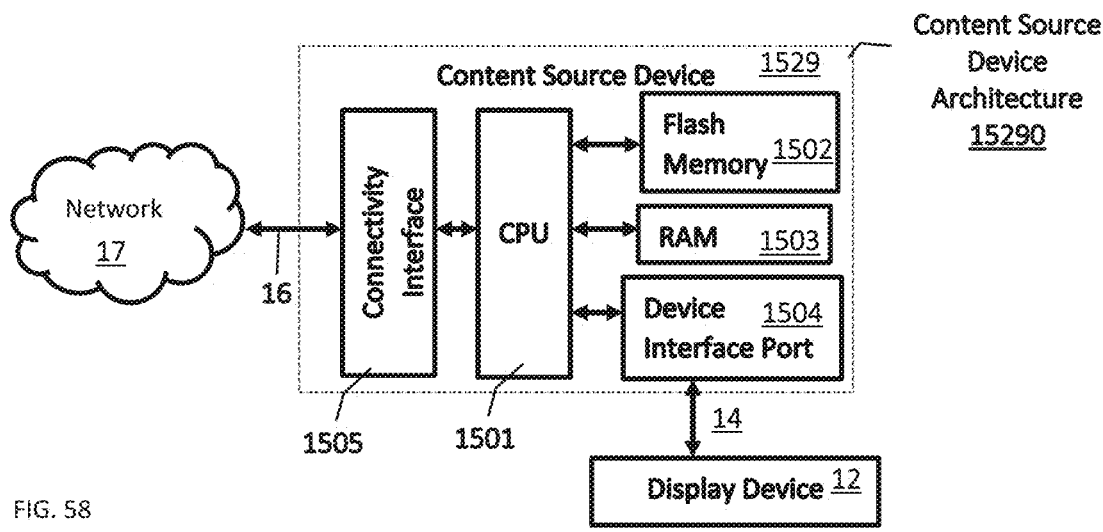
FIG. 58 shows a content source device architecture according to another embodiment of the invention.

FIG. 58 shows a block diagram computing system architecture (15290) including a content source device (1529) in accordance with another embodiment of the invention. It should be noted that there are many possible computing system architecture configurations, of which computing system architecture (15290) is only one simple example. FIG. 58 shows the content source device (1529) that can connect to an external network (17). What was disclosed with respect to the embodiment shown in FIG. 57 is similar for the embodiment shown in FIG. 58. In the embodiment of FIG. 57, the application (10) and the platform (11) logic, such as software code, hardware, or a combination of both, or portions thereof, may be hosted outside or external to the content source device (1529). For example, the application (10) and the platform (11), or portions thereof, may be hosted in the network (17), e.g., in non-transitory computer-readable storage medium, such as flash memory. The network (17) may be a LAN, WAN, World Wide Web, Internet, or other network, etc. A connectivity interface (1505) provides the CPU (1501) with access (16) to the network (17). For the other elements in FIG. 58, please refer to the description of FIG. 57 above.

Figure 31:
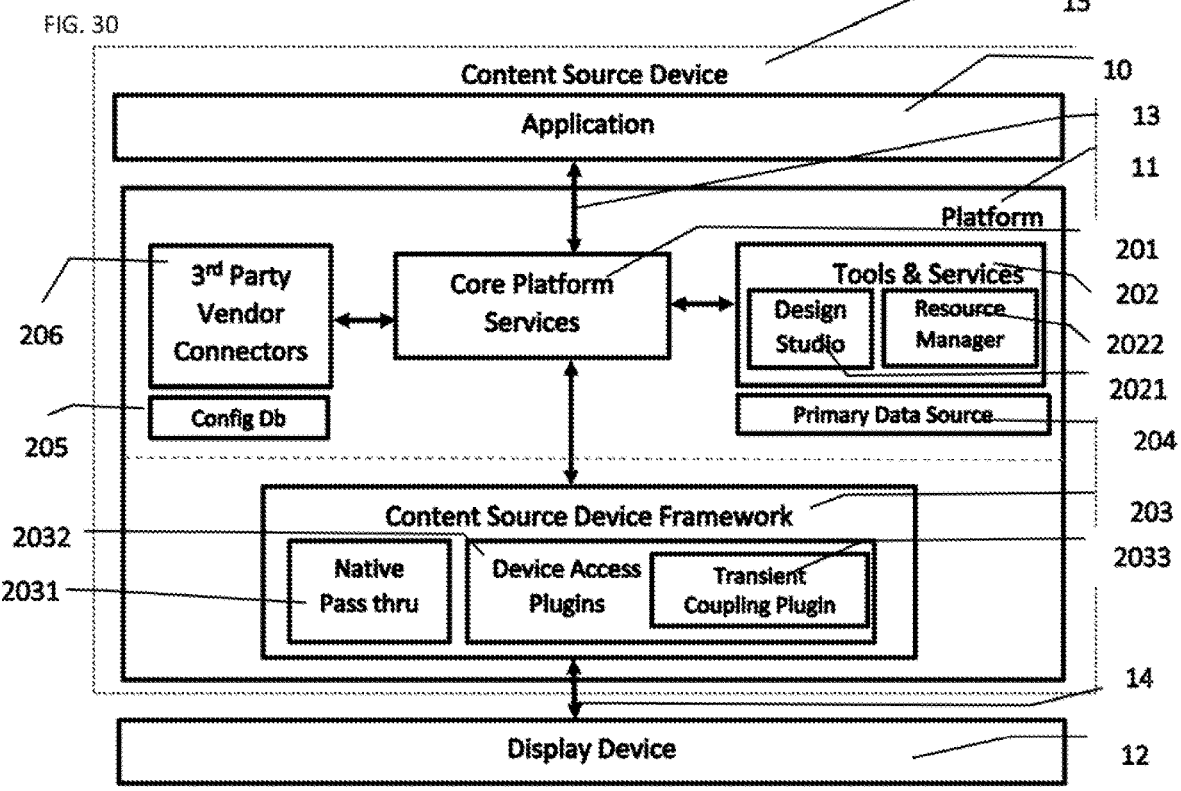
FIG. 31 shows details of a platform according to an embodiment of the invention.

FIG. 31 shows details of the platform (11) in accordance with an embodiment of the invention. The platform (11) includes a core platform (201) that provides a display device provisioning and orchestration capability while supporting the application (10) to access the display device (12) through a content source device framework (also known as device access technology packs) (203). A framework is a set of reusable software modules that allow a particular type of hardware to integrate with the rest of the system. For example, in a typical operating system, a human interface device (HID) framework allows a plugin to be hosted to interface for a particular type of hardware, such as a touch screen or a keyboard. A plugin is logic in the form of hardware or software (modules or code), or a combination of both, that acts as a special adapter to allow connecting a display device, which is not using a well-known protocol, to the application and/or the rest of the platform. Referring again to FIG. 31, the platform (11) may host third party vendor connectors (206) that are used to connect to external servers for functions such as content storage & management, identity management, inventory & asset management, and media server. The core platform services (201) use these connectors (206) to manage data residing with third party vendor servers/suites.

A service refers to a set of related software functionalities that may be reused for different purposes, together with policies that should control its usage. Tools & Services (202) include a design studio (2021) and a resource manager (2022). The design studio (2021) manages the packages, such as designing the layout in which to place the data fields. The resource manager (2022) manages and administrates the link between the display device, data source, and the application. The primary data source (204) is a data source that is local to this platform (11). Other data sources may be external to the platform (11). Also, portions of the data source may reside on external servers, thus accessible through the third party vendor connectors (206). The primary data source (204) may also act as a cache to data retrieved from other non-primary data sources. The tools (202) also facilitate capture of display device usage logs and similar information. The core platform (201) will then analyze the captured data to predict and make recommendations for maintenance, asset planning and so on.

Further, in FIG. 31, the content source device framework (device access technology pack) (203) enables a framework to manage display device specifications, characteristics and rule sets. The device specification and characteristics include the type of display technology, screen size, color depth, resolution, embedded font(s), firmware version, any multi-display module setup details, and other non-display-related characteristics, such as whether the display device includes network capability, and whether there are regions to support input & output. The content source device framework (203) also manages a location awareness aspect of the display devices. Within the content source device framework (203) are two modules, native pass thru (2031) and device access plugin(s) (2032). The native pass thru (2031) allows the display device to be accessed using well-known protocols for wired and wireless technologies, such as TCP/IP, USB, HDMI, CAN, Bluetooth, Bluetooth LE, ZigBee, and others. For example, a smart watch that is accessible over TCP/IP is an exemplary embodiment of a display device that will be accessed over the native pass thru (2031). A tablet, smartphone, or similar device that is accessible over TCP/IP or Bluetooth is another exemplary embodiment of a display device that will be accessed over the native pass thru (2031). In certain embodiments, the platform and the application are resident on such mobile devices, having access to a display device using the native pass thru-based mechanism.

The device access plugin(s) (2032) are a set of one or more plugins that, as mentioned above, may require logic in the form of intermediary hardware or software or both to allow the display device to connect to or communicate with the application and/or the rest of the platform. In accordance with an embodiment of the invention, a transient coupling plugin (2033) integrates display devices that use a transient electrical and frictional contact coupling mechanism, as described above, with the platform and the application. The transient coupling plugin provides for control, address, and data communications between the display devices and the platform and the application. The provisional application Ser. No. 62/123,804 by the same inventor discloses further details about the transient coupling mechanisms. Other embodiments provide for the display device to couple to the content source via standard wired communication connections, such as USB, Thunderbolt, Lightning, and Wired Ethernet, and so on, and also over standard wireless communication connections such as Bluetooth, Wi-Fi, NFC, and so on The content source device framework (203) allows other platform modules (besides the device access plugins) to communicate with the display device (12). The display device consists of one or more display elements (e.g., ePaper display elements), each of which display content as output. The content source device framework (203) may have location awareness, i.e., it knows where, and the environment, in which it is being used. If it does not have the built-in ability to be location aware, the core platform services (201) will have the ability to inform the content source device framework (203) of its location. If the core platform services detect that the device access plugin (2032) is locally connected, then the former will query the underlying operating system to get the geo location information. If the content source device framework (203) is remote from the core platform services (201), the latter will use geolocation lookup services based on the display device's address or identifier. The geolocation lookup services may be external to the platform. The core platform will allow the system administrator or user to override the geolocation information identified by the core platform.

In other embodiments, the content source device framework (203) may be physically different hardware than the rest of the platform. A benefit of such an approach is the ability for a platform to manage multiple content source devices, and each content source device can access one or more display devices. In certain embodiments, the application, the platform and the content source device framework are on the same hardware unit and collectively may be referred to as the content source device.

A configuration database (205) stores information about the platform (11) and its various components, information about the display devices (12) managed by the platform (11), and also information about various other platforms (11). The platform (11) and its components may either be included in the same machine or they may be remote from each other, i.e., distributed on different machines, computing devices, servers, etc. in a network. The platform (11) also includes one or more databases to store data managed by the tools & services (202). The database(s) may be either local, i.e., on the same machine, or they may be distributed on different machine(s).

Figure 32:
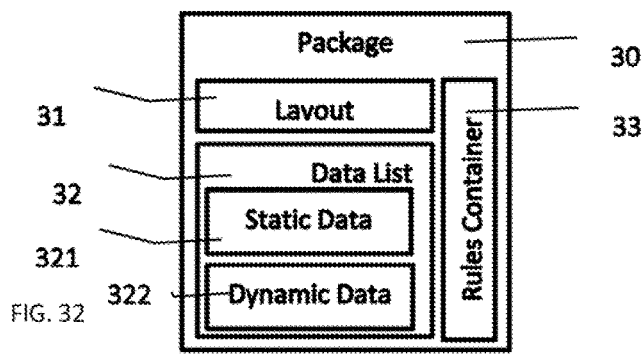
FIG. 32 shows an internal structure of a package according to an embodiment of the invention.

FIG. 32 shows a block diagram data model of an internal structure of a package (30) in accordance with an embodiment of the invention. The package (30) includes a layout (31), a data list (32), and a rules container (33). The layout (31) includes details about how and where data is to be placed, i.e., positioned, on the display element of the display device (12). The data list (32) is a collection of data to be displayed, which is categorized as static data (321) or dynamic data (322). At the time of rendering the data to generate content for the display device (11), the static data (321) does not change since the package (30) was put together. It should be noted that rendering the data, as discussed herein, may also be referred to as rendering the package (including the content) or rendering the content. The dynamic data (322), on the other hand, changes since the package (30) was put together, so the dynamic data (322) is fetched from a data source before generating the content. The data source may be either local to the platform (11) or it may be remote from the platform (11) (e.g., on an external server(s) or database(s)). The package (30) includes information about the data source location and any access control credentials. The rules container (33) includes rules that stipulate guidelines for the package (30). In certain exemplary embodiments, a rule may indicate if another package is nested inside the given package (30). A rule may indicate restrictions about the kind of display device the package (30) may be assigned to. Rules may also indicate if the data in the field list are layered. Similarly, if there is a nested package, it may be layered too, e.g., a background package is behind the current package, which has the data list for the underlying data to be displayed. A rule may also indicate what portions of the layout related to dynamic data have to be considered for rendering, along with any layering information, to render only those portions of the content instead of the rendering the entire content for display. A nested package, as referred to herein, indicates that there is one or more packages in an arrangement, order, group, etc. that may or may not be related by topic, subject, or use for which any of the included packages may be added to the arrangement, order, group, etc. by a link(s) or by embedding the packages themselves inside the arrangement, order, group, etc. A package included inside a nested package can also be a nested package itself. Nesting of packages would, for example, allow one or more of the packages within the nested package to be reused over and over. Layering indicates the sequencing of package elements, helps identify which elements are visible and which ones are hidden.

Figures 33, 34:
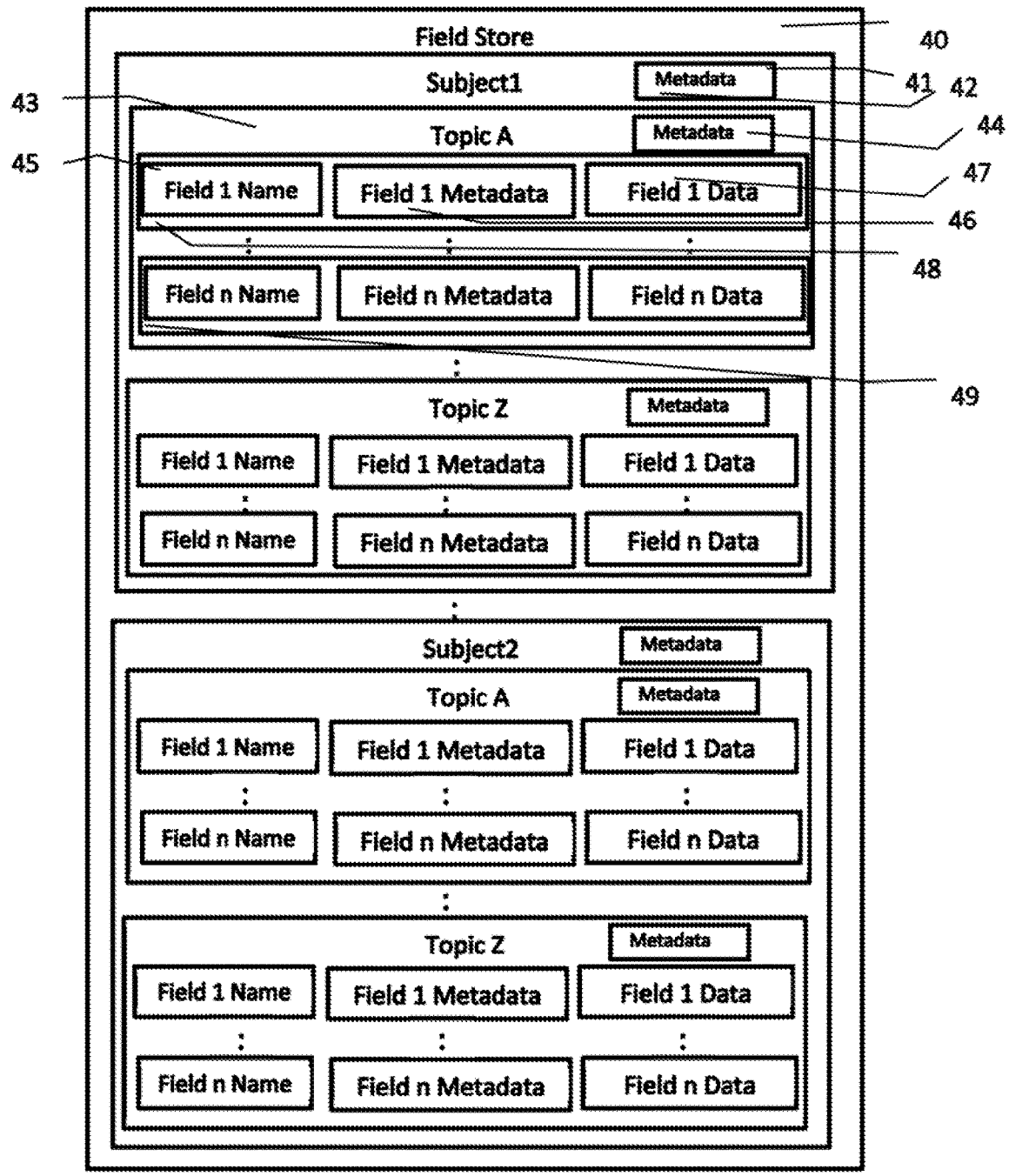
FIG. 33 shows an internal structure of a field store according to an embodiment of the invention.
FIG. 34 shows a field as used in the package's data list according to an exemplary embodiment of the invention.

Referring now to FIG. 33, a block diagram data model of an internal structure of a field store (40) that is generated or created is shown, in accordance to an embodiment of the invention. The detail of data for a package's data list (32) is obtained from the field store (40). Each data item that goes in a package's (30) data list (32) corresponds to a field (48).

The field (48) is used to store multimedia or one or more media objects or elements, such as rich text, plain text, sound (audio), graphics, video, or the like; these multimedia elements are part of the package (30) that is eventually rendered for display on the display device. Each field has a name (45), and there is metadata (46) associated with the field (48), and then the field data (47) itself. The metadata (46) includes the life span of the data, whether the data is cacheable, display attribute(s) for the data, and data origin details. The metadata (46) also indicates whether the data (47) is static or dynamic. If the field data (47) can hold either the data or a link to the source of the data, it will be indicated in the field metadata (46). Topic (43) holds a set of fields, (48, 49). Topic Metadata (44) is associated with each topic, indicates if the topic includes another topic, and the relevant details. The topic metadata (44) also includes information as to whether the topic (43) is exportable outside the field store (40). Subject (41) holds a set of topics. Subject metadata (42) associated with each subject (41) has information about access control for various topics it holds. The field store (40) is a collection of subjects (41). Topic, subject, and field store together may be referred to as sets. The main purpose of the field store is to hold multiple fields (48). Using sets allows fields to be categorized so that the latter are manageable and efficient to use.

FIG. 34 shows the field (48) as used in the package's data list (32) according to an embodiment of the invention. The field (48) includes a namespace (50) associated with each data item recorded in the package (30).

Figure 35:
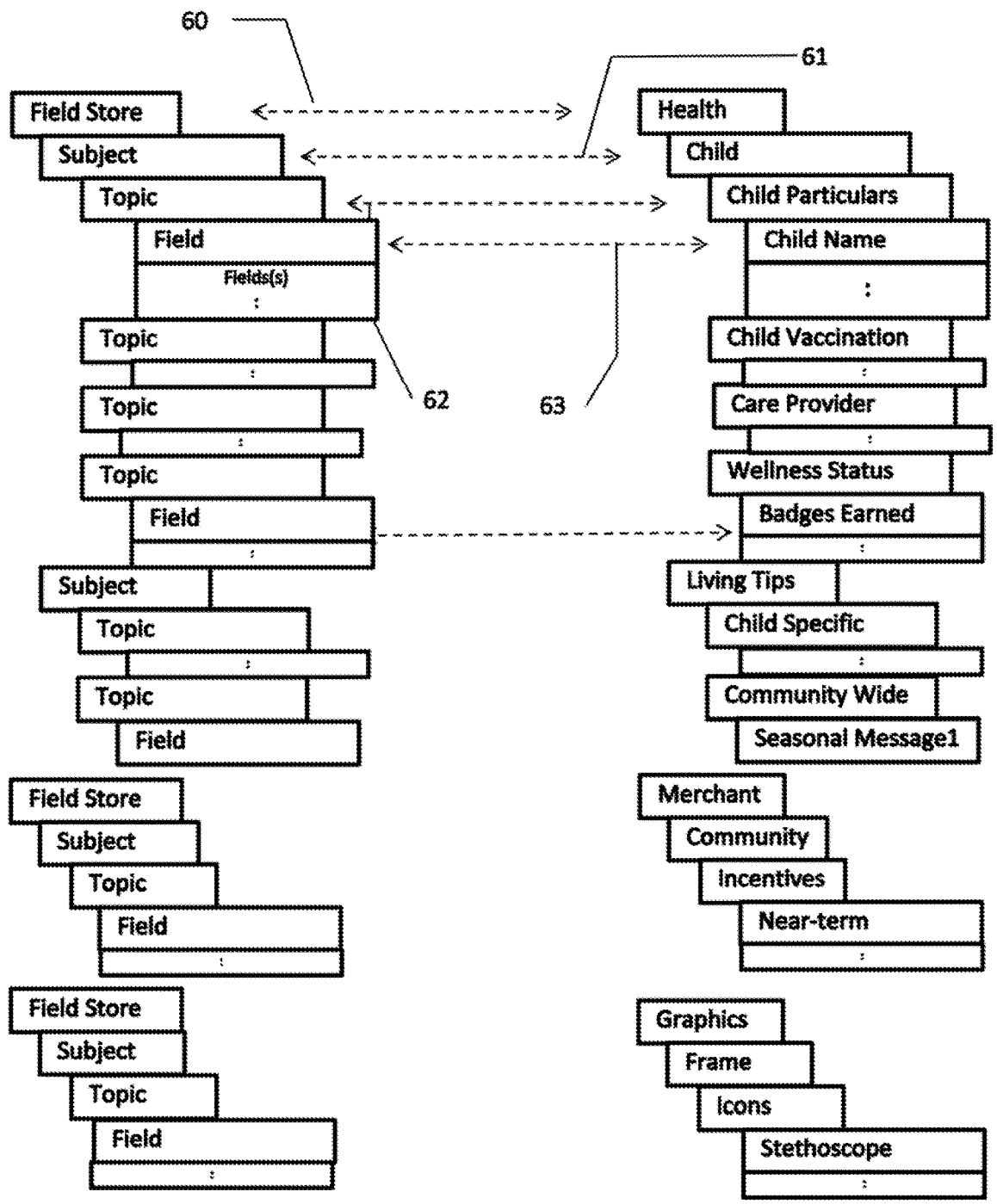
FIG. 35 shows a hierarchy of data of multiple field stores for Child Health Report according to an exemplary embodiment the invention.

FIG. 35 shows a hierarchy of data in multiple field stores according to an exemplary embodiment of the invention. Health is an exemplary field store (60). Health has two exemplary subjects (61): "Child" and "Living Tips." The subject "Child" has four topics (62): "Child Particulars," "Child Vaccination," "Care Provider," and "Wellness Status." The topic "Child Particulars" has only one exemplary field (63) shown here, which is "Child Name," although there could be more. "Merchant" and "Graphics" are other exemplary field stores. Other specific fields may be contemplated, but are not shown for brevity and ease of viewing. FIG. 35 only shows the name for each item, and other particulars, such as metadata, although possibly present, are not shown.

Figure 36:
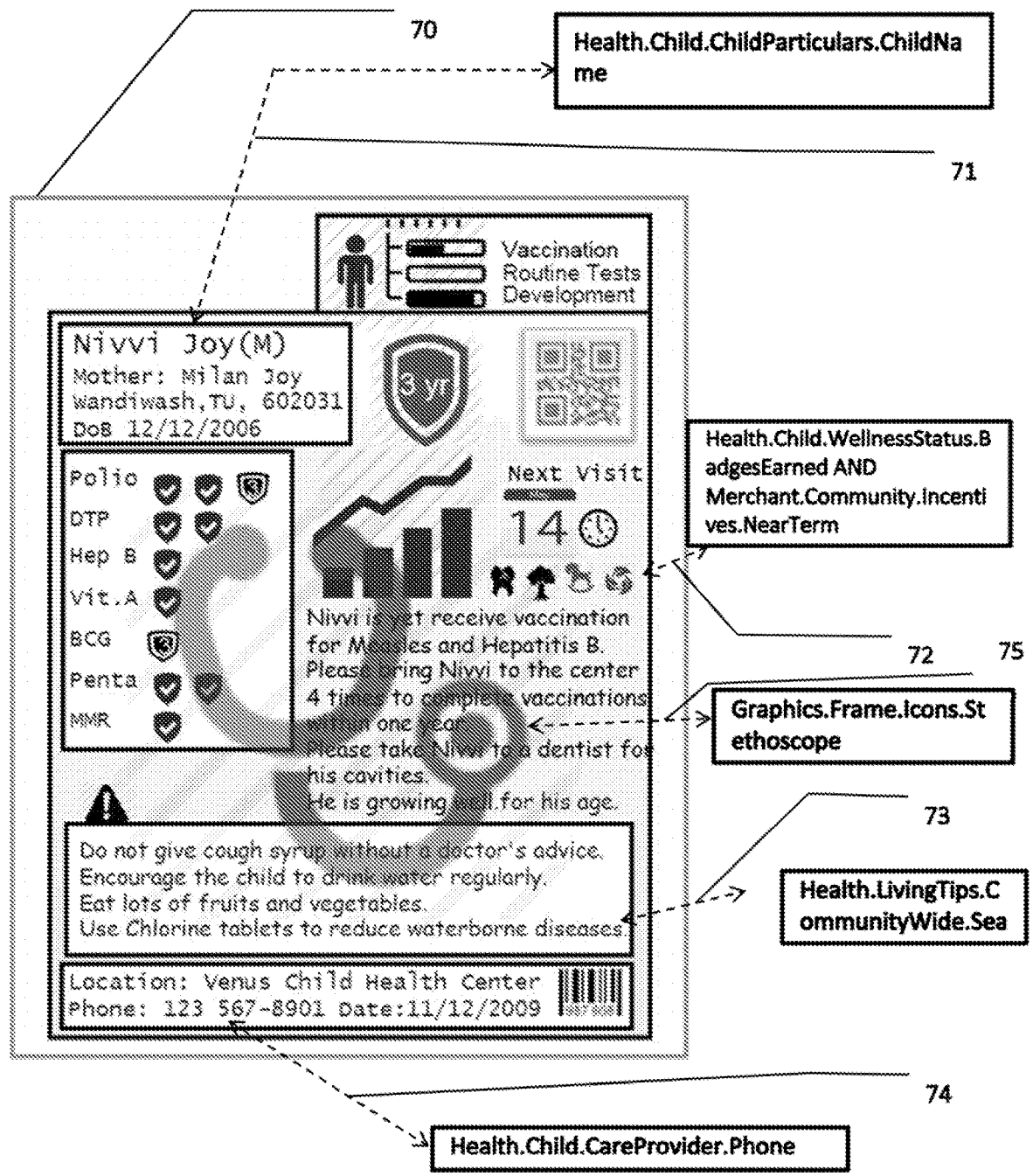
FIG. 36 shows rendered content displayed on a display device according to an exemplary embodiment of the invention.

FIG. 36 shows a rendered package (including content) displayed on a display device (70) in accordance with an exemplary embodiment of the invention. The display device (70) may be an embodiment of the display devices described above, such as the display device (12). In FIG. 36, the display device (70) shows the AIS/content being displayed. The exemplary AIS shown here is a Child Health Report (CHR). The rendered content is made up of fields. A few exemplary fields are shown. The exemplary name of the child of concern, "Nivvi Joy," is obtained because the package (30) for Nivvi Joy included a field with namespace (71) "Health.Child.ChildParticulars.ChildName." Similarly, exemplary "BadgesEarned" and "NearTerm" fields are used to obtain corresponding icons (72) as shown. An exemplary field "SeasonalMessage1" is used for corresponding text (73) shown. An exemplary phone number (74) is obtained using a field "Phone." A field "Stethoscope" (75) is an exemplary field that contains static data. The previously mentioned limitations of a predefined format are overcome with this CHR rendered on the display device (70). The CHR is updatable and is customized to the needs of the specific child and parents. It advantageously provides a type of educational tool that identifies more about health intervention and best practices for healthy and safe living.

Figure 37:
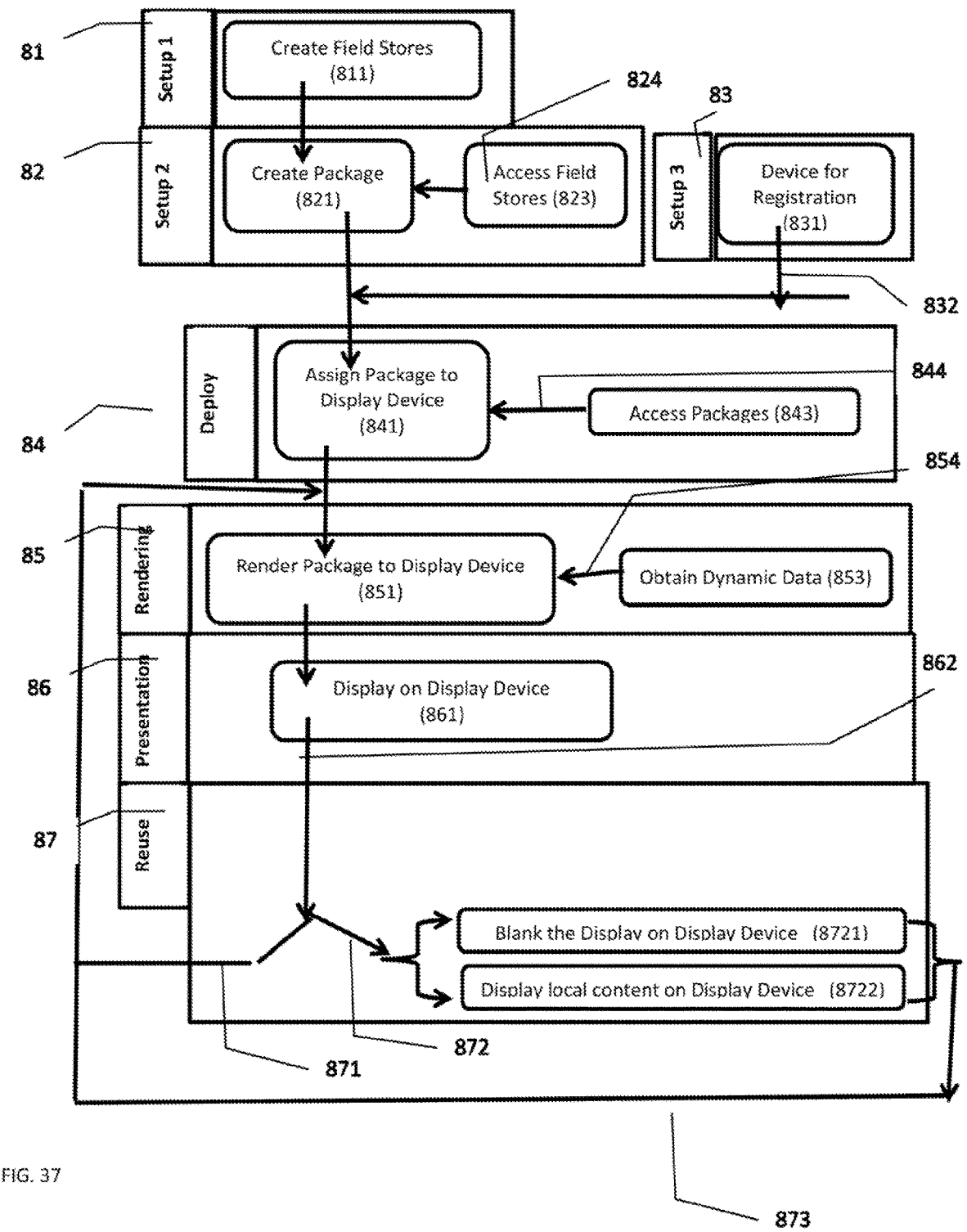
FIG. 37 summarizes steps in managing a display on a display device according to an embodiment the invention.

FIG. 37 shows an embodiment that summarizes steps in managing and displaying content on a display of a display device (12) according to an embodiment of the invention. The steps may be embodied in an algorithm automatically executed by a CPU, for example, the CPU (1501) described above for the content source (1528) or the execution steps may be invoked by an administrator or user. In other embodiments the algorithm maybe implemented to be executed on several CPUs or different CPU in a virtual environment. The first phase is a "Setup 1" (81). During this phase field stores are created (811) from a user interface or an existing schema. A schema is a representation of the details associated with the fields (and in some embodiments, the details associated with the field stores) described in a formal language such as XML. Further details about the field stores creation are discussed below with respect to FIGS. 41, 42, and 43. Details of the field store were discussed above with respect to FIG. 33. In "Setup 2" (82), those field stores (823) are accessed (824) while creating packages (821). The "field store" access in "Setup 2" also involves identifying the data source to be accessed later for the actual data during the "Rendering" phase, which is described below. In "Setup 3" (83), a display device that is available from a list of display devices (831) is registered (832) with a platform. In certain embodiments, the registration occurs when identification particulars, for example a physical address, a virtual address, a name, a well-known identifier, or an identification number, of the display device are made available or provided to the platform so that the platform is later able to communicate with the display device.

In a subsequent "Deploy" phase (84), the package is assigned to one or more (i.e., to one or a group of) display devices (841). The display devices may be grouped by their characteristics, such as their screen dimensions, color depth, resolution, etc. A preview of accessed packages (843) as it would appear on the display device will be available (844). In other embodiments, more than one package may be assigned to a display device or to a group of display devices.

In the next phase, called "Rendering" (85), triggers, such as by human input, invocation by application, inputs from external devices, or the like, will cause the package to be rendered for the display device (851). Human input occurs when an administrator or user may use an application or another device, for example, a mouse, keyboard, or haptic touch screen physically or wirelessly connected to the content source to start the trigger. The trigger may also be generated periodically. The trigger may result from the initial interaction of the display device with the platform. In an exemplary embodiment, a user couples the display module with the content source, as described above, and the content source informs the platform about the display module. The platform then informs the relevant application, and the application then generates the trigger. As part of rendering (854), dynamic data will be obtained (853) from the data source (field store) that was identified earlier (823). In the next phase, called "Presentation" (86), the display device displays the content (861), until one of two possible events occurs (862). The first event (871) is due to the occurrence of the previously mentioned triggers, and new content is generated because either the package content has been updated or a different package has been assigned to the display device. The other event (872) occurs due to an internal mechanism in the display device. In certain situations the internal mechanism will cause the display device to go blank (8721) and in other situations the display device will display a previously rendered package (including content) that is stored locally on the display device (8722) in memory. Eventually the display device that has had its display updated due to the internal mechanism experiences the previously mentioned triggers and has new content generated (873) and displayed.

The field stores (40), in accordance with an embodiment of the invention, may also be used directly on the display device (i.e., instead of performing the steps deploy (84) and rendering (85) on the platform, they will be performed on the display device itself) to mark (or determine) the layout (31) while preparing the data list (32) and identifying the rules (33) (see FIG. 32.). In this case, what was compiled may be saved as a package and stored on a database with the platform or elsewhere on a network, or in memory on the display device, if the display device includes memory, and the package is assigned to the display device.

Figure 38:
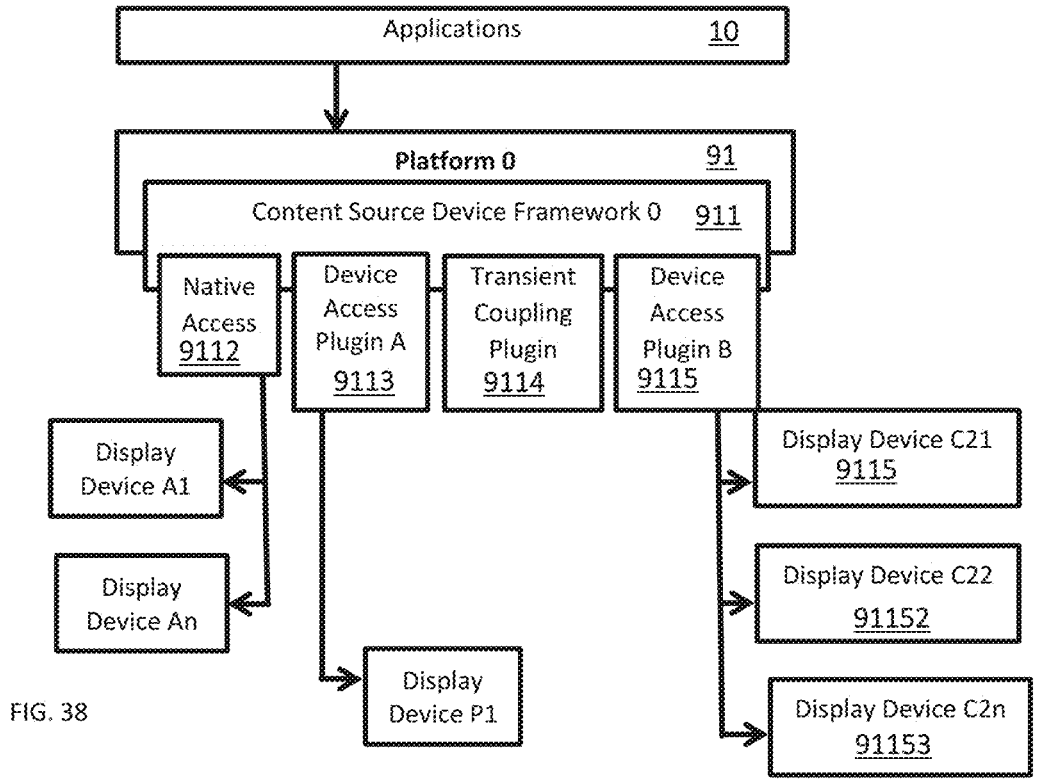
FIG. 38 shows display devices connected to a platform according to an embodiment of the invention.

FIG. 38 shows display devices connected to a platform in accordance with an embodiment of the invention. There may be multiple display device proxies associated with a platform. For example, native access (9112), (also referred to as native pass thru/through (2031) in FIG. 31), device access plugin A (9113), transient coupling plugin (9114) and device access plugin B (9115) may be associated with platform 0 (91) through content source device framework 0 (911). Each of the content source device framework (device access technology packs) may have none or one or more display devices connected to them. For example, the device access plugin B (9115) has many display devices associated with it, such as a display device C21 (91151), display device C22 (91152), up to display device C2n (91153).

Figure 39:
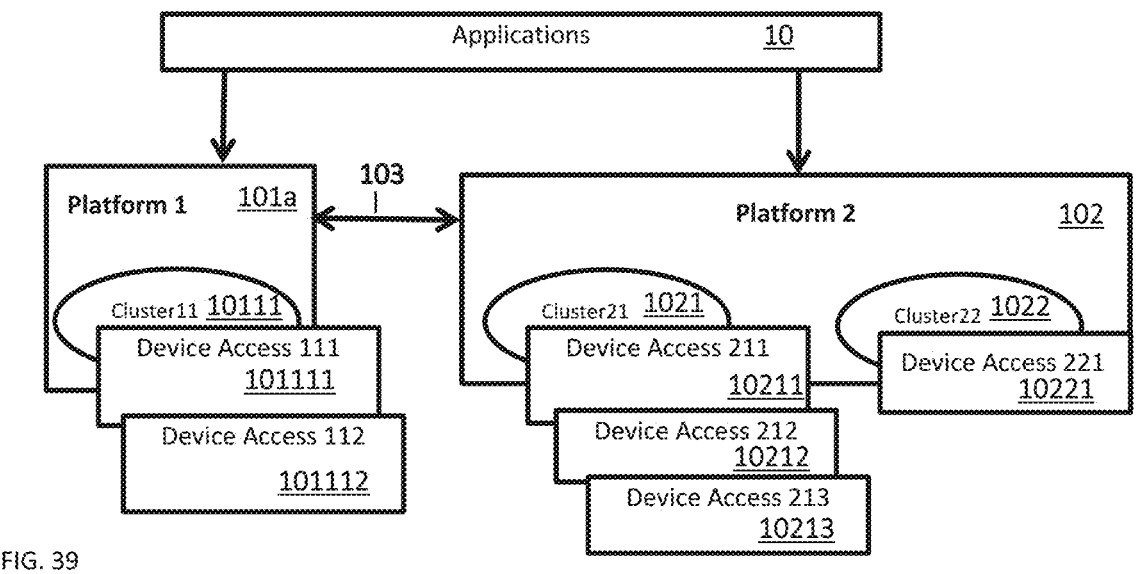
FIG. 39 shows a topology of a network of display devices according to an exemplary embodiment of the invention.

FIG. 39 shows a topology of a network of display devices in accordance with an exemplary embodiment of the invention. In this case, the concept of logical grouping (user-defined groups) of device access technology packs into clusters is contemplated. It is to be understood that there are display devices connected (e.g., via the transient electrical and frictional coupling described above) to the device access technology packs. The exemplary embodiment includes two platforms, platform 1 (101a) and platform 2 (102), which communicate with the applications (10). The platforms can communicate with each other (103), mostly for the discovery of managed devices, locating data sources, and for supporting clustering services. Platform 1 (101a) includes two device accesses grouped into a cluster. Cluster 11 (10111) includes device access technology pack 111 (101111) and device access technology pack 112 (101112). Platform 2 (102) includes two clusters, cluster 21 (1021) and cluster 22 (1022). Grouping clusters enables manageability of the device access technology packs and related display devices. Cluster support also enables high availability of device access technology packs and display devices connected to them. The cluster 21 (1021) includes device access technology pack 211 (10213), device access technology pack 212 (10212) and device access technology pack 213 (10211). In this embodiment, the cluster 22's (1022) device access technology pack 221 (10221) is a backup for the cluster 21 (1021). Clusters may also enable inventory of managed display devices.

Figure 40:
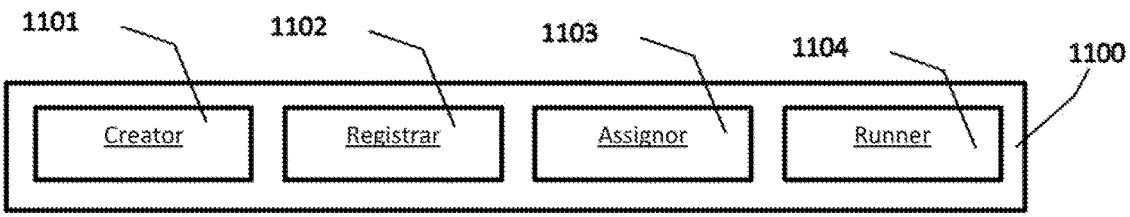
FIG. 40 shows an application's user interface with links according to an exemplary embodiment of the invention.

FIG. 40 shows an exemplary embodiment of an application user interface with four menu element links (e.g., hyperlinks or buttons) (1100) in accordance with an embodiment of the invention. This application UI is part of the content source device. A creator (1101) is used to create fields for topic, subject and field store. A registrar (1102) is used to register a display device or display module with the platform. An assignor (1103) is used to assign a package to the display device. A runner (1104) is used to render the data in the package and transfer it to the display device for presentation or display, as described above. In alternative embodiments, these menu element links may be hosted in different applications, which may not be part of the content source device, but external to content source device.

Figure 41:
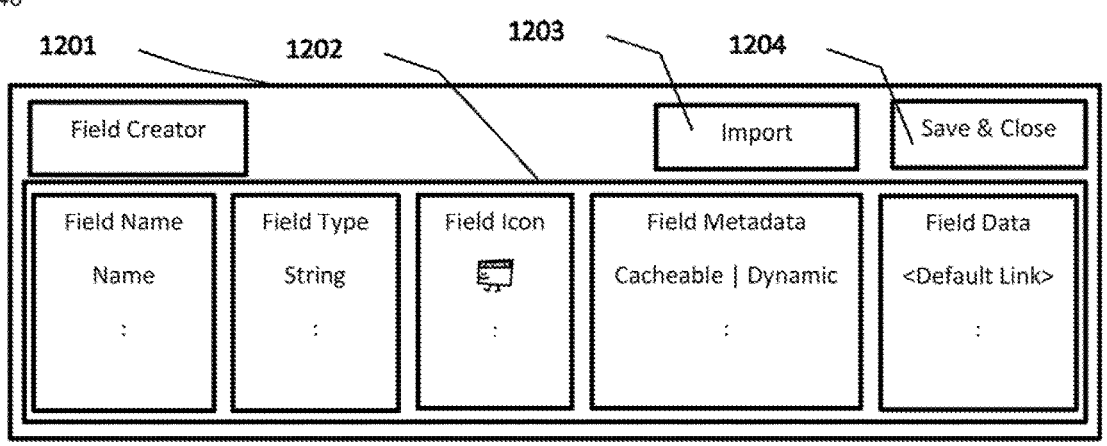
FIG. 41 shows an application's user interface to create fields according to an exemplary embodiment of the invention.

An application user interface (1201) shown in FIG. 41 appears when the UI element "Creator" (1101) in FIG. 40 is selected by a user or administrator, in accordance with an exemplary embodiment of the invention. In this embodiment, field creator details (1202) associated with a field are entered manually by the user or administrator. The field creator details (1202) include "Field Name," "Field Type," "Field Icon," "Field Metadata," and "Field Data." Other details could be included. In an alternative embodiment, details associated with a field are created by importing text files or similar representations, such as a schema. A user interface link "Import" (1203) provides this functionality. A link "Save & Close" (1204) is supplied by the application to save the fields created.

Figure 42:
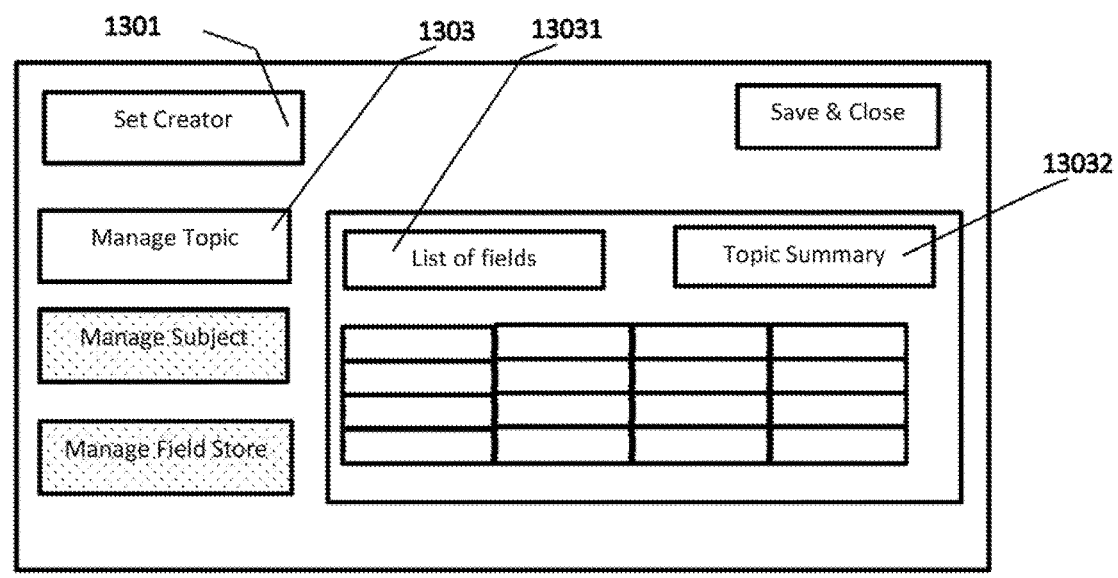
FIG. 42 shows an application's user interface to manage sets according to an exemplary embodiment of the invention.

FIG. 42 shows an application user interface and its elements to create various sets (1301) in accordance with an exemplary embodiment of the invention. "Manage Topic" (1303) provides an interface to list the fields that constitute a topic (1301). Details of the topic are made available through a user interface "Topic Summary" (13032). The user interface elements for "Manage Topic" (1303), "List of fields" (13031), and "Topic Summary" (13032) may be presented to the user or administrator, for example, as links or buttons.

FIG. 43 shows text files being used to import fields in accordance with an exemplary embodiment of the invention. In particular, XML data and schema are used to import the fields, as would be understood by a person of ordinary skill in the art. It would also be understood by a person of ordinary skill in the art that there would be various other ways to import the fields and sets in addition to what is shown here. These other ways contemplated within the spirit and scope of the invention.

As discussed earlier, embodiments of the invention may provide three modes. What has been described so far is the "standard mode." The platform may also or instead manage the display device(s) in advanced modes. Exemplary advanced modes, as mentioned above, may be the show source mode (SS mode) and the follow source mode (FS mode).

Figure 44:
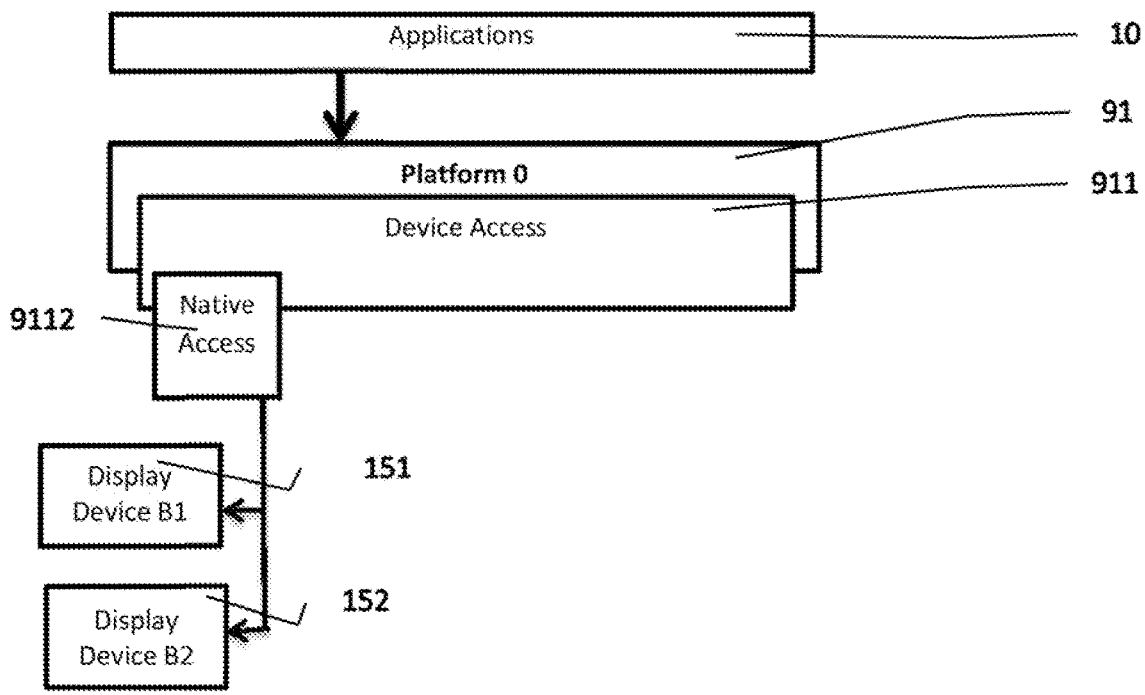
FIG. 44 shows a "show source" mode according to an exemplary embodiment of the invention.
Figure 45:
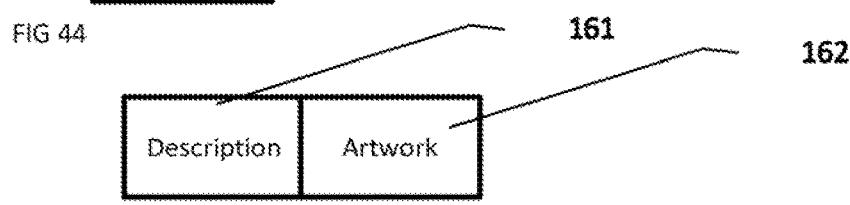
FIG. 45 shows a "show source" mode with structure of the content according to an exemplary embodiment of the invention.
Figure 46:
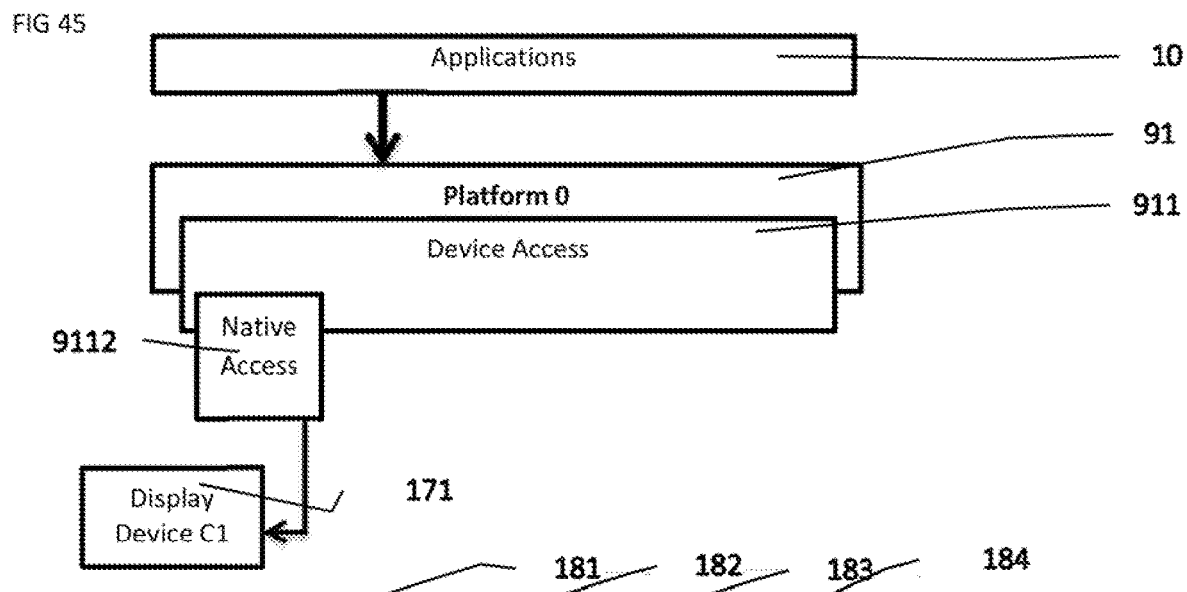
FIG. 46 shows a "follow source" mode according to an exemplary embodiment of the invention.

In the show source mode, the application identifies the content source (e.g., a mobile device or smartphone) and informs the platform about this content source. The platform gets access to the information from the content source to be displayed. The information is then rendered into one or more images or objects for one or more of the identified display devices, and then the image(s) is sent periodically to the one (or more) display device(s) for display. FIGS. 44 and 45 illustrate the show source mode. The mobile device, with application (10) and platform (91), has two display devices, display device B1 (151) and display device B2 (152) connected to it. In certain embodiments the mobile device will transiently and frictionally couple to these display devices using a coupling receptacle coupled, directly or indirectly, to the mobile device, for example, using a gliding receptacle like that shown in FIGS. 19 and 20. In this case, the coupling receptacle couples to the coupling connectors on the display devices, as described elsewhere herein. The display devices B1 (151) and B2 (152) are connected to the device access technology pack (911) via the native pass thru mechanism (9112). FIG. 45 indicates that the information to be shown in this embodiment is structured as "Description" (161) and "Artwork" (162). The platform (91) renders the information, sends the "Description" (161) to the display device B1 (151), and sends the "Artwork" (162) to the display device B2 (152). Such a system provides a structure that is analogous to a multi-display setup or a multi-head setup. The exemplary show source mode in this embodiment may also be referred to as "1×2" (i.e., "1-by-2"), wherein "1×2" refers to 1 row of 2 display devices. In another embodiment having, for example, eight display devices, "4×4" refers to 4 rows with 4 display devices in each row. In general, an embodiment may be referred to as "m×n," indicating m rows with n display devices or modules in each row. Regardless of the number and arrangement of display devices, the platform (91) obtains parameters such as the display device characteristics discussed above, the structure of the information to be rendered, and any user or administrator input about the presentation style to decide how to render the package (including content) appropriately so that it may be displayed on the display devices to provide a multi-display setup. It is contemplated that instead of a mobile device such as a smartphone being the content source it may be any other computing or mobile device, such as a laptop, tablet, phablet, or the like that manages the show source mode.

Embodiments of the invention further provide that a platform can understand the details of the SS mode, when the display devices are arranged or arrayed together. For example, one display device is a base display device in a group of display devices that constitute the multi-display setup. During the registration, the base device registers itself and also provides information about the other display devices it is aware of (i.e., those that are already or become connected to it). The base display device may be one that transiently electrically and frictionally couples to the content source, as described in the provisional patent application Ser. No. 62/123,804 by the same inventor. In other embodiments, the base display device may use existing wired and/or wireless technologies (instead of the transient e\electrical and frictional coupling mechanism) to provide the native ass thru mechanism described above to get connected to the platform.

The platform renders the package, including the content to be displayed on the multi-display setup. The platform may break up the content to be displayed. For example, the content may be split the content into portions that match the number of display devices in a display device array and their layout. The portions are then rendered by the platform. Each portion is assigned an address or other identifier of the particular display device where the content corresponding to the portion is to be displayed. The data set of rendered portions is then sent to the base display device. The base display device may then parcel out the rendered portions to the appropriate display device in the array for display. In accordance with embodiments of the invention, a single data and control path from the platform to the display devices is provided. With a single path it is a simpler design because it requires less circuitry and logic than multiple data and control paths. With multiple paths, the platform would have to manage multiple endpoints. Nevertheless, embodiments having multiple paths (e.g., parallel paths) are contemplated and are included within the scope of the invention, for example, as discussed below with respect to FIG. 53.

In accordance with embodiments of the invention, the SS mode may be of two types—a "Clone" SS mode and an "Extended" SS mode. In the Clone SS mode, the same rendered portion of the content may be displayed on two or more of the display devices in the multi-display device setup. In the Extended SS mode, there is no repetition of the portion rendered, i.e. all the display devices in the multi-display device setup may carry different portions of the content.

Figure 47:
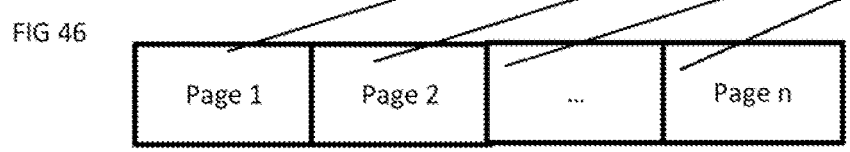
FIG. 47 shows a "follow source" mode with structure of the content according to an exemplary embodiment of the invention.

The other mode mentioned above, the follow source (FS) mode is now discussed in more detail. In the FS mode, the user or administrator browses the content on the mobile device (e.g., a smartphone) as a content source. The application identifies the content source and informs the platform about the content source. The platform gets access to the information from the content source that is being displayed or to be displayed on a display of the content source, renders the information into an image for the display device, and the image may be displayed on the display device as well. The user or administrator can browse the content on the mobile device by using, for example, touch navigation on the mobile device, or by using wearable technology, such as wearable smart glass. The content in this case may be structured as a collection of pages of content (181, 182, 183, and 184), as shown in FIG. 47. When the pages are being navigated through on the mobile device by the user or administrator, the current page navigated to is also rendered and displayed on the display device. It is contemplated that other computing devices instead of the mobile device could similarly manage the FS mode, such as a tablet, phablet, or the like. The distinctive aspect of the FS mode is that the content is browsed on the mobile device and a user or administrator may view the same content on the one or more display devices, whereas in the SS mode, the content is partitioned, rendered, and then displayed on one or more display devices and is not necessarily first viewed on the mobile device, smartphone, tablet, phablet, etc.

The package, when created, may have multiple layouts, and the package has information identifying which layout is to be rendered for which display device. When the layout is being created it is also assigned information about the mode (standard, SS, or FS). The reason the mode detail is stored is because at runtime the platform needs to know which mode is to be used for the display devices and hence the target display device's(s') characteristics for rendering the package contents are needed. For example, consider an exemplary package to be created for a retail store. A layout, referred to as detail layout, provides details for the primary/base display device and may also have reference (or include information related) to other layouts, and the package will include those other layouts for any other associated/ancillary display devices. The package may also include a summary layout that identifies the orientation/location of, or the relationship between, the display devices relative to each other. There could be, for example, a set of display devices for showing pricing and associated information for three items and another associated display device that periodically updates its display element to show details of one of the three items.

It also may be possible to combine the SS and the FS modes, making them available together in certain embodiments. During registration, the display device (s) indicates to the platform which modes it can support. The platform may then decide based on the content and user or administrator action which content is to be rendered for SS mode and which content is to be rendered for FS mode. An exemplary situation would be in a teaching classroom. The teacher's mobile device or smartphone has the platform that drives other display devices on the classroom wall and those in the possession of the students. The display devices on the classroom wall will be in SS mode, whereas the display devices in the possession of the students will be in FS mode. In another exemplary situation, a weather application on a mobile device or smartphone might show just a weather summary on the mobile device's or smartphone's screen. The display device in the possession of a user or administrator might be showing the same summary, whereas a display device on the wall might be showing details of the weather conditions.

Figure 48:
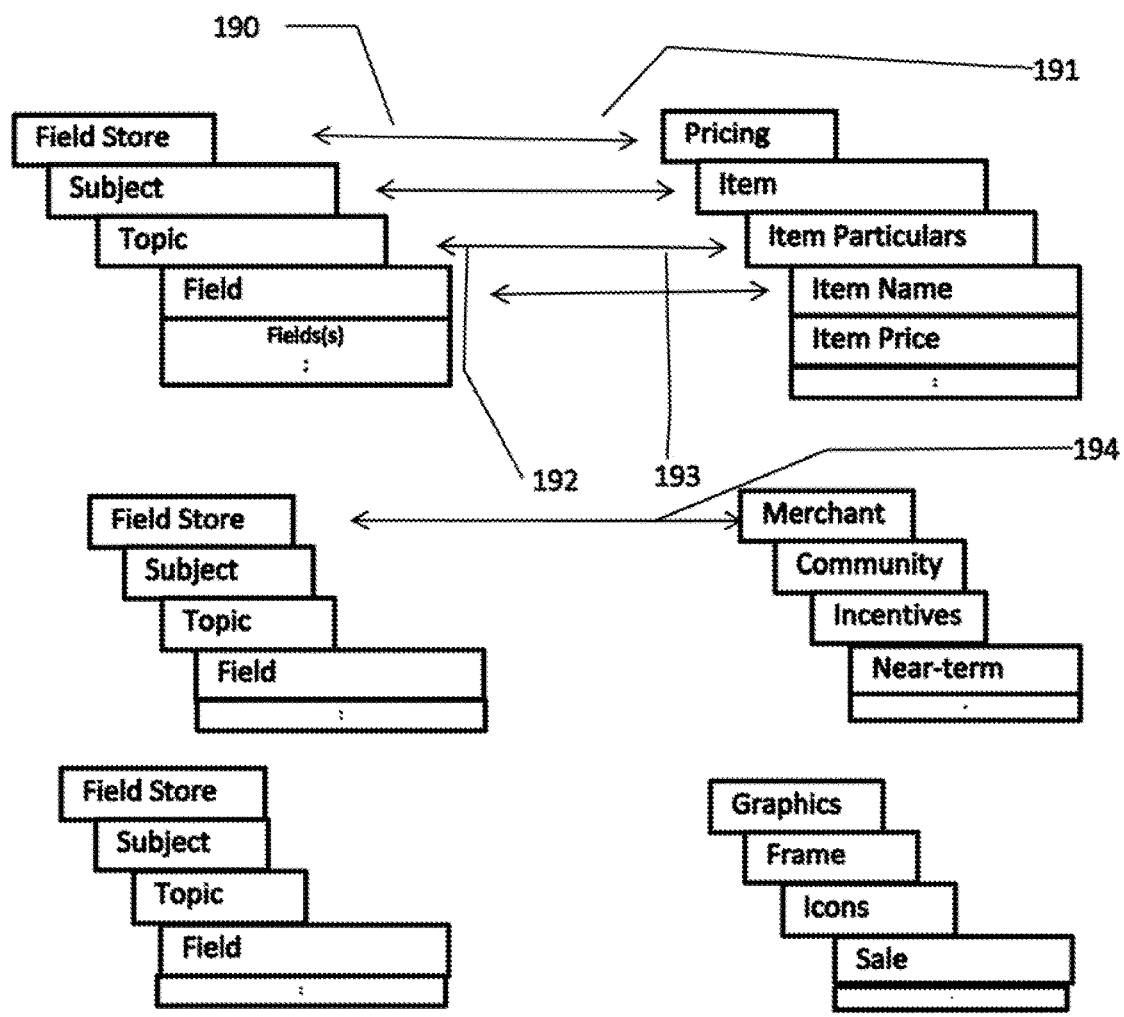
FIG. 48 shows a hierarchy of data in an exemplary embodiment of multiple field stores for Digital Signage according to the invention.

Turning now in more detail to digital signage, in accordance with an exemplary embodiment of the invention, FIG. 48 shows a hierarchy of data for multiple field stores. Pricing is an exemplary field store (190) that includes one exemplary subject (191): "Item." The subject "Item" has one topic (192): "Item Particulars." The topic "Item Particulars" may include numerous fields. As shown in the embodiment of FIG. 48, there are two such exemplary fields (193): for example, "Item Name" and "Item Price." "Merchant" and "Graphics" are other exemplary field stores. Other specific fields are not being shown for brevity and ease of viewing, but may also or instead be included.

Figure 49:
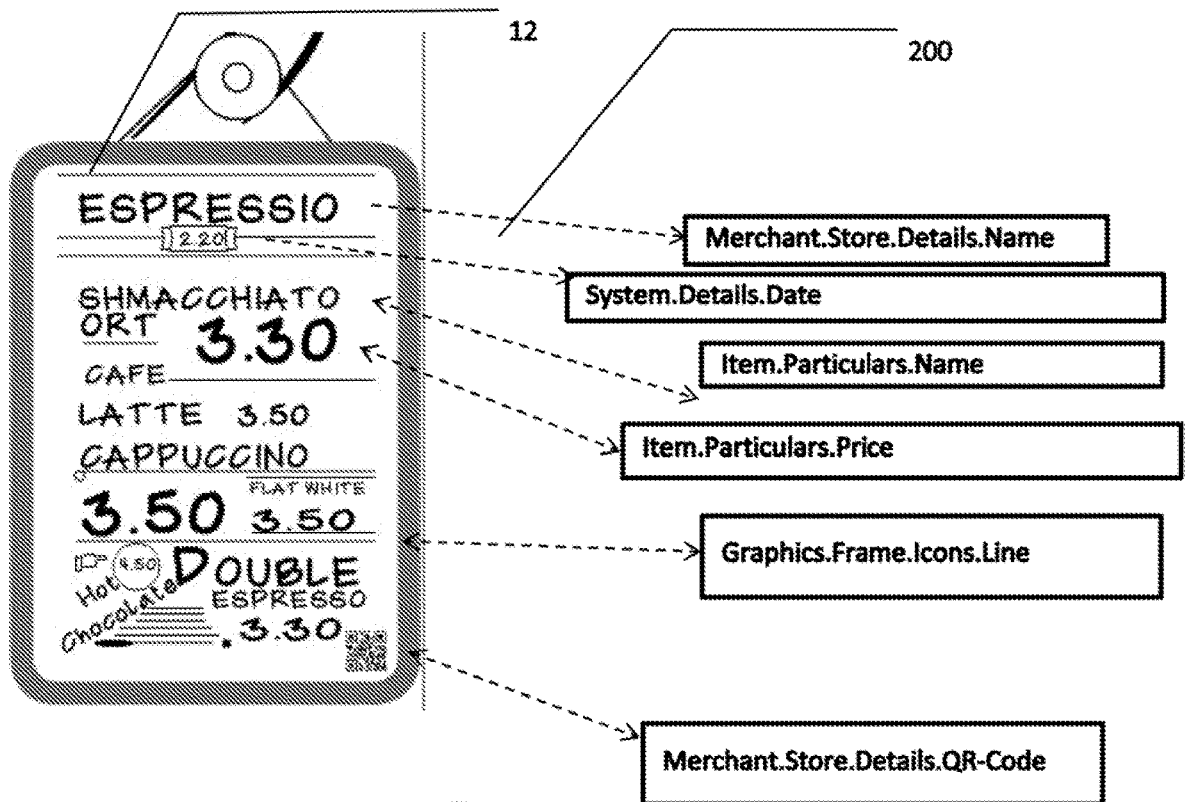
FIG. 49 shows a rendered package (including content) displayed as digital signage, with a price list, in a display device according to an exemplary embodiment of the invention.

FIG. 49 shows a rendered package (including the content) displayed on a display device in accordance with an exemplary embodiment of the invention for digital signage. The AIS/content in FIG. 49 to includes a price list when rendered on the display device (12). The rendered content is made up of fields. A few exemplary fields are shown, including the name of the merchant, "Espressio," which is obtained because the package (30) for the merchant included a field with namespace "Merchant.Store.Details.Name" (200). This embodiment with the price list has advantages over the previously mentioned predefined formatting limitations in the prior art for an AIS. The price list is customized to the needs of the business owner and depends on how she wants to engage the customer.

Figure 50:
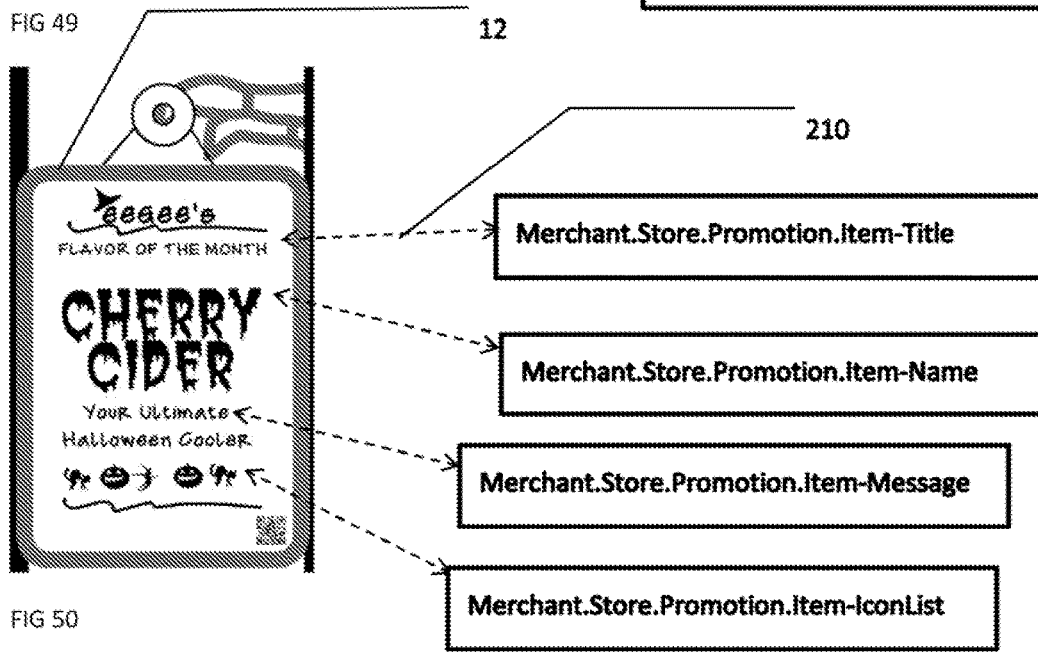
FIG. 50 shows a rendered package (including content) displayed as digital signage, with a seasonal promotional message, in a display device according to an exemplary embodiment of the invention.

FIG. 50 shows digital signage as the display device (12) for a promotional message in accordance with an embodiment of the invention. There are various fields (210) associated with this promotional message. They include "Merchant.store.Promotion.Item-title" and fields for "Item-Name," "Item-Message," and "Item-IconList." There may be other fields too for promotional messages that are not specifically shown, although they are contemplated within the scope and spirit of the invention. The digital signage advantageously provides a type of tool that identifies a promotion a business owner may want to introduce and show to customers.

Turning now to multi-display setups, FIG. 49 shows such a setup in the prior art. Note the independent electrical links (shown as lines with arrow heads) that carry/provide signals, for example, control, address, and data signals, between the video processor(s) or computer system(s) and each display in the multi-display setup. FIG. 52, on the other hand, shows a platform that drives a multi-display device setup according to an embodiment of the invention. The platform (11) includes logic, such as software modules or code, hardware, or their combination to drive the multi-display device setup. A base display device (231a) is electrically coupled or connected (230) to the platform (11). The application (10) and the platform (11) may be hosted together on a computing device, mobile device, smartphone, or the like, or in distributed format, as discussed above. How the platform (11) connects to the display device(s) may be in different ways. For example, in certain embodiments the base display device (231a) may transiently electrically and frictionally couple to the content source as disclosed and described in the previously filed provisional application Ser. No. 62/123, 804 by the same inventor. In other embodiments, the base display device may use existing wired and/or wireless technologies, as would be understood by a person of ordinary skill in the art, instead of the transient coupling mechanism, to provide the native pass thru mechanism described above to electrically couple or connect to the platform. In yet other embodiments, the platform may use one or more plugins with a display device access framework to connect to the display devices.

Referring again to the embodiment in FIG. 52, an electrically conductive link (230) connects the base display device (231a) to the platform (11) to transfer control, address, and data, and may also provide ground and power. Serial links (235, 236) are established by electrical coupling or connection of display devices, in which the base display module (231a) may be a master node and other display modules (232, 233, 234) are slave nodes (although in other embodiments one of the other display modules may be the master and the base display module the slave). The serial links (235, 236) may be embodied in wiring traces for data and control signals, power, and ground in certain embodiments. One display device connects to the next display device over the serial links (235, 236). An exemplary messaging mechanism for the embodiment may be I²C, SPI, or a similar protocol. To ensure fault-tolerance, serial links may be established in the reverse directions to that of the forward links (235), referred to as backup serial links. The serial links (236) may be these backup serial links, which may also be embodied in wiring traces. The serial links (235, 236) may be referred to as directed links. Although the terms forward and reverse have been used herein, either or both of the forward or reverse links may instead be bidirectional in terms control and data flow and are not necessarily unidirectional from the computing system having the platform to the display devices. For example, performance, status, connection type, as well as type of display device information, etc. may flow through any of these links back to the platform while control, address, data information, etc. may flow from the computing system to the display devices through any of these links.

FIG. 53 shows a platform (11) that drives a multi-display device setup in which a base display device (241a) is electrically coupled or connected directly to other display devices (242, 243, 244) in accordance with another embodiment of the invention. The platform (11) in FIG. 53 is otherwise similar to the platform (11) of FIG. 52. One link (240) electrically couples or connects the base display device (241a) to the platform (11). An electrical coupling or connection (245), direct or indirect, between the display devices in this embodiment is a point-to-multi-point connection or link from the base display device (241a) to the other display devices (242, 243, and 244). Content is transferred under control of the platform (11) to the display devices by the link (240) and the electrical coupling or connection (245). A multi-drop protocol such as RS-422 may be used for the electrical coupling or connection (245) between the base display device (241a) and the other display devices (242, 243, and 244).

FIG. 54 shows a flow or steps to update a platform with a change in configuration of a multi-display device setup in accordance with an embodiment of the invention. At time to (with time measured as current time ($t_{cur}$)=previous time ($t_{prev}$)+an increment in time ($\Delta t$)), the platform, the display device, and any ancillary display devices are powered up and the main logic in them, e.g., startup software module or code, hardware, or both, is executed and starts running (251a). In the preferred embodiment, it is the CPU on the content source device that is hosting the platform that will execute the startup software code (251a). The processing element in the base display device and the ancillary display device(s) will execute their local resident logic. Then the platform is made or becomes aware of the presence of the base display device (BDM) (231a) and its configuration of the ancillary display devices (ADMs) (232, 233, and 234) because a signal(s) or change(s) in voltage(s) is (are) detected by the platform from the BDM (231a). For example, the BDM declares its presence to the platform and the platform identifies the presence of the BDM, and then the BDM declares the presence of the ADM(s) and the platform records or identifies the BDM's associated ADM(s). When an ADM is added or removed in the multi-display device setup the BDM detects the change(s) because a signal(s) or change(s) in voltage(s) is (are) detected at the BDM by the code that is being executed on its processing element, and the BDM updates its configuration or reconfigures its awareness of the ADMs with the newly added or removed ADM. The BDM (231a) then declares the change in configuration and updates the platform (11) about the BDM's associated ADM(s) via a signal(s) or change(s) in voltage(s) detected by the platform (11).

Figure 55:
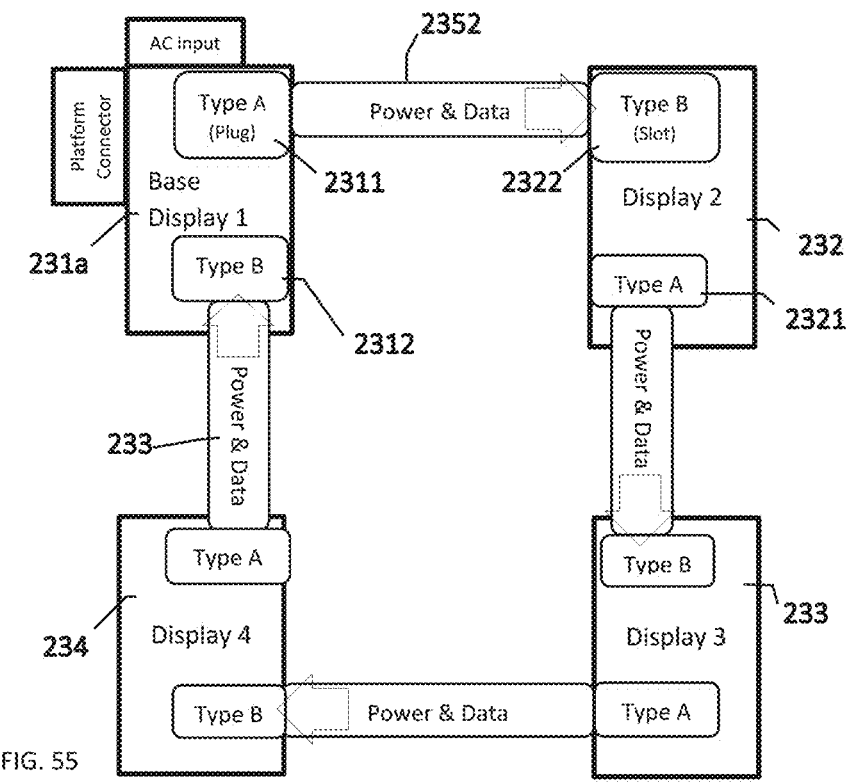
FIG. 55 shows how forward serial links are established in a multi-display module setup according to an embodiment of the invention.

FIG. 55 shows how the forward serial links are established in a multi-display device setup like that of FIG. 52 in accordance with an embodiment of the invention. A base display device (base display 1) (231a) is electrically coupled or connected over a forward serial link (235) to the adjacent ancillary display device (display 2) (232), which is electrically coupled to or connects to ADM (display 3) (233). The display 3 (233) is electrically coupled or connected to another ADM (display 4) (234). The ADM (display 4) (234) is electrically coupled to or connects back to the BDM (display 1) (231a).

In FIG. 55, each display device has two kinds of connectivity endpoints in this embodiment. The BDM (231a) includes Type A (2311) and Type B (2312) connectivity endpoints. Similarly, the display 2 (232) includes a Type A (2321) and a Type B (2322) connectivity endpoints, and so on for the other displays 3 (233) and 4 (234). In certain embodiments, the Type A endpoint is also referred to as a plug and the Type B endpoint is referred to as slot. The forward serial links (235) may carry control, address, power, ground, and data to the display modules, for the sake of brevity only "Power & Data" (235) are shown in FIG. 55. These signals and power and data may be on separate wires, traces, etc., although in some embodiments, some or all of the control, address, and data may be multiplexed on a lesser number of separate wires, traces, etc. It is to be understood that the reverse serial links (236) described above (not shown in FIG. 55 for ease of viewing) also may be included in certain embodiments and operate similarly to the forward serial links. In accordance with an embodiment of the invention, the serial links may use a connecting receptacle like the connecting receptacle (25) as a Type A connectivity endpoint, and use a coupling connector like the coupling connector (22) as a Type B connectivity endpoint, or vice versa.

Figure 56:
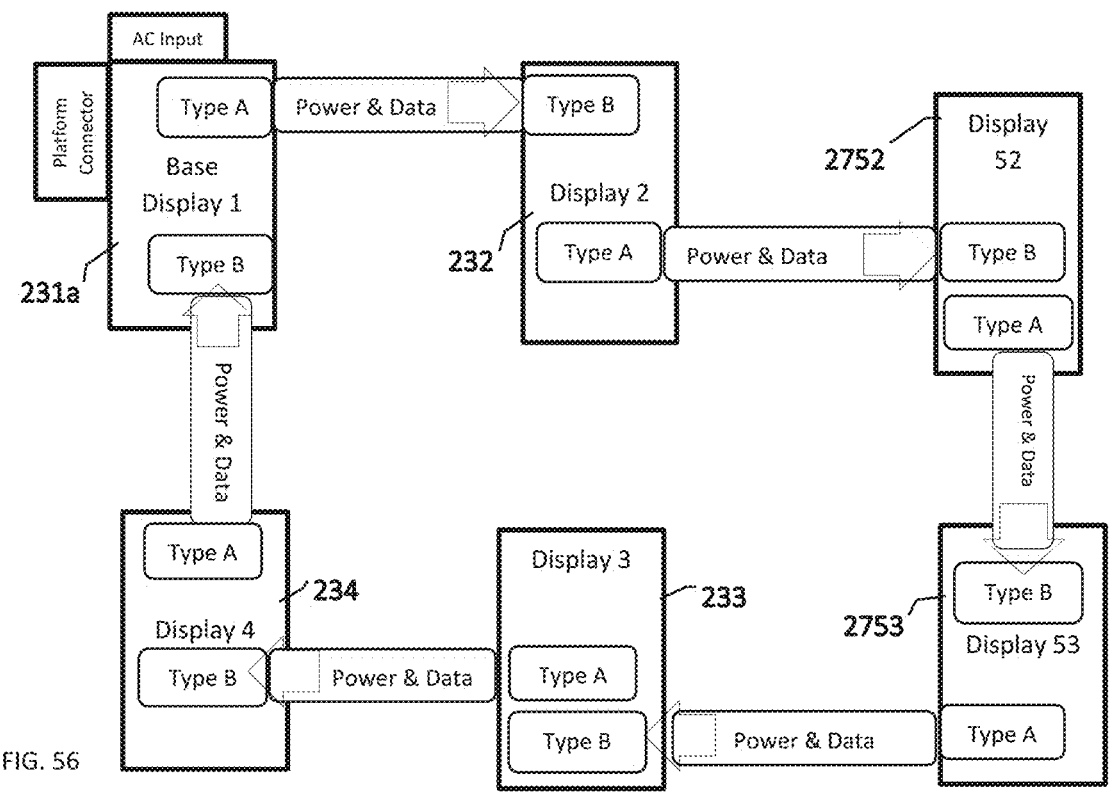
FIG. 56 shows a multi-display module that has been expanded to add two more display modules according to an embodiment of the invention.

FIG. 56 shows a multi-display module setup similar to that of FIG. 55 that has been expanded to add two more ancillary display devices in accordance with an embodiment of the invention. The ADM display 2 (232) now is electrically coupled to or connected to an ADM display 52 (2752), which is in turn electrically coupled to or connected to an ADM display 53 (2753), which is in turn electrically coupled to or connected to the ADM display 3 (233). To increase the number of display devices in a given multi-display setup, the base and ancillary display devices are designed to work either in an existing serial link setup or the point to multi-point setup, as described above. This allows for scalability, to increase or decrease the number of display devices being used in a given multi-display device setup by one or more, making an overall larger or smaller display. It is to be understood that the reverse serial links described above (not shown in FIG. 56 for ease of viewing) also may be included in certain embodiments and operate similarly to the forward serial links.

Information Display Device that Engages a Visitor or Audience

More details are now provided about engaging a visitor or audience. In accordance with embodiments of the invention, the platform enables various options to engage the visitor, such as by cross-sell, upsell, automatic layout selection based on feedback, or broadcast to a smartphone with icons indicating personalized pricing available and fixed advertisement area(s). The personalized pricing may include coupons, special deals, targeted financial instruments, such as payment plans, and so on. A person of ordinary skill in the art will understand that there are other ways to engage the visitor not specifically described in embodiments herein, but nevertheless these other ways are contemplated to fall within the scope and spirit of the present invention.

In accordance with an embodiment of the invention, the platform is capable of working with an analytics infrastructure (AI). The analytics infrastructure is a collection of software modules and services that may reside on a server system or may be co-hosted on the infrastructure that hosts the platform as discussed herein. Infrastructure refers to a set of hardware resources and software resources, such as a server system or a group of servers, which may include software code, hardware, or a combination of both to provide various functions such as data storage, data processing, data analysis, etc.

FIG. 59 shows an overview of a display device (10a) as a hardware platform in accordance with an embodiment of the invention. The display device (10a) may include a very low power network connectivity (11a), such as a wireless connectivity provided by Bluetooth LE. The display device (10a) also may include very low power-consuming display element (12a), such as a display element based on a bi-stable display technology like ePaper. As a hardware platform, the display device (10a) also includes a controller (13a), such as TI's CC2540 or Dialog Semiconductor's DA14580, a memory (14a), such as DRAM and/or Flash, and a power source (15a), such as a coin cell battery(ies) or AA or AAA battery(ies). The display device (10a) also may include an input sensor interface (16a) to various other sensor subsystems, such as a camera (161a), a light sensor (162a), or other sensors (163a). The input sensor interface (16a) and the sensor sub-systems (161a, 162a, and 163a) are optional. The display device (10a) may include other exemplary features of the display device (2, 12) or the other display devices described above as well as those disclosed in the provisional patent application Ser. No. 62/176,798 by the same inventor.

A retail store, museum, or other enterprise or organization may want to engage the visitor or audience using the display device (10a). The process of engaging the audience is referred to as an "engagement" herein. The engagement may be used to sell, announce something, provide information, etc. to the visitor or audience about a product, service, location, etc. FIG. 60 shows at least two kinds of engagement modes (2a), i.e., dedicated display engagement (21a) and connected display engagement (22a) in accordance with embodiments of the invention. A device that performs engagement of either kind is referred to as an "engagement device." The dedicated display engagement (21a) is when the engagement is displayed on a dedicated display device, such as the display device (10a). The connected display engagement (22a) is initiated by a device that is similar to the display device (10a) as disclosed with respect to FIG. 59, but without a display element, also referred to as a headless-display device. Estimote, a product available from Estimote, Inc. (http://estimote.com/), is a hardware beacon transmitter that is a simple example of a headless-display device that may be used in the connected display engagement (22a). With the connected display engagement (22a), the display used for this engagement may be the shopper's/visitor's mobile device display or any other display that is not dedicated for this engagement system, such as a smartphone, tablet, phablet, etc. The engagement may include visual items/indicators presented on the display device (10a), on the mobile display device, or on these other types of displays for viewing by the visitor, and may also include audio cues that the visitor may hear to attract the visitor to view the display device (10a), the mobile display device, or these other displays. The indicator may include an LED or an icon in the display device.

FIG. 61 discloses details of an announcement (200a) in accordance with an embodiment of the invention. The announcement (200a) may be made by the engagement device periodically that does the engagement. It may be made as frequently as ten announcements every minute or one announcement every minute, although other frequencies are contemplated. The purpose of the announcement (200a) may be to inform/notify an application running on the shopper's/visitor's/audience's mobile device(s), such as a smartphone, about the engagement. Bluetooth LE-based beacons and Apple's iBeacons have announcement mechanisms that are known. FIG. 61 shows the announcement (200a) with two fields, i.e., announcement ID (2001a) and item identification (ID) (2002a). The announcement ID (2001a) is either a globally unique identifier or an identifier that is unique to that locale or site. An exemplary identifier may be 16 bytes long, although other lengths are contemplated. The item identification (2002a) is optional, and identifies the item about which the engagement is active; it may be a string, number or an URI, or a combination of those literals, where an URI encompasses URLs, URNs and other ways to identify the item. The shopper's/visitor's/audience's mobile device(s), such as a smartphone, can include a downloadable application or have an application like the application (124a) to act as a receiver or handler, which contacts a remote server to resolve or interpret the announcement ID (2001a) and get further information that relates to this announcement ID (2001a). The shopper/visitor/audience can interact with the application using the information obtained, and information related to this interaction is collected for the purpose and use of predictive analysis, which will be described below. A campaign also will be described further below.

FIG. 62 discloses details of a dedicated display engagement device (21a) in accordance with an embodiment of the invention. The dedicated display engagement device (21a) is an example of the display device (10a) that displays the rendered image of an engagement (211a), which it would have received from the content source device, for example, from a content source device disclosed above and in the previously identified provisional patent applications by the same inventor. The dedicated display engagement device (21a) also sends out the announcement (200a) to the shopper's/visitor's/audience's mobile device(s), such as a smartphone; in certain circumstances, such as during testing, the recipient may be the store's mobile display device or other display device.

FIG. 63 shows details of a connected display engagement device (22a) in accordance with an embodiment of the invention. As discussed previously, the display device (10a) without the display element is referred to as a headless device (222a), and the input sensor interface and the sensor sub-systems are optional. An example of a minimalist headless device is Estimote, Inc.'s hardware beacon emitter mentioned above. The headless device (222a) may send out the announcement (200a) to the shopper's/visitor's/audience's mobile device(s), such as a smartphone; in certain circumstances such as during testing the recipient may be the store's mobile device or other display device.

In accordance with an embodiment of the invention, the display device (10a), such as the display devices described above and in the provisional patent application Ser. No. 62/176,798 by the same inventor, may have associated packages and data elements (also referred to as data items) displayed on it that collectively constitute one or more campaign(s) in an engagement. The campaign may include one or more packages. In one embodiment, the data items displayed on a display device are based on an engagement that contains one campaign, and that campaign consists of one package. In other embodiments, a campaign may consist of two or more packages or an engagement may contain multiple campaigns In accordance with an embodiment of the invention, the analytics infrastructure may use machine learning (ML) to plan and propose either changes to an existing package or a new package and its data items, thus impacting the campaign(s) and the relevant engagement(s). The term of art, "machine learning," as would be understood by a person of ordinary skill in the art, indicates the ability to process collected data, learn patterns, and predict the known behavior. These embodiments facilitate adoption of such ML techniques, which are used to help derive insights that promote conditions to influence shoppers' behavior favorably during the engagement. Machine learning techniques enable predictive analytics. In a preferred embodiment, the platform at deployment is prepared/bootstrapped/coldstarted with packages for predefined messages, and it is the analytics module, included as part of analytics infrastructure ((127a) in FIG. 74), which is the repository of the software logic that provides access to the ML techniques to enable predictive analytics. In one scenario, the analytics module obtains data for inputs, such as details about the products sold during the selling period, the messages and announcement(s) that were used for engagement with the customers during the selling period, how the customer interacted with the announcement(s), and the customer demographics. It then combines the obtained data with other forward-looking data, such as inventory level and supply chain-related information about the products to be sold, the day and time of the sale, and other metrics, to decide the outputs, which are the messages and announcements for the engagement. As part of that scenario, the analytics module provides a message-based recommendation engine (MBR), which would be embodied in software code. The MBR provides recommendation for messages for cross-sell, upsell, down-sell, repeat-sell and suggestive-sell. In accordance with an embodiment of the invention, the MBR will measure properties of the item(s) sold or being sold. For example, the inputs, which are received from the platform and any third party vendor systems (see FIG. 74 and the description thereof), are properties related to the items sold or being sold that may include the message used to sell the item, date/time of the sale, selling price of the item, inventory level, and so on. The inputs are used to generate a recommendation as an output to the platform, which then may generate messages or announcements for engaging the audience, packages for the messages or announcements to be displayed to the audience, etc., or price information and inventory management information for a store owner, store manager, site administrator, etc. Such a system has the benefit of a computing system to automatically generate the messages or announcements and deploying them to engage the shopper. The system may also be deployed in non-retail environments such as museums, for public signage, hospitals, and others by considering the inputs relevant to those specific environments such that the outputs in those environments may include messages for engaging the visitor or the audience.

Figures 72, 73:
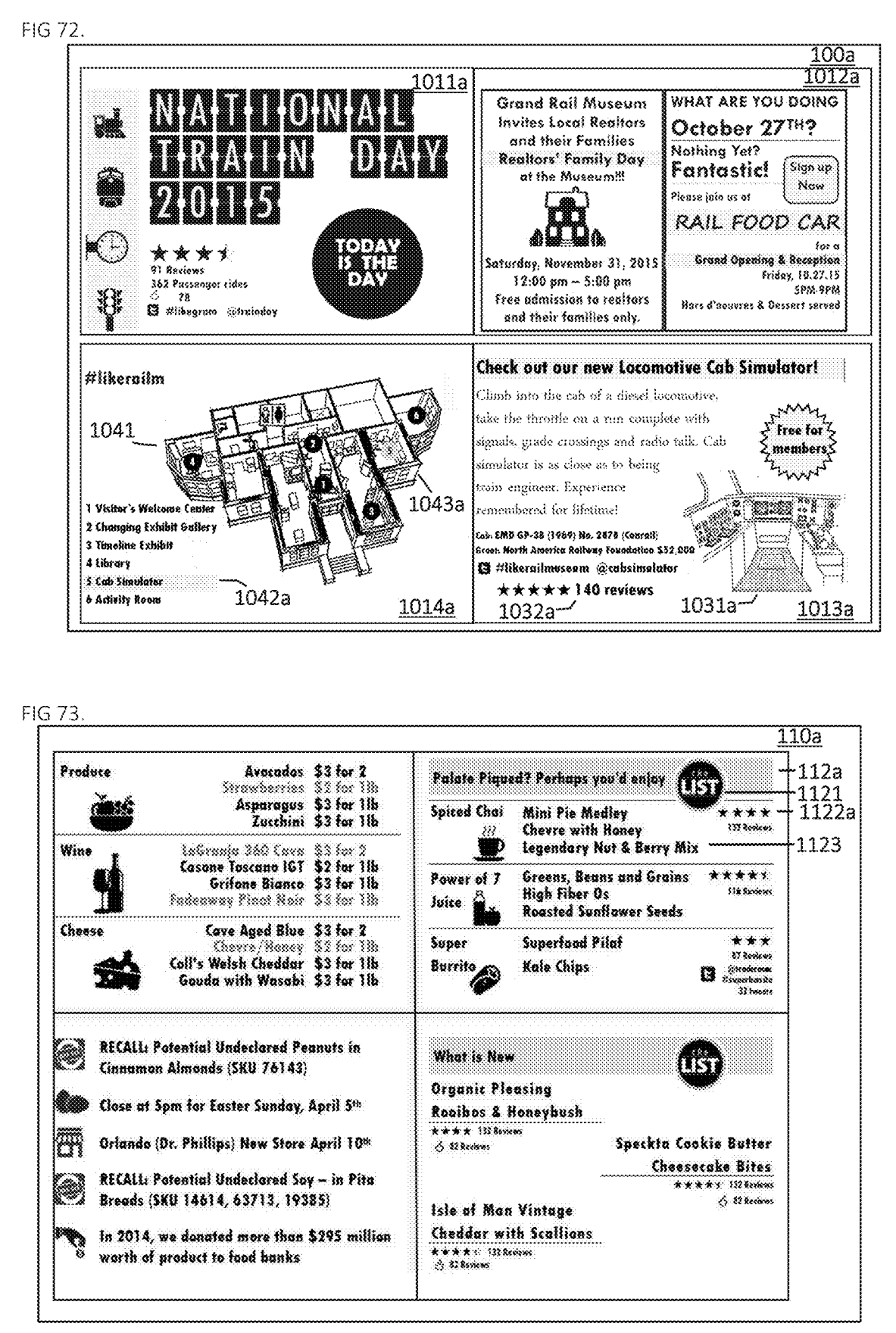

FIGS. 64 and 65 show the relationship between an engagement, campaign and package in accordance with an embodiment of the invention. In FIG. 64, an exemplary engagement, referred to as engagement 1 (31a) includes only one campaign, a campaign 1 (32a), which is based on a single package, package 1 (33a). The engagement 1 (31a) may be part of a super engagement (30a). The presence of the super engagement (30a) is for tiled display devices. FIGS. 63 and 73 and their descriptions below provide further details about a super engagement. In FIG. 65, another exemplary engagement, engagement 2 (41a), includes three campaigns, campaign 1 (32a), campaign 2 (412a), and campaign 3 (414a). The campaign 1 (32a) is being reused (it was previously used for engagement 1 (31a)). The campaign 2 (412a) includes packages 2 and 3 (413a), whereas the campaign 3 (414a) includes a package 4 (415a). A campaign may be considered as a container of packages with additional information, such as the duration of time for which the packages are to be used or until a product runs out or is sold out. Also in this example, the campaign 2 (412a) may further require that the packages 2 and 3 (413a) have to be displayed one after the other. Just like the platform, the package, campaign, engagement, and super engagement include logic that may include software code, hardware, or a combination of both, such as a collection of software modules and services that may reside on a single computing system, on server system, or be distributed on a network of computing systems or servers.

Further to FIGS. 64 and 65, after a package is created it is assigned to a campaign and the campaign in turn is assigned to an engagement. In certain embodiments the package may be assigned to be part of one or more engagement(s). The engagement is then deployed to the engagement device, such as the display device (10a) or a headless display device. Also the announcement may be assigned to a campaign.

Figure 66:
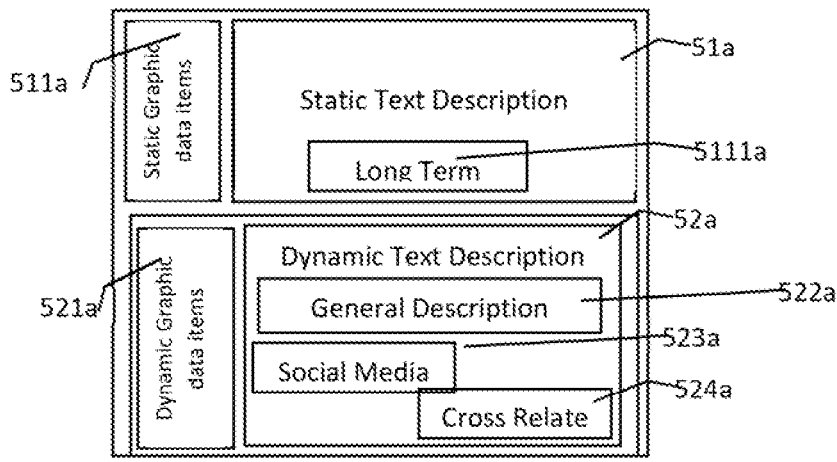
FIG. 66 shows an engagement with content based on static and dynamic elements depicted in accordance with an embodiment of the invention.

FIG. 66 shows various data items that are displayed during an engagement when using either the dedicated display engagement or the connected display engagement in accordance with embodiments of the invention. Further information about data items may be found in the previously mentioned provisional patent application Ser. No. 62/176, 798 by the same inventor. These data items may be understood as having been identified after determining the campaigns and the packages that constitute the engagement to be made. Static data items hold data that do not change just before rendering for display or presentation, and may be either graphics (511a) or text (51a). A long term static text (5111a) may be text that cannot be changed by the campaigns. This can happen if there is an engagement that uses text or graphics for display which may not be indelible for the duration of the engagement or longer. A typical example of the long term static text (5111a) may be a campaign or engagement sponsor's message.

Figure 69:
FIG. 69 shows a rendered image of another engagement for the product in FIG. 68 in accordance with an embodiment of the invention.
Figure 70:
FIG. 70 shows a rendered image of an engagement for yet another product in accordance with an embodiment of the invention.
Figure 71:
FIG. 71 shows a rendered image of an engagement for another product in accordance with an embodiment of the invention.

Dynamic data items hold data that do change and hence they are fetched before rendering of the engagement for display or presentation, and may be either graphics (521a) or text (52a). The dynamic text data items may be further classified as belonging to categories of a general description (522a), social media (523a), or cross relate (524a). The typical source for dynamic data items categorized as social media (523a) are usually the count of reviews, number of likes, Pinterest pin count, and so on that would be available on social media platforms, as would be understood by a person of ordinary skill in the art. For cross relate (524a), the dynamic data items have a relationship to the data items being conveyed as part of the general description (522a). Examples of the general description (522a) dynamic data items may be pricing and sales details. An example for the cross relate (524a) dynamic data items will be an upsell advertisement or cross-sell advertisement, further examples of which are shown in other figures. The decision to cross relate a data item with another campaign, i.e. to establish a relationship between a data item and the other campaign, may be made either manually by a person such as the store owner, store manager, system administrator, or it may be made automatically by a computer program executing on a CPU that is hosting the platform, such as those described above. In a preferred embodiment, the same computing system that hosts the platform will also have the software logic, as in the analytics module, to perform the tasks and recommend cross relate details for the dynamic data items. Further, the analytics module will take into consideration the parameters that characterize the relevant data items and a different campaign that was or will be created. The relevant data items from the different campaign would be included for the current engagement. FIGS. 69, 70, and 71 refer to engagements that actively use cross relate.

Figure 67:
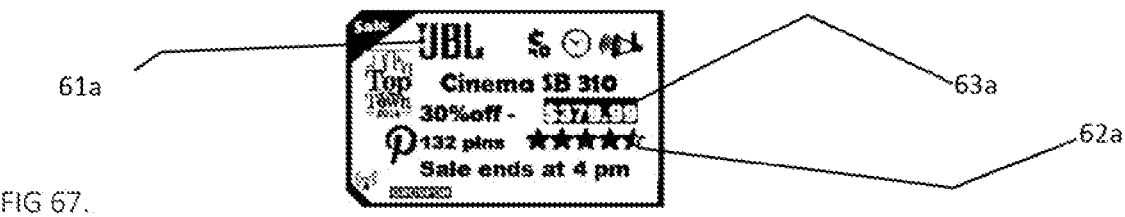
FIG. 67 shows a rendered image of an engagement for a product being sold in accordance with an embodiment of the invention.

FIG. 67 shows the layout of various data items in a display device, such as the display device (10a), in accordance with an embodiment of the invention. It includes certain data items that are static like a name (61a) that does not change for the duration of the engagement. The dynamic data items include pricing (63a) as part of the general description, and the social media data, such as reviews (62a), which may change during the duration of the engagement.

Figure 68:
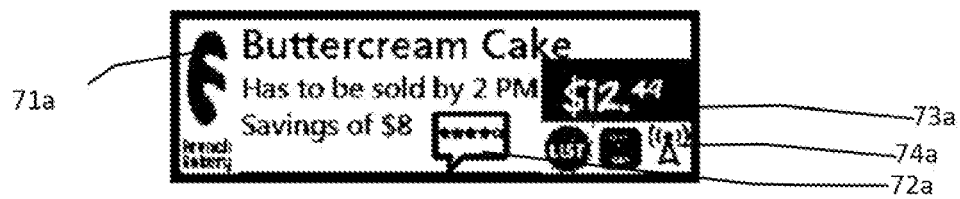
FIG. 68 shows a rendered image of an engagement for another product in accordance with an embodiment of the invention.

FIG. 68 shows various data items being displayed on a display device in accordance with an embodiment of the invention. All the data items together constitute part of one or more package(s) that make up a campaign. The package includes certain data items that are static, which may be both text, such as the name of a product ("Buttercream Cake") and a graphic icon (71a). The dynamic data item may include pricing and sale details as part of a general description (73a), whereas the social media data items may include review information (72a). The icons shown relate to those previously mentioned elements. A radio icon (74a) indicates that this engagement device is sending out an announcement that may be received by a mobile device, such as a smartphone. This is an indication for the customer or visitor to monitor their mobile device.

In accordance with an embodiment of the invention, customer behavior (e.g., customer preferences, customer attributes, product attributes, and others), such as their retail purchasing history, may be monitored and correlated to the engagement that is in effect for developing customer behavior metrics and performance metrics. Thus, either the store manager, a system administrator, or the system itself can automatically (based on machine learning as offered by the analytic infrastructure discussed earlier) make changes to the engagement based on this monitoring and the metrics developed. FIG. 69 shows one such revised engagement for FIG. 68, with different campaign details, and with revisions, some of which are based on customer behavior metrics or performance metrics in accordance with embodiments of the invention. The name of a product (711a) is a static data item and remains the same, but rendered with different font information compared to FIG. 68. In this embodiment, pricing information (713a) also remains the same; even though it is a dynamic data item it has not been revised here. On the other hand, an alternate depiction of social media (712a) is being used in FIG. 69. New dynamic text data items (714a) that promote cross-sell are also shown here. The decision to promote this cross-sell may be either initiated by a store manager, a system administrator, or by the system itself automatically, using the analytics infrastructure and machine learning, as discussed. This cross-sell is to be considered as a service in accordance with an embodiment of the invention.

In accordance with another embodiment of the invention, the campaign may automatically be changed by the system without intervention of the store manager, a site manager, or a system administrator. Further details of this aspect were discussed earlier while discussing the analytic infrastructure and will be further described in reference to FIG. 74.

FIG. 70 shows an engagement display device, such as the display device (10a), showing a different engagement for a different product in accordance with an embodiment of the invention. Here, the exemplary static data item is a product and its manufacturer (821a). As exemplary dynamic data items, pricing (823a) is part of the general description, and others based on social media (822a) are shown along with a rating score and a number of reviews performed to garner this rating. The store manager, site administrator, or other user, or the system itself may decide to add another cross-sell factor to the engagement by identifying other products (824a) in the store that complement the product (821a). The cross-sell of the other products may be made available due to the result of other campaigns that are part of this engagement or engagements.

FIG. 71 shows the engagement display device showing a different engagement for a different product, for example, inside a commercial passenger plane, such as when replacing or adding to a traditional seat-back display device, in accordance with an embodiment of the invention. In this embodiment, the exemplary static data item is a product or product name (911a), pricing is part of a general description (913a), and a social media-based information element (912a) also is included. This embodiment also includes a cross-sell product (914a) that might be of interest to the targeted customer, but the cross-sell product by or from another merchant or provider that is now part of this engagement.

Engagements may be revised to include other campaigns that introduce upsell, cross-sell and repeat-sell, as mentioned above, in accordance with embodiments of the invention. Other types of revisions for other types of targeted engagements or campaigns will occur to a person of ordinary skill in the art and are contemplated to be within the scope and spirit of the present invention. The decision to revise and which campaigns to be used may be either automatic (i.e., performed and implemented by the system of the present invention) or manual (i.e., performed and implemented by the merchant, store manager, or site administrator, etc.). The platform may also communicatively connect to ad (advertising) networks and may have the ability to bring in visitor-specific messages based on the needs of the visitor in accordance with embodiments of the invention. The platform may also tie into or communicate with, for example, the visitor's smartphone, to provide access to a to-do list of the visitor, as might be stored on the visitor's smartphone, so that recommendations for cross-sell, upsell and repeat-sell may be based on the contents of their to-do list. The platform also may provide a mechanism to plug into, communicate with, or support to-do list managers from such companies as Evernote Corp (see https://evernote.com/). The platform may further provide engagement and campaign experiences to the customer of a brick-and-mortar retail store or similar place that are akin to those occurring to online customers of web sites while shopping or purchasing online in accordance with embodiments of the invention.

Although retail store embodiments have been described herein, other embodiments applicable to other verticals, as discussed above, such as museums, hospitals, rental offices, car dealers, hotels, airports, airplanes, shopping malls, boutiques, specialty stores, as well as others that would occur to a person of ordinary skill in the art, are contemplated to be within the scope and spirit of the present invention.

FIG. 72 shows a layout of various elements in a tiled display device (100a) in accordance with an embodiment of the invention. The previously mentioned provisional patent application Ser. No. 62/176,798 by the same inventor referred to a tiled display device as a multi-display setup. The multi-display setup (100a) shown in FIG. 72 includes four display devices (1011a, 1012a, 1013a, 1014a), each similar to the display device (10a). In this embodiment, each multi-display setup or tiled device shows a rendered super engagement in a visual display, such as the super engagement (30a). The super engagement (30a) includes a set of engagements, and may be thought of as an organization or container of engagements, so each constituent display device has its own engagement. Thus the display device (1013a) has its own engagement, which includes multiple campaigns and has dynamic data items for social media (1032a) and static data items that describe the exhibit itself (1031a). The display device (1014a) has a dynamic element (1043a) as part of the general description that labels an exhibit, whereas the layout of the museum itself is static information (1041a). In this exemplary engagement, a "Cab Simulator" information on the display device (1014a) is a dynamic data item (shown highlighted in FIG. 72). The dynamic data item chosen determines which engagement shows up on the display device (1013a). If instead it decided to highlight "Timeline Exhibit" (1042a) as the dynamic data item in the display device (1014a), then the data items that relate to the "Timeline Exhibit" (1042a) will be shown on the display device (1013a) (instead of the data items related to "Cab Simulator"). Within the engagement in the display device (1013a), some of the data items can be static as in an image of the interior of the simulator and a "Free for members" message (1031a), and the dynamic data items could be reviews or other social media information (1032a). This relationship between the engagements is maintained in the super engagement (30a).

FIG. 73 shows a layout of various elements in another exemplary tiled display device (110a) in accordance with an embodiment of the invention. A display device (112a) in this multi-display setup (110a) shows an engagement that may include multiple campaigns. An exemplary campaign consists of static elements (1121a), dynamic elements for social media (1122a), and other general description (1123a).

Figure 74:
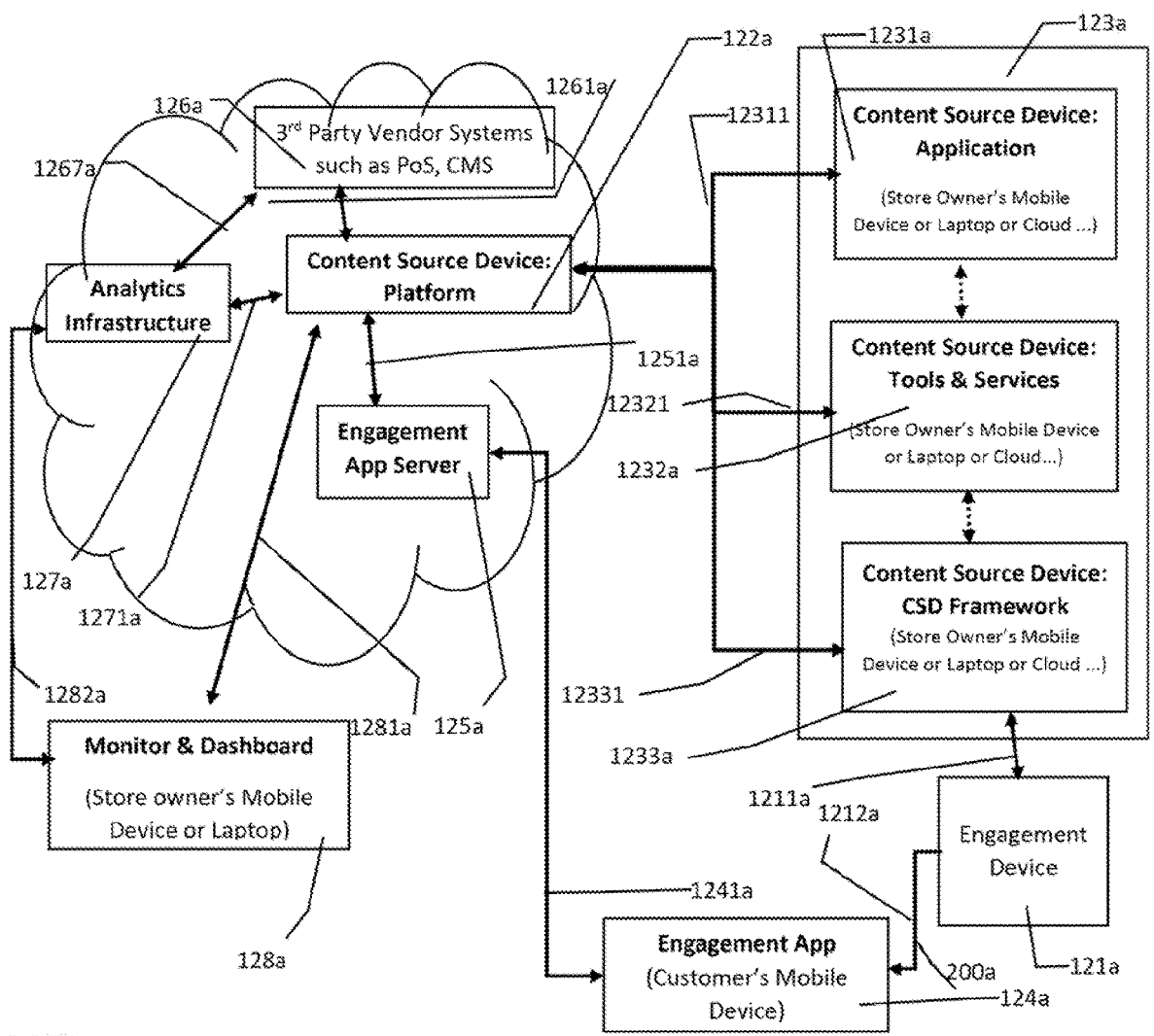
FIG. 74 shows a flow diagram for providing an announcement and illustrates the interaction amongst key components in a platform in accordance with an embodiment of the invention.

FIG. 74 shows a flow diagram for providing an announcement and illustrates the interaction amongst key components in a platform in accordance with an embodiment of the invention. An engagement device (121a), which may be a dedicated display engagement device such as the display device (10a), a connected display engagement device such as a headless device previously discussed, or a multi-display setup such as the tiled displays (100a, 110a) as described above, sends out (1212a) an announcement (200a) to mobile devices in proximity to the engagement device (121a). The proximity range/distance depends upon the wireless networking technology used. For Bluetooth LE it may be approximately 10-30 meters inclusive. A customer's (shopper's, visitor's, or audience's) mobile device(s) (e.g., smartphone(s)) receives the announcement (200a). Information related to the announcement (200a) is then handed over or provided by the mobile device to an application (124a) on the mobile device that handles the information in the announcement (200a). The application (124a) may be provided either by the merchant, the display device manufacturer, or from another source, such as by download from a network or the Cloud. The application then contacts (1241a) an engagement app server (125a) in the Cloud or over another network to learn more about the announcement (200a). The application (124a) on the mobile device, when it contacts (1241a) the server (125a), also provides certain information (such as name, identification, or any other digital identity representing the shopper/visitor/audience and/or their present location or forms of "anonymized" data). Data "anonymization" removes identifying particulars from the data intentionally for privacy protection; it is done by removing personally identifiable information so that the people that the data describe remain anonymous. The server (125a) prepares, based on the information it received (including the announcement (200a)), a personalized message and/or personalized pricing suitable for that customer, as described above. The server (125a) sends (1241a) back to the application (124a) response data that contains the personalized message and personalized pricing as appropriate to the customer. The response received is then either displayed to the customer on their mobile device to influence their behavior or presented on their mobile device in a format (such as a QR Code or Barcode) that may be used or factored into a purchase about to be finalized, for example, with the store. In such an embodiment, the QR Code or Barcode would represent the savings/coupons/special deal that the customer is now entitled to.

FIG. 74 also shows a system of components that makes the visitor engagement possible in accordance with embodiments of the invention. In one embodiment, the engagement device (121a) is a dedicated display engagement device (such as the dedicated display engagement device (21a) discussed earlier) that receives (1211a) engagement details and announcement details from a content source device's framework (1233a) (see the previously mentioned provisional patent application Ser. No. 62/176,798 by the same inventor). A content source device: tools & services (1232a), which is executable software code & logic, creates packages, campaigns and engagements, which may be stored locally in a memory such as the memory (also referred to as local storage) associated with the content source device (1528) described above or stored at one or more remote storage resources or memories accessible to a content source device: platform (122a). The use of the colon ":" indicates that the tools & services is located in a content source device (CSD), and similarly for the other items discussed herein. The data items and layout information are also either stored locally in the local storage or stored on one or more remote storage resources or memories accessible to the CSD: platform (122*a*). The data items and layout are used to create the packages. The details of creating packages was described in the previously mentioned provisional patent application Ser. No. 62/176,798 by the same inventor. The CSD: tools & services (1232*a*) also allows identification of data sources for runtime rendering of the packages. The packages and the campaigns either may be created by a person or the CSD: platform (122*a*). The CSD: platform (122*a*) uses machine learning (ML) to create the packages and the campaigns. The ML workflow joins the engagement created and presented and the actual sales data, such as sales and also other shopper's behavior metrics, to suggest packages and campaigns, which are created and presented automatically. The suggested package may contain all or a portion of the data elements of the previously prepared packages, and also the layout may be the same or different in the suggested packaged when compared to the previously prepared packages.

A CSD: application (1231*a*) manages the setting up of the engagement and initiation of the rendering of the campaign and announcement to make them available for transfer to the engagement device through the CSD: framework (1233*a*). The CSD: platform (122*a*) has a gateway and connectors (1261*a*) to connect to third party vendor systems (126*a*) that are used, such as point of sale, inventory management system and content management system. The CSD: platform (122*a*) also connects to an analytics infrastructure (127*a*) to manage the ML workflow for campaign generation and other shopper/visitor engagement tasks. The announcement sent out by the engagement device (121*a*) is received by the engagement application (124*a*) on the customer's mobile device or smartphone. The application (124*a*) then contacts (1241*a*) the engagement app server (125*a*), which in turn connects (1251*a*) with the CSD: platform (122*a*) to resolve or interpret the announcement (200*a*) received at the engagement application (124*a*). The engagement application (124*a*) then receives (1241*a*) the response data that contains a personalized message and/or personalized pricing, as appropriate, to the customer's activity.

The store owner, site manager, administrator, or other user may monitor the performance and status of the engagement devices (121*a*) from a monitor & dashboard UI (128*a*). This UI connects (1282*a*) to the analytics infrastructure (127*a*) to get insights that have been generated by the analytics infrastructure (127*a*) so that they then may be presented to the store owner, site manager, administrator, or other user. The UI (128*a*) also connects (1281*a*) to the CSD: platform (122*a*) to get information about the status of the engagement devices (121*a*) and the campaign being run on those devices.

Further, in FIG. 74, the CSD: platform (122*a*) collects data from activities such as purchases, price changes, etc., that take place and are related to the usage of pricing signage and announcement signage and sends (1271*a*) the data to the analytics infrastructure (127*a*). For optimization purposes, the platform may inform the analytics infrastructure (127*a*) to collect the data directly retrieved (1267*a*) from other sources such as the third party point of sale system (126*a*). The analytics infrastructure (127*a*) is capable of processing the data collected to predict and subsequently propose the package(s) to be used for pricing signage and/or announcement signage. The processing of the collected data involves preparing customer behavior metrics and performance metrics from the collected activity data to understand and determine the efficacy of the engagement. These customer behavior metrics and performance metrics are developed from a set of measurements related to the engagement based on the data collected.

The engagement device (121*a*) may also or instead similarly support the other engagement mode described above, i.e., the connected display engagement, in accordance with other embodiments of the invention. Moreover, in certain embodiments, one or more of the software modules disclosed herein may be implemented in a cloud computing environment. Cloud computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment. Moreover, one or more of the software modules described herein may transform data and/or representations of physical entities from one form to another.

The specific embodiments described above are merely exemplary, and it should be understood that these embodiments may be susceptible to various modifications and alternative forms. The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed. It should be further understood that the claims are not intended to be limited to the particular embodiments or forms disclosed, but rather to cover all modifications, equivalents, and alternatives falling within the spirit and scope of this disclosure.

The invention claimed is:

1. An apparatus to transfer aggregated information, comprising:
   a display element;
   a coupling contact comprising electrically conductive paths, the coupling contact transiently electrically coupled to a content source during motion between the coupling contact and the content source to establish power and ground, and to provide data signals and control signals from the content source to the electrically conductive paths to transfer the aggregated information for presentation on the display element; and
   wherein an order in which the power and the ground are established, and the data signals and the control signals are provided, is determined by the motion and relative lengths of the electrically conductive paths.

2. The apparatus of claim 1, further comprising a processing element that processes the data signals and control signals to provide the aggregated information in a form compatible with the display element for presentation on the display element.

* * * * *